(12) United States Patent
Deiters et al.

(10) Patent No.: US 12,291,504 B2
(45) Date of Patent: May 6, 2025

(54) SMALL MOLECULE INHIBITION OF SULFOTRANSFERASE SULT1A3

(71) Applicants: University of Pittsburgh—Of the Commonwealth System of Higher Education, Pittsburgh, PA (US); Albert Einstein College of Medicine, Bronx, NY (US)

(72) Inventors: Alexander Deiters, Pittsburgh, PA (US); Kristie E. Darrah, Pittsburgh, PA (US); Mary Frances Cacace, Pittsburgh, PA (US); Ian Cook, Bronx, NY (US); Thomas Leyh, Bronx, NY (US); Ting Wang, Bronx, NY (US)

(73) Assignees: University of Pittsburgh—Of the Commonwealth System of Higher Education, Pittsburgh, PA (US); Albert Einstein College of Medicine, Bronx, NY (US)

( * ) Notice: Subject to any disclaimer, the term of this patent is extended or adjusted under 35 U.S.C. 154(b) by 895 days.

(21) Appl. No.: 17/299,733

(22) PCT Filed: Dec. 10, 2019

(86) PCT No.: PCT/US2019/065442
§ 371 (c)(1),
(2) Date: Jun. 3, 2021

(87) PCT Pub. No.: WO2020/123482
PCT Pub. Date: Jun. 18, 2020

(65) Prior Publication Data
US 2022/0024876 A1  Jan. 27, 2022

Related U.S. Application Data

(60) Provisional application No. 62/777,644, filed on Dec. 10, 2018.

(51) Int. Cl.
*C07D 219/06* (2006.01)
*C07D 215/04* (2006.01)
(Continued)

(52) U.S. Cl.
CPC ......... *C07D 219/06* (2013.01); *C07D 215/04* (2013.01); *C07D 215/48* (2013.01);
(Continued)

(58) Field of Classification Search
CPC .. C07D 219/06; C07D 215/04; C07D 215/48; C07D 249/06; C07D 401/04;
(Continued)

(56) References Cited

U.S. PATENT DOCUMENTS

2006/0079528 A1* 4/2006 Finn ................ A61P 29/00
546/159
2009/0318436 A1* 12/2009 Albrecht ........... A61P 31/00
514/252.04
2012/0088746 A1* 4/2012 Shishido ............ A61P 1/00
514/210.01

FOREIGN PATENT DOCUMENTS

CN     107176922 A     9/2017

OTHER PUBLICATIONS

Tian, et al., "Sulfation of melatonin: enzymatic characterization, differences of organs, species and genders, and bioactivity variation," *Biochemical Pharmacology*, vol. 94, No. 4, pp. 282-296 (Apr. 2015).
(Continued)

*Primary Examiner* — Clinton A Brooks
*Assistant Examiner* — Kyle Nottingham
(74) *Attorney, Agent, or Firm* — Foley & Lardner LLP

(57) ABSTRACT

Provided herein are small molecule compounds and methods inhibiting human sulfotransferase 1A3 (SULT1A3) using
(Continued)

these small molecule compounds. Methods of manufacturing and treatment are also disclosed.

12 Claims, 12 Drawing Sheets

(51) Int. Cl.
  *C07D 215/48*   (2006.01)
  *C07D 249/06*   (2006.01)
  *C07D 401/04*   (2006.01)
  *C07D 471/04*   (2006.01)
(52) U.S. Cl.
  CPC ......... *C07D 249/06* (2013.01); *C07D 401/04* (2013.01); *C07D 471/04* (2013.01)
(58) Field of Classification Search
  CPC ................ C07D 471/04; C07D 215/14; A61K 31/4375; A61K 31/47; A61K 31/4709; A61K 31/473; A61P 3/00; A61P 35/00
  See application file for complete search history.

(56) References Cited

OTHER PUBLICATIONS

International Search Report and Written Opinion issued in International Patent Application No. PCT/US2019/065442, dated Mar. 17, 2020.
International Preliminary Report on Patentability issued in International Patent Application No. PCT/US2019/065442, dated Jun. 25, 2021.
Artimo, et al., "ExPASy: SIB bioinformatics resource portal," *Nucleic Acids Res* 40, pp. 597-603 (2012).
Baker, et al., "Quantum chemistry in parallel with PQS," *J Comput Chem* 30, pp. 317-335 (2009).
Battiste, et al., "Utilization of site-directed spin labeling and high-resolution heteronuclear nuclear magnetic resonance for global fold determination of large proteins with limited nuclear overhauser effect data," *Biochemistry* 39, pp. 5355-5365 (2000).
Berendsen, et al., "Gromacs—a Message-Passing Parallel Molecular-Dynamics Implementation," *Comput Phys Commun* 91, pp. 43-56 (1995).
Berton, et al., "New approaches to antidepressant drug discovery: beyond monoamines," *Nat Rev Neurosci* 7, pp. 137-151 (2006).
Blackwell B. "Monoamine oxidase inhibitor interactions with other drugs." *J Clin Psychopharmacol*, 11(1), 55-59 (1991).
Bradford, "A rapid and sensitive method for the quantitation of microgram quantities of protein utilizing the principle of protein-dye binding," *Anal Biochem* 72, pp. 248-254 (1976).
Brak, et al., "Identification of a New Class of Nonpeptidic Inhibitors of Cruzain," *J. Am. Chem. Soc.*, vol. 130, pp. 6404-6410 (2008).
Castañar, et al., "Chapter Four—Recent Advances in Small Molecule NMR: Improved HSQC and HSQMBC Experiments," *Annual Reports on NMR Spectroscopy* 84, 163-232 (2015).
Chesney, et al., "Risks of all-cause and suicide mortality in mental disorders: a meta-review," *World Psychiatry* 13, pp. 153-160 (2014).
Cook, et al., "Testing the sulfotransferase molecular pore hypothesis," *J Biol Chem* 288, pp. 8619-8626 (2013).
Cook, et al., "The gate that governs sulfotransferase selectivity," *Biochemistry* 52, pp. 415-424 (2013).
Cook, et al., "Tetrahydrobiopterin regulates monoamine neurotransmitter sulfonation," *Proc Natl Acad Sci USA* 114, pp. E5317-E5324 (2017).
Cook, et al., "A nucleotide-gated molecular pore selects sulfotransferase substrates," *Biochemistry* 51, pp. 5674-5683 (2012).
Cook, et al., "High accuracy in silico sulfotransferase models," *J Biol Chem* 288, pp. 34494-34501 (2013).
Cook, et al., "The allosteric binding sites of sulfotransferase 1A1," *Drug Metab Dispos* 43, pp. 418-423 (2015).
Cook, et al., "The structure of the catechin-binding site of human sulfotransferase 1A1," *Proc Natl Acad Sci U S A* 113, pp. 14312-14317 (2016).
Cook, "Controlling Sulfuryl-Transfer Biology," *Cell Chem Biol* 23, pp. 579-586 (2016).
Dajani, R., Hood, A. M., and Coughtrie, M. W. (1998) A single amino acid, glu146, governs the substrate specificity of a human dopamine sulfotransferase, SULT1A3. *Mol Pharmacol* 54, 942-948.
Delaglio, et al., "NMRPipe: a multidimensional spectral processing system based on UNIX pipes," *J Biomol NMR* 6, 277-293 (1995).
Dormer, et al., "Highly Regioselective Friedländer Annulations with Unmodified Ketones Employing Novel Amine Catalysts: Syntheses of 2-Substituted Quinolines, 1,8-Naphthyridines, and Related Heterocycles," J. Org. Chem. 2003, 68, 467-477.
Girvin, et al., "Determination of local protein structure by spin label difference 2D NMR: the region neighboring Asp61 of subunit c of the F1F0 ATP synthase," *Biochemistry* 34, 1635-1645 (1995).
Gochin, et al., "Paramagnetic relaxation assisted docking of a small indole compound in the HIV-1 gp41 hydrophobic pocket," *ACS Chem Biol* 6, 267-274 (2011).
Goldstein, "Sources and physiological significance of plasma dopamine sulfate. *J Clin Endocrinol Metab*," 84, 2523-2531 (1999).
Heroux, et al., "Physical characterization of a monoamine-sulfating form of phenol sulfotransferase from human platelets," *Molecular pharmacology* 34, 194-199 (1988).
Hildebrandt, et al., "Human SULT1A3 pharmacogenetics: gene duplication and functional genomic studies," *Biochemical and biophysical research communications* 321, 870-878 (2004).
Kurogi et al., "Concerted actions of the catechol O-methyltransferase and the cytosolic sulfotransferase SULT1A3 in the metabolism of catecholic drugs," *Biochem Pharmacol*, 84(9), 1186-1195 (2012).
Le Corre, et al., "Steady-state pharmacokinetics of dopamine in adult patients," *Crit Care Med* 21, pp. 1652-1657 (1993).
Lu, et al., "Crystal structure of human sulfotransferase SULT1A3 in complex with dopamine and 3'-phosphoadenosine 5'-phosphate," *Biochem Biophys Res Commun* 335, 417-423 (2005).
Merikangas, et al., "Lifetime prevalence of mental disorders in U.S. adolescents: results from the National Comorbidity Survey Replication—Adolescent Supplement (NCS-A)," *J Am Acad Child Adolesc Psychiatry* 49, 980-989 (2010).
Meiser et al., "Compexity of dopamine metabolism" *Cell Communication and Signaling*, vol. 11, No. 34, E1-18 (2013).
Nobili et al., "Dopamine neuronal loss contributes to memory and reward dysfunction in a model of Alzheimer's disease" *Nature Communication*, 8, 14727, 14 pages (2017).
Olgiati, et al., "Early improvement and response to antidepressant medications in adults with major depressive disorder. Meta-analysis and study of a sample with treatment-resistant depression," *J Affect Disord* 227, 777-786 (2018).
Riches, et al., "Quantitative evaluation of the expression and activity of five major sulfotransferases (SULTs) in human tissues: the SULT pie", *Drug metabolism and disposition: the biological fate of chemicals* 37, 2255-2261 (2009).
Salman, et al., "Expression and localization of cytosolic sulfotransferase (SULT) 1A1 and SULT1A3 in normal human brain," *Drug metabolism and disposition: the biological fate of chemicals* 37, 706-709 (2009).
Pronk, et al., "GROMACS 4.5: a high-throughput and highly parallel open source molecular simulation toolkit," Bioinformatics, vol. 29, No. 7, pp. 845-854 (2013).
Schmitz, "Molecular dynamics with weighted time-averaged restraints for a DNA octamer. Dynamic interpretation of nuclear magnetic resonance data," *J Mol Biol* 234, 373-389 (1993).
Liu, et. al. "AlzPlatform: An Alzheimer's Disease Domain-Specific Chemogenomics Knowledgebase for Polypharmacology and Target Identification Research," *J. Chem. Inf. Model.* 54, 1050-1060 (2014).
Solomon, "Relaxation Processes in a System of Two Spins," *Phys Rev.* 99, 559-566 (1955).
Souery, et al., "Treatment resistant depression: methodological overview and operational criteria," *Eur Neuropsychopharmacol* 9, 83-91 (1999).
Sternbach H. "The serotonin syndrome." *Am J Psychiatry*, 148(6), 705-713 (1991).

(56) References Cited

OTHER PUBLICATIONS

Strott, "Sulfonation and molecular action," *Endocr Rev* 23, pp. 703-732 (2002).
Sun, et al., "The human estrogen sulfotransferase: a half-site reactive enzyme," *Biochemistry* 49, pp. 4779-4785 (2010).
Suominen, "Determination of Serotonin and Dopamine Metabolites in Human Brain Microdialysis and Cerebrospinal Fluid Samples by UPLC-MS/MS: Discovery of Intact Glucuronide and Sulfate Conjugates," *PLoS One* 8, e68007, 9 pages (2013).
Tang, et al., "Precise, facile initial rate measurements," *J Phys Chem B* 114, 16131-16136 (2010).
Thomas, et al., "Combination therapy with monoamine oxidase inhibitors and other antidepressants or stimulants: strategies for the management of treatment-resistant depression," *Pharmacotherapy* 35, 433-449 (2015).
Van Der Spoel, et al., "GROMACS: fast, flexible, and free," *J Comput Chem* 26, 1701-1718 (2005).
Wang, et al., "A Fast QM/MM (Quantum Mechanical/Molecular Mechanical) Approach to Calculate Nuclear Magnetic Resonance Chemical Shifts for Macromolecules," *J Chem Theory Comput* 2, 209-215 (2006).
Wang, et al., Development and testing of a general amber force field. *J Comput Chem* 25, 1157-1174 (2004).
Wang, et al., The Design and Interpretation of Human SULT1A1 Assays. *Drug Metab Dispos* 44, pp. 481-484 (2015).
Wang, et al., "3'-Phosphoadenosine 5'-phosphosulfate allosterically regulates sulfotransferase turnover," *Biochemistry* 53, 6893-6900 (2014).
Wang, et al., "Isozyme Specific Allosteric Regulation of Human Sulfotransferase 1A1," *Biochemistry* 55, 4036-4046 (2016).
Wang, et al., "The NSAID allosteric site of human cytosolic sulfotransferases," *J Biol Chem* 292, 20305-20312 (2017).
Wang, et al., "Paradigms of sulfotransferase catalysis: the mechanism of SULT2A1," *J Biol Chem* 289, 26474-26480 (2014).
Wang, et. al., "In Silico Prediction of Blood-Brain Barrier Permeability of Compounds by Machine Learning and Resampling Methods," *ChemMedChem*. 13, 2189-2201 (2018).
Whiteley, "Enzyme kinetics: partial and complete non-competitive inhibition," *Biochemical Education* 27, 15-18 (1999).
Yamada, et al., "Clinical pharmacology of MAO inhibitors: safety and future," *Neurotoxicology*, 25(1-2), 215-221 (2004).
Yamamoto, et al., "Determination of dopamine-3- and 4-O-sulphate in human plasma and urine by anion-exchange high-performance liquid chromatography with fluorimetric detection," *J Chromatogr* 342, 261-267 (1985).
Zou, et al., "Dopamine-induced SULT1A3/4 promotes EMT and cancer stemness in hepatocellular carcinoma," *Tumor Biology*, pp. 1-10 (2017).

\* cited by examiner

A.

B.

C.

Compound 12 = 3.0 or 0 μM

Compound 12 = Yellow, and protein is orange

Compound 23 = Cyan, and protein is blue

SMALL MOLECULE INHIBITION OF SULFOTRANSFERASE SULT1A3

CROSS-REFERENCE TO RELATED APPLICATIONS

This application is the U.S. National Stage of International Patent Application No. PCT/US2019/065442, filed Dec. 10, 2019, which claims priority from U.S. Provisional Patent Application No. 62/777,644, filed Dec. 10, 2018, which are incorporated herein by reference in their entirety.

FEDERAL FUNDING STATEMENT

This invention was made with government support under GM112728, GM121849, GM106158 and GM127144 awarded by the NIH. The government has certain rights in the invention.

BACKGROUND

It is estimated that one-in-five individuals worldwide will suffer from Major Depression (MD)—a depressive episode lasting at least two weeks (1). Suicide is the tenth leading cause of death in the US, and occurs ~20-fold more frequently during MD episodes (2). MD is treated primarily with serotonin-reuptake and monoamine oxidase inhibitors (3), which increase synaptic levels of serotonin. More than 40% of patients fail to respond when taking these antidepressants alone, but can respond well when taken in combination (4-6). The serotonin in brain micro-dialysates from living humans is nearly 100% oxidized by monoamine oxidase, and approximately 80% sulfonated (7). Thus, preventing sulfotransferase (SULT) activity in a monoamine-oxidase inhibited background can be expected to substantially enhance serotonin activity. Similarly compelling disease-relevant scenarios surround the sulfonation of other catecholamines; yet, to our knowledge, regulating sulfonation remains largely unexplored as a therapeutic strategy.

SULT1A3 shows a strong preference over other human SULT isoforms for the sulfonation of catecholamines (8,9). The enzyme is unique to higher primates (10) and is found at high levels in gut, platelets and brain (11-13). Sulfonation prevents catecholamines from binding their receptors (14) and enhances their transport properties (15,16) which decreases their terminal half-lives (17). SULT1A3 has recently been shown to harbor two allosteric sites through which it communicates with catecholamine biosynthetic-pathway metabolites (18,19). An allostere that did not bind either site but inhibited with high-affinity and isoform specificity. It is presented herein the structure of that allostere bound to SULT1A3 and demonstrate that the allostere slows turnover by stabilizing the enzyme's active-site cap—a conserved stretch of ~30 residues that is intimately involved in SULT substrate selection and turnover. A computational method that predicts the effects of inhibitors on cap stabilization is developed and used to design inhibitors with varying degrees of stabilization. The inhibitors were synthesized—these are the first man-made, isoform-specific allosteric SULT inhibitors—they bound tightly and their inhibition characteristics correlated remarkably well with the predicted values. Thus, the behavior of this small, catalytically important active-site cap is predictable and can be reliably incorporated into SULT1A3 inhibitor designs.

However, there remains a need for the identification of additional allosteric sites in SULT1A3 with high-affinity and isoform specificity. Furthermore, there is a need for isoform-specific allosteric SULT inhibitors.

SUMMARY OF THE DISCLOSED SUBJECT MATTER

The present invention is directed to compound having the structure of formula (I):

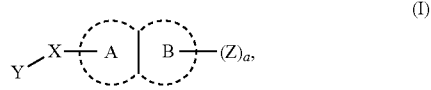

or a pharmaceutically acceptable salt thereof, wherein A and B are fused rings, each independently an aryl or heteroaryl ring; X is selected from a bond and an optionally substituted alkyl, alkene or alkyne; Y is selected from —OR', —NR'$_2$, —OCON'R'$_2$, —SO$_2$R', —NR'SO$_2$R', —NR'COR', —NR'SO$_2$NR'$_2$, —COOR', —NR'COOR', —NR'CONR'$_2$, and —NRC(NR')NR'$_2$, optionally substituted heteroaryl, and optionally substituted heterocycle; R' is H or an optionally substituted alkyl, alkene, alkyne, aryl or heteroaryl; Z is independently selected from H, optionally substituted alkyl, alkene or alkyne, and —X—Y, wherein two Z can together form an optionally substituted cycloalkyl, heterocycle, aryl, or heteroaryl; and a is 0 or an integer of 1-4, wherein the compound binds to an allosteric CMP8-binding site of SULT1A3.

In some embodiments,

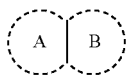

contains 1, 2, or 3 ring heteroatoms selected from N, O and S. In some embodiments,

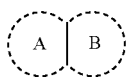

is a naphthalene, a naphthyridine, a pyridopyrimidine, a pyrimidopyrimidine, a pteridine, a quinazoline, a cinnoline, a quinoline, an isoquinoline, a phthalazine or a quinoxaline. In some embodiments, X is a $C_1$-$C_2$ alkyl chain. In some embodiments, Y is —CONR'$_2$ or —COOR' or optionally substituted triazole. In some embodiments, Z is a $C_3$-$C_6$ alkyl, alkenyl or alkynyl chain. 7. The compound of any of claims 1 to 5, wherein two Zs together form a substituted cyclohexanone, cyclohexene, or cyclohexanone. In some embodiments, Z is —X—Y. In some embodiments, a is 1 or 2. In some embodiments, the binding to the allosteric pocket of SULT1A3 is signified by enzymatic activity in a 1-hydroxypyrene (1-HP) assay.

Other embodiments include a compound having the structure of formula (II):

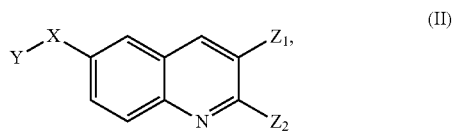

or a pharmaceutically acceptable salt thereof, wherein X is selected from a —$C_0$-$C_6$ alkyl or a —$C_2$-$C_6$ alkene; Y is selected from —OR', —COOR', —CONR'$_2$, and heteroaryl; R' is selected from H, alkyl, alkenyl, alkynyl, and aryl (e.g., H or $C_1$-$C_6$ alkyl); $Z_1$ is selected from H and —OR'; and $Z_2$ is selected from H, —$C_1$-$C_6$ alkyl, and —$C_0$-$C_6$—COOR', or $Z_1$ and $Z_2$ together form a substituted cycloalkyl, wherein when $Z_1$ and $Z_2$ are both H, then Y is heteroaryl, wherein the compound binds to an allosteric CMP8-binding site of SULT1A3.

In some embodiments, X is a $C_1$-$C_2$ alkelene. In some embodiments, Y is —CONR'$_2$. In some embodiments, Y is —COOR'. In some embodiments, Y is an optionally substituted triazole. In some embodiments, $Z_1$ is H and $Z_2$ is a $C_3$-$C_6$ alkyl. In some embodiments, $Z_1$ and $Z_2$ together form a substituted cyclohexanone. In some embodiments, the compound is selected from those in table A.

Other embodiments include a compound having the structure of formula (III):

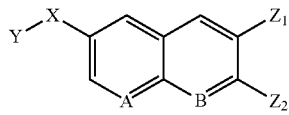

(III), or a pharmaceutically acceptable salt thereof, wherein A and B are each N or CH, and at least one of A and B is N; X is selected from a —$C_0$-$C_6$ alkylene or a —$C_2$-$C_6$ alkene; Y is selected from —OR', —COOR', —CONR'$_2$, and heteroaryl; R' is selected from H, alkyl, alkenyl, alkynyl, and aryl (e.g., H or $C_1$-$C_6$ alkyl); $Z_1$ is selected from H and —OR'; and $Z_2$ is selected from H, —$C_1$-$C_6$ alkyl, and —$C_0$-$C_6$—COOR', or $Z_1$ and $Z_2$ together form a substituted cycloalkyl, wherein when $Z_1$ and $Z_2$ are not both H.

In some embodiments of formula (III), $Z_1$ is H and $Z_2$ is a —$C_1$-$C_6$ alkyl. In some embodiments of formula (III), $Z_2$ is a —$C_1$-$C_4$ alkyl. In some embodiments of formula (III), X—Y is represented by Formula (A):

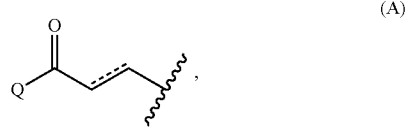

wherein Q is selected from —OR' or —NR'$_2$, and the dashed line represents an optional double bond. In some embodiments of formula (III), A is N and B is CH. In some embodiments of formula (III), A is CH and B is N. In some embodiments of formula (III), A and B are each N.

Other embodiments include a compound having the structure of formula (IV):

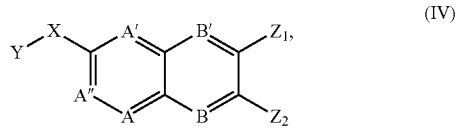

wherein A, A', A", B, and B' are selected from N or CR"; R" is selected from H, F, alkyl, alkenyl, alkynyl, and aryl; and X, Y $Z_1$, and $Z_2$ are the same as in Formula (III). In some embodiments, one of A, A', and A" is N and one of B, and B' is N, and the remaining of A, A', A", B, and B' are CR". In some embodiments, one of A, A', and A" is N or one of B, and B' is N, and the remaining of A, A', A", B, and B' are CR".

Other embodiments include a pharmaceutical composition comprising a compound of the disclosure and a pharmaceutically acceptable carrier.

Other embodiments include a method inhibiting SULT1A3 in a subject in need thereof, comprising administering a compound of the disclosure to the patient. In some embodiments, the subject is a human. Other embodiments include a method inhibiting SULT1A3 in a cell, comprising contacting a cell with a compound of the disclosure. In some embodiments, the cell is a mammalian cell. In some embodiments, the mammal is a human.

Other embodiments include a method of inhibiting the activity of SULT1A3, comprising providing a SULT1A3 enzyme, and contacting the SULT1A3 enzyme with a compound of the disclosure. In some embodiments, the contacting of SULT1A3 is performed in vitro. In some embodiments, the contacting of SULT1A3 is performed in vivo.

Other embodiments include a method of prolonging therapeutic efficacy of a catecholic drug or lowering the effective concentration of a catecholic drug in a patent, comprising administering a compound of the disclosure. Other embodiments include a method of preventing metabolization of dopamine in a patient comprising administering a compound of the disclosure. Other embodiments include a method of retarding tumor progression of hepatocellular carcinoma in a patient comprising administering a compound of the disclosure.

BRIEF DESCRIPTION OF DRAWINGS

FIG. 2A shows the structure and 600-MHz $^1$H-NMR spectrum of CMP8. The protons of CMP8 are labelled in the spectrum and structure. Red labels identify the proton positions used in NMR-distance measurements. Conditions: CMP8 (1.9 mM), DMSO (0.50 mM), TMS (0.50 mM), D$_2$O (>95%), 25±1° C.

FIG. 2B shows spin-label effects on the H5-proton peak of CMP8. The solution $^1$H-NMR spectrum (600 MHz) of the H5-peak of CMP8 is shown as a function of percent CMP8 bound to spin-labelled C234-SULT1A3. Peak amplitudes were normalized to reflect 1.0 mM of CMP8. Conditions: CMP8 (1.0 mM (purple), 400 μM (green), 200 μM (blue), 100 μM (red)), spin-labelled C234-SULT1A3 (20 μM, active site), PAP (500 μM, 17×$K_d$), KPO$_4$ (50 mM), pD 7.4, 25±1° C. Conditions associated with the black and purple peaks were identical except that the black-spectrum conditions lacked enzyme. CMP8 is saturating at all concentrations (i.e., ≥2300 $K_d$). FIG. 2C shows line width vs fraction inhibitor bound. The effects of paramagnetic spin labels (4-maleimido-PROXYL attached at C234 (red), C198

(black) or C116 (blue)) and diamagnetic control (N-cyclohexylmaleimide attached at C234 (green)) on the linewidth of the H5-proton peak plotted as a function of fraction of enzyme-bound CMP8. Fractions of CMP8 bound: 0.02, 0.05, 0.10, 0.20. Conditions are as described in FIG. 2B. Diamagnetic controls for C198 and C116 were indistinguishable from the C234.

Figure 3:
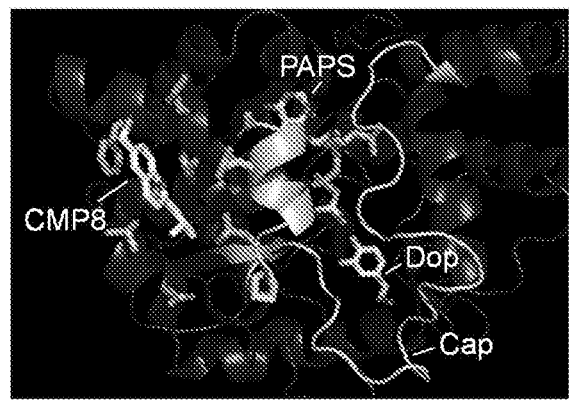
Figure 3:
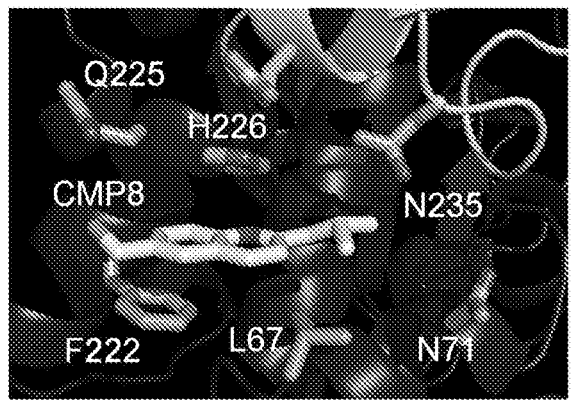

FIG. 3 shows structure of the CMP8•SULT1A3•PAPS•Dopamine Complex. FIG. 3A shows the structure at a distance. CMP8 is labeled and shown in white. Carbon atoms of residues in direct contact with CMP8 are blue. The cap (orange) is shown in the closed conformation and sitting above the substrates, PAPS and dopamine (Dop). FIG. 3B shows the CMP8-binding pocket. CMP8 is shown interacting with six direct-contact residues, shown in blue. The refined structure (shown) was generated by MD energy minimization of the NMR-distance-constrained structure.

Figure 4:
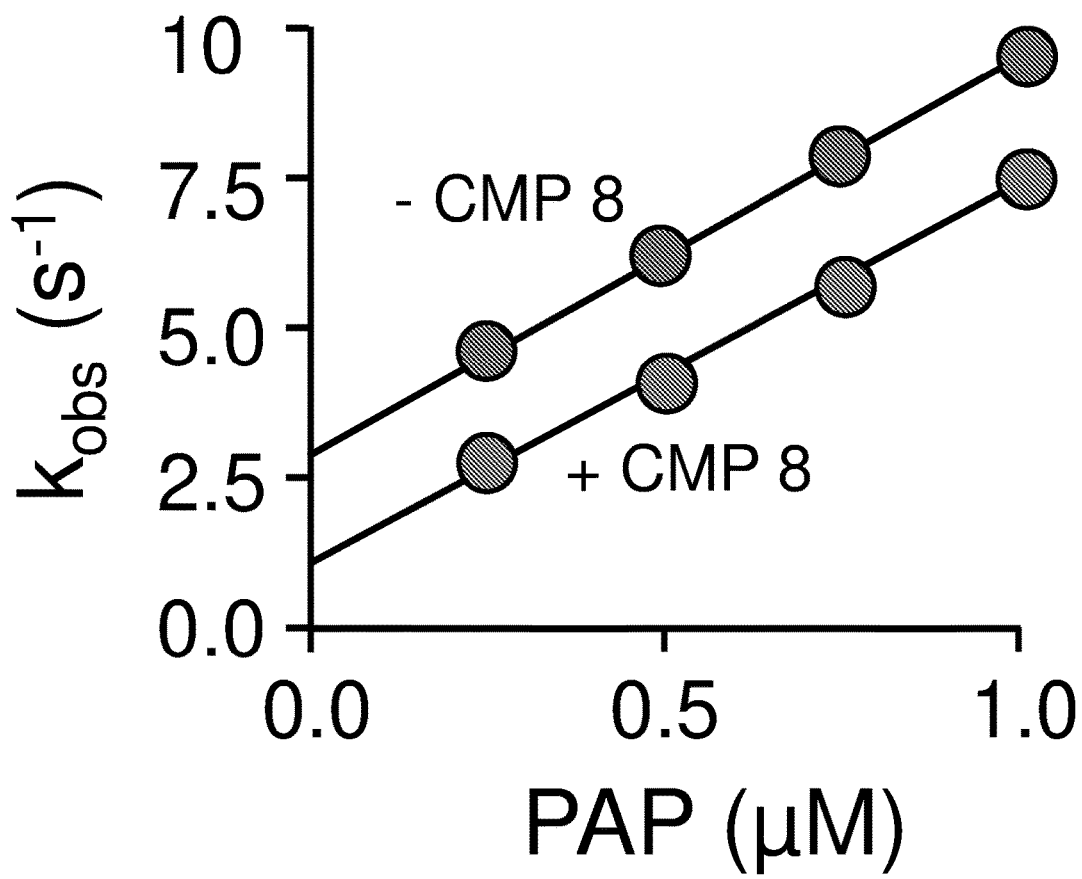

FIG. 4 shows the mechanism of inhibition. The effect of CMP8 on PAP binding to SULT1A3 was monitored using a stopped-flow spectrofluorimeter ($\lambda_{ex}$=290 nm, $\lambda_{em}$≥330 nm (cutoff filter)). Reactions were initiated by rapidly mixing (1:1 v/v) a solution containing SULT1A3 (25 nM, dimer), CMP8 (0 (blue) or 1.7 µM, 50×$K_d$ (red)), $KPO_4$ (50 mM), pH 7.5, 25±2° C., with a solution that was identical except that it lacked SULT1A3 and contained PAP at twice the indicated concentrations. $k_{obs}$ values were obtained by fitting the average of 6-9 progress curves to a single exponential. Each $k_{obs}$ value was determined in triplicate and the averaged values are shown. $k_{on}$ and $k_{off}$ are given, respectively, by the slopes and intercepts obtained from linear least-squares fitting of the $k_{obs}$ vs [PAP] plots.

Figure 5:
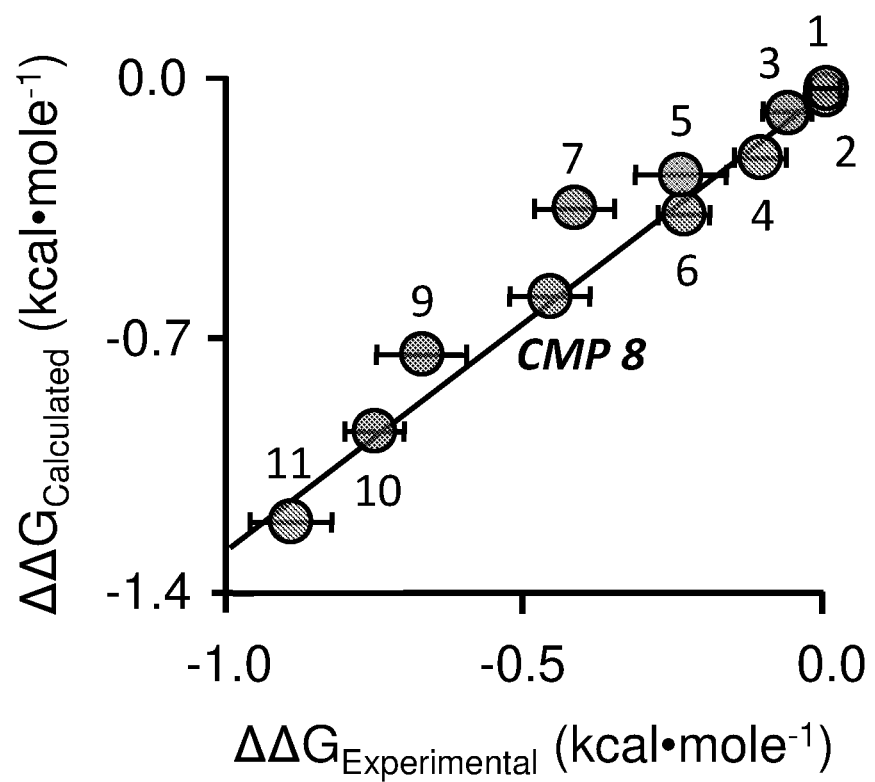

FIG. 5 shows a free energy correlation plot. DDG values were either calculated ab initio, using MD simulations, or obtained from experimentally determined $k_{cat}$ values. The data show strong linear correlation, slope=1.2±0.1. Numbers associated with data points correspond to the compound numbering in Table A. Error bars indicate ±one standard unit. Error in the calculated (y-axis) values is vanishingly small.

Figure 6:
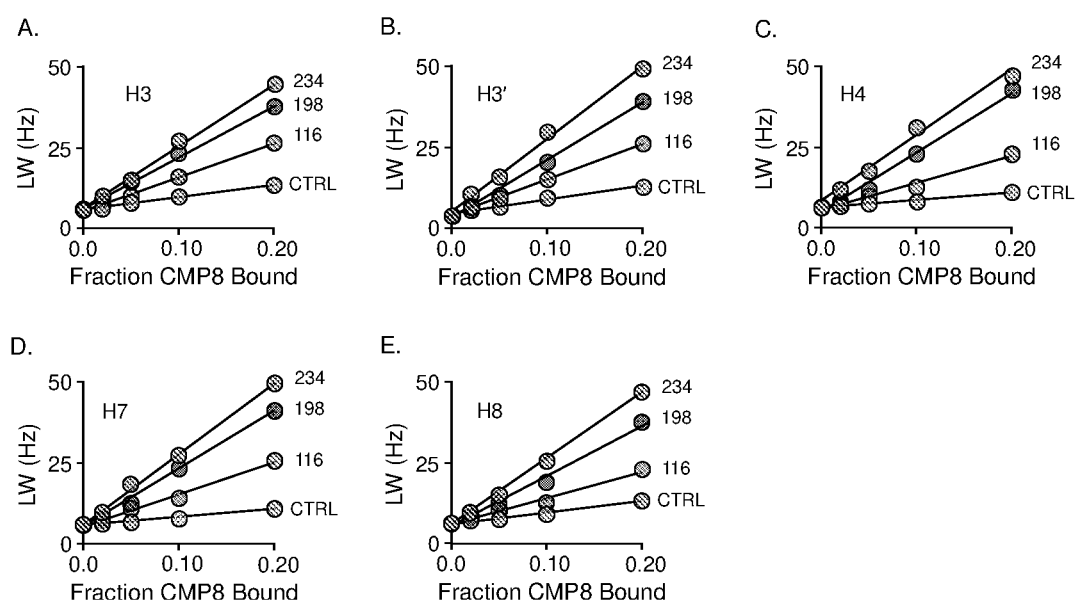

FIG. 6 shows CMP8-Proton Line-Width vs Fraction CMP8 Bound. The effects of paramagnetic spin label (4-maleimido-PROXYL) attached at C234 (red), C198 (black) or C116 (blue) and diamagnetic control (N-cyclohexylmaleimide) attached at C234 (green) on the linewidth of CMP8 solution $^1$H-NMR peaks plotted as a function of fraction of enzyme-bound CMP8. Panels A, B, C, D and E are associated with CMP8 protons H3, H3', H4, H7 and H8, respectively. Conditions: spin-labelled SULT1A3 (20 µM, active sites), CMP8 (100-1000 µM), PAP (500 µM, 17×$K_d$), $KPO_4$ (50 mM), pD 7.4, 25±1° C.

Figure 7:
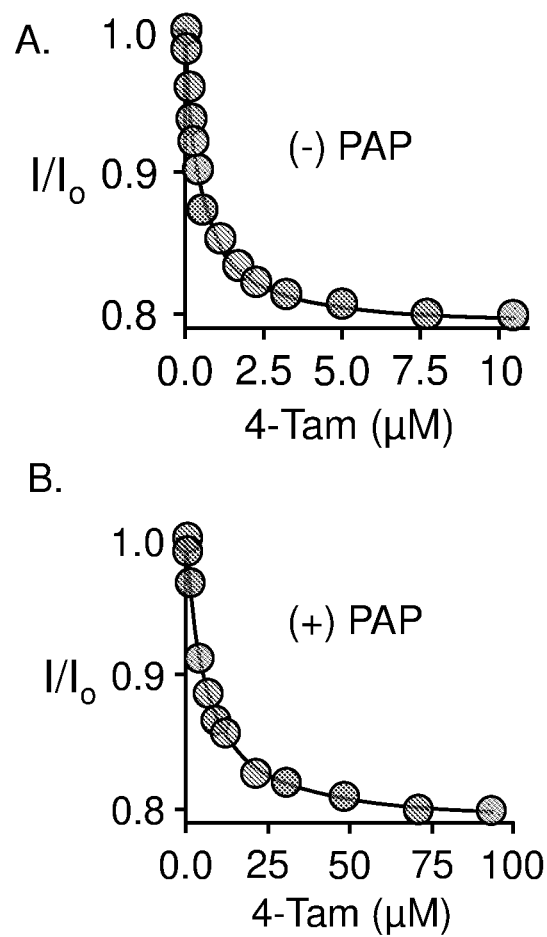

FIG. 7 shows 4-Hydroxytamoxifen (4-Tam) binding to SULT1A3. 4-Tam binding affinities were determined in the absence and presence of saturating PAP. Binding was monitored via ligand-induced changes in SULT1A3 intrinsic florescence ($\lambda_{ex}$=290 nm, $\lambda_{em}$=340 nm). Fluorescence intensities are normalized relative to [4-Tam]=0. Each data-point is the average of two independent determinations. Conditions: SULT (150 nM, active sites), PAP (0 or 0.50 mM), $KPO_4$ (50 mM), pH 7.5, 25±2° C. The line through the data represents the least-squares best fit to a model that assumes a binding stoichiometry of one 4-Tam per subunit. $K_{d\ (-PAP)}$=0.41 (0.03) M; $K_{d\ (+PAP)}$=5.4 (0.3) µM.

Figure 8:
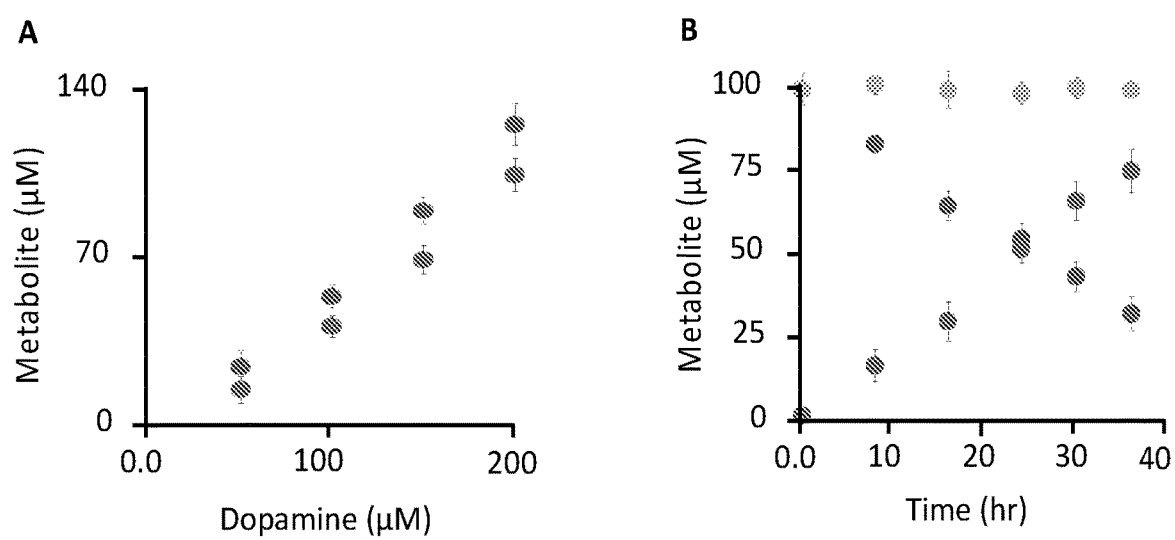

FIG. 8 shows the concentration dependence of dopamine sulfonation by human mammary epithelial cells (HME cells) that express SULT1A3. FIG. 8A shows HME cells were incubated for 24 hours with dopamine (at the indicated concentrations) at which time the levels of dopamine (red dots) and dopamine sulfate (blue dots) were determined (as described in the FIG. 10). FIG. 8B shows a time course of dopamine sulfonation by SULT1A3 (+) and (−) HME cells. Cells were incubated with 100 µM dopamine and incubation media was sampled for dopamine and dopamine sulfate at the indicated time intervals. The dopamine and dopamine sulfate levels in the SULT1A3 (+) strain are shown as red and blue dots, respectively. Only dopamine (green dots) was detected using the SULT1A3 (−) strain. These experiments demonstrate that dopamine sulfonation by HME cells is SULT1A3 dependent and establish assay conditions.

Figure 9:
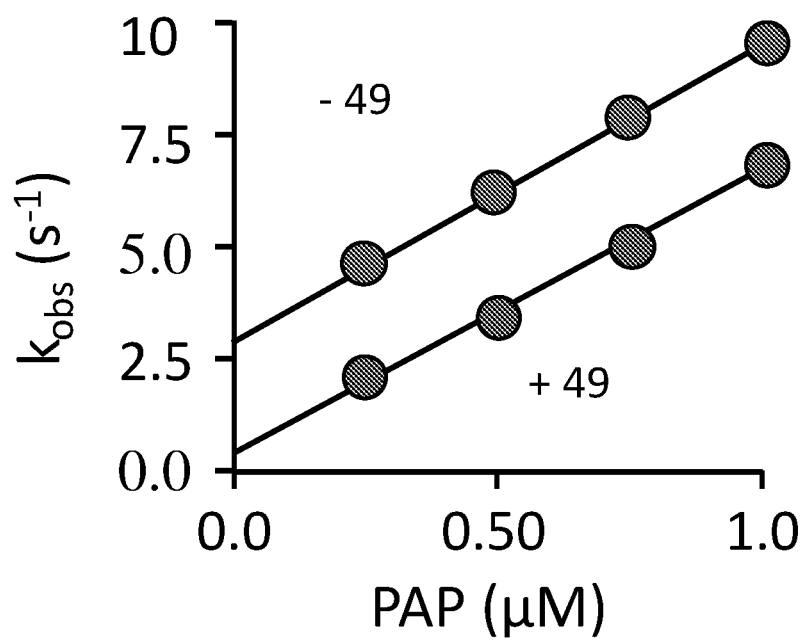

FIG. 9 confirms the mechanism of Compound 12 inhibition. Compound 12 is hypothesized to inhibit SULT1A3 by stabilizing the cap-closed conformation of the enzyme's active site. This hypothesis was validated by determining the microscopic rate constants for PAPS binding and release in the presence (red, lower "+49") and absence (blue, upper "−49") of Compound 12. Binding was monitored via changes in enzyme intrinsic fluorescence.

Figure 10:
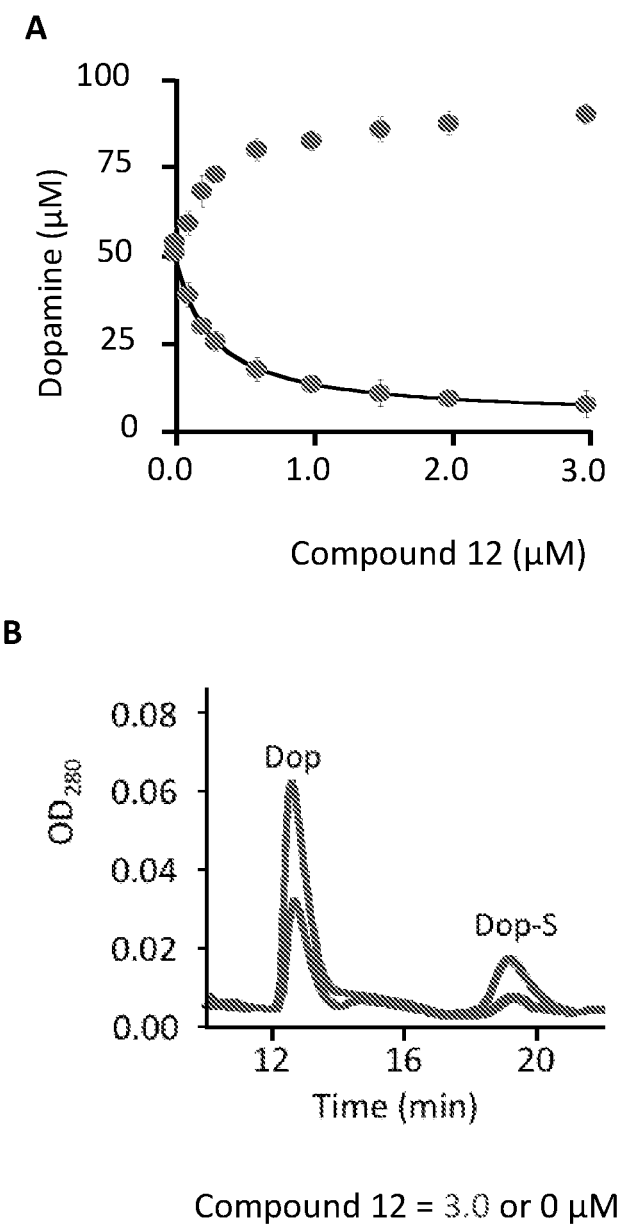

FIG. 10 shows the inhibition of dopamine sulfonation by Compound 12. FIG. 10A shows the inhibition of dopamine sulfonation by SULT1A3-expressing HME cells as a function of the concentration of Compound 12. HME cells were incubated with dopamine (100 µM) and Compound 12 (at the indicated concentrations) for 24 hours at which time the dopamine (red dots) and dopamine sulfate (blue dots) levels were determined. The best-fit titration curve (seen as a black line passing through the data points) predicts an $EC_{50}$ of 250±87 nM for Compound 12 with 83 inhibition at saturation. FIG. 10B shows the HPLC profiles used to quantitate the dopamine and dopamine sulfate levels associated with the 0 and 3.0 µM Compound 12 data points seen in FIG. 10A. The chromatography was performed using a PFP-HPLC column. Panel 10A demonstrates that Compound 12 potently inhibits SULT1A3 activity in a human cell line. Further, the data in Table A reveal that Compound 12 is highly specific for the SULT1A3 isoform. Collectively, these findings suggest that Compound 12 may prove a potent and selective agent to prevent dopamine conjugation in brain.

Figure 11:
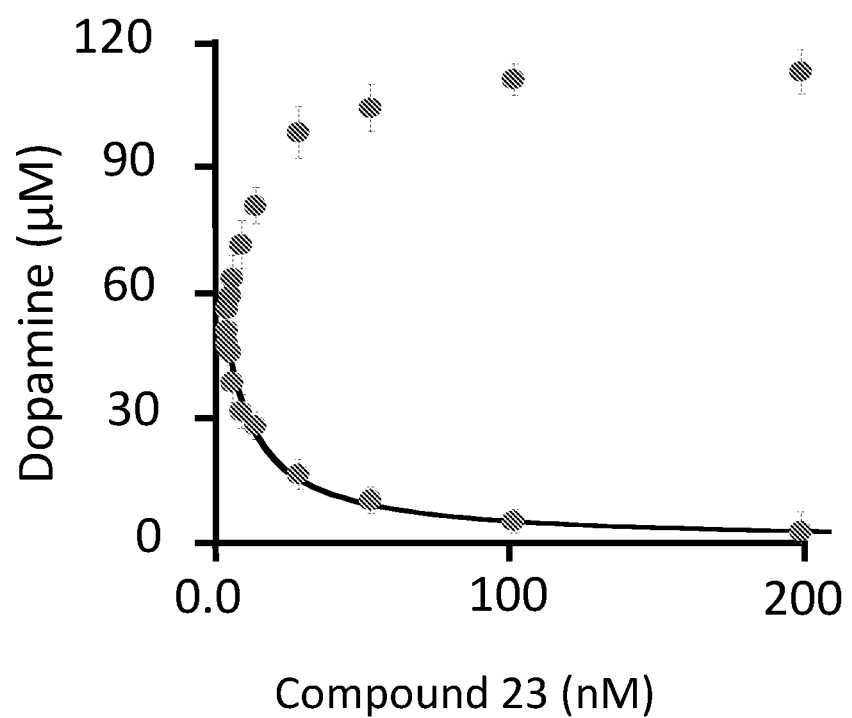

FIG. 11 shows inhibition of SULT1A3 by Compound 23. HME cells expressing SULT1A3 were incubated for 24 hours with dopamine (100 µM) and Compound 23 (at the indicated concentrations) at which time the dopamine (red dots) and dopamine sulfate (blue dots) concentrations were determined using the methods associated with FIG. 10B. Experiments were performed in triplicate and the best-fit titration curve (shown as a black line passing through the data points) predicts an $EC_{50}$ of 11±87 nM for Compound 12 with essentially complete inhibition at saturation.

Figure 12:
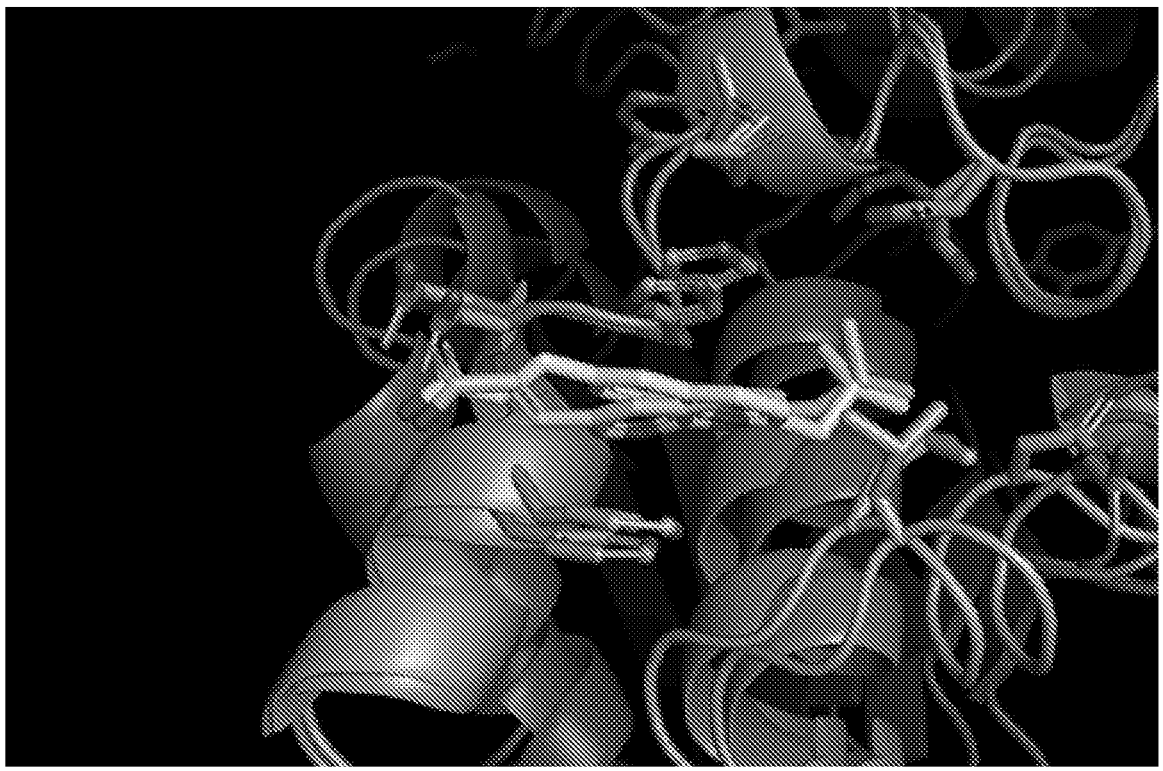

FIG. 12 shows the molecular-dynamics predicted structures of Compounds 12 and 23 bound to SULT1A3 predicted. The compounds are seen interacting directly with the active-site cap of SULT1A3. The π-stacking interactions between the SULT1A3 aromatic residues (F222 and H226) and the quinolone and naphthyridine scaffolds of Compound 12 and 23, respectively, confer the high specificity of the inhibitors for SULT1A3.

DETAILED DESCRIPTION

1. Compounds of the Disclosure

Compounds of the present disclosure include novel compounds having the structure of formula (I):

(I)

or a pharmaceutically acceptable salt thereof, wherein
A and B are fused rings, each independently an aryl or heteroaryl ring;
X is selected from a bond and an optionally substituted alkyl, alkene or alkyne;
Y is selected from —OR', —NR'$_2$, —OCON'R'$_2$, —SO$_2$R', —NR'SO$_2$R', —NR'COR', —NR'SO$_2$NR'$_2$, —COOR', —NR'COOR', —NR'CONR'$_2$, and —NRC(NR')NR'$_2$, optionally substituted heteroaryl, and optionally substituted heterocycle;
R' is H or an optionally substituted alkyl, alkene or alkyne;
Z is independently selected from H, optionally substituted alkyl, alkene or alkyne, and —X—Y, wherein two Z can together form an optionally substituted cycloalkyl, heterocycle, aryl, or heteroaryl; and
a is 0 or an integer of 1-4,
wherein the compound binds to an allosteric CMP8-binding site of SULT1A3.

In some embodiments,

contains 1, 2, or 3 ring heteroatoms selected from N, O and S. In some embodiments, A-B is a 6,6, a 5,6, or a 6,5 fused ring. In some embodiments, it is a naphthalene, a naphthyridine, a pyridopyrimidine, a pyrimidopyrimidine, a pteridine, a quinazoline, a cinnoline, a quinoline, an isoquinoline, a phthalazine or a quinoxaline. In some embodiments, X is a C$_1$-C$_2$ alkyl chain. In some embodiments, Y is —CONR'$_2$ or —COOR' or optionally substituted triazole. In some embodiments, Z is a C$_3$-C$_6$ alkyl, alkenyl or alkynyl chain. In some embodiments, two Zs together form a substituted cyclohexanone, cyclohexene, or cyclohexanone. In some embodiments, Z is —X—Y. In certain embodiments, a is 1, 2, 3 or 4. In some embodiments, the binding to the allosteric pocket of the CMP8-binding site of SULT1A3 is signified by enzymatic activity in a 1-hydroxypyrene (1-HP) assay, e.g., an assay as described herein.

Compounds of the present disclosure include novel compounds of formula (II)

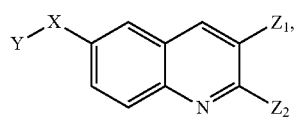
(II)

or a pharmaceutically acceptable salt thereof, wherein

X is selected from a —C$_0$-C$_6$ alkylene or a —C$_2$-C$_6$ alkene;
Y is selected from —OR', —COOR', —CONR'$_2$, and heteroaryl;
R' is H or C$_1$-C$_6$ alkyl;
Z$_1$ is selected from H and —OR'; and
Z$_2$ is selected from H, —C$_1$-C$_6$ alkyl, and —C$_0$-C$_6$—COOR', or
Z$_1$ and Z$_2$ together form a substituted cycloalkyl,
wherein when Z$_1$ and Z$_2$ are both H, then Y is heteroaryl.

In some embodiments, the compound of formula (II) binds to an allosteric CMP8-binding site of SULT1A3. In some embodiments, X is a C$_1$-C$_2$ alkylene. In some embodiments, Y is —CONR'$_2$. In some embodiments, Y is —COOR'. In some embodiments, Y is an optionally substituted triazole. In some embodiments, Z$_1$ is H and Z$_2$ is a C$_3$-C$_6$ alkyl. In some embodiments, Z$_1$ and Z$_2$ together form a substituted cyclohexanone.

Compounds of the present disclosure include compounds of formula (III)

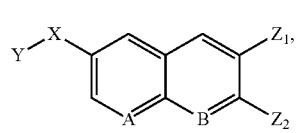
(III)

or a pharmaceutically acceptable salt thereof, wherein
A and B are each N or CH, and at least one of A and B is N;
X is selected from a —C$_0$-C$_6$ alkylene or a —C$_2$-C$_6$ alkene;
Y is selected from —OR', —COOR', —CONR'$_2$, and heteroaryl;
R' is selected from H, alkyl, alkenyl, alkynyl, and aryl (e.g., H or C$_1$-C$_6$ alkyl);
Z$_1$ is selected from H and —OR'; and
Z$_2$ is selected from H, —C$_1$-C$_6$ alkyl, and —C$_0$-C$_6$—COOR', or
Z$_1$ and Z$_2$ together form a substituted cycloalkyl,
wherein when Z$_1$ and Z$_2$ are not both H.

In some embodiments, the compound of formula (III) binds to an allosteric CMP8-binding site of SULT1A3. In some embodiments of the compound of formula (II) or (III), Z$_1$ is H and Z$_2$ is a —C$_1$-C$_6$ alkyl. In some embodiments, Z$_2$ is a —C$_1$-C$_4$ alkyl (e.g., a C$_4$ alkyl). In some embodiments, X—Y is represented by Formula (A):

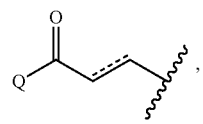
(A)

wherein Q is selected from —OR' or —NR'$_2$, and the dashed line represents an optional double bond. In some embodiments, Q is selected from OH and NH$_2$. In some embodiments, A is N and B is CH or A is CH and B is N or A and B are each N.

Compounds of the present disclosure include compounds having the structure of formula (IV):

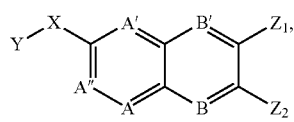
(IV)

wherein A, A', A", B, and B' are selected from N or CR"; R" is selected from H, F, alkyl, alkenyl, alkynyl, and aryl; and X, Y $Z_1$, and $Z_2$ are the same as in Formula (III). In some embodiments, one of A, A', and A" is N and one of B, and B' is N, and the remaining of A, A', A", B, and B' are CR". In some embodiments, one of A, A', and A" is N or one of B, and B' is N, and the remaining of A, A', A", B, and B' are CR". For example, formula (IV) can have one of the following structures:

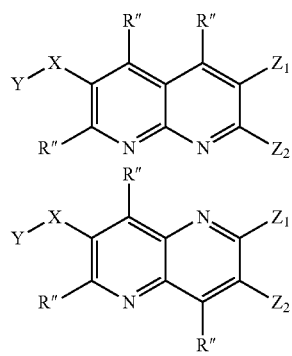

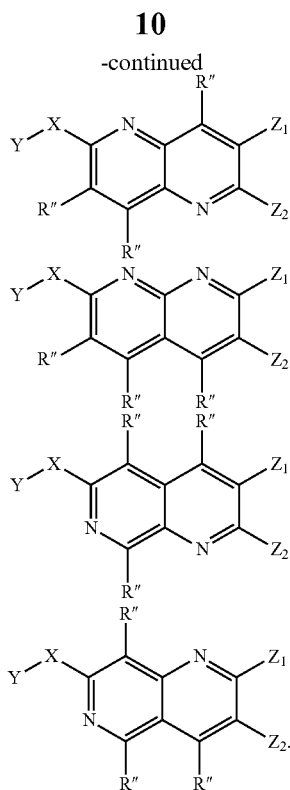

The present disclosure includes embodiments where one or more of the variable moieties of Formula (I), (II), (III) and/or (IV) are represented by the equivalent moiety of one or more of the compounds of Table A without requiring the other specific moieties of the same compound of Table A.

TABLE A

| Compound Number | Structure | SULT1A1[1,2] $K_i$/ μM | Enzyme Inhibition at Saturation/% | SULT1A3[1,2] $K_i$/μM | Enzyme Inhibition at Saturation/% |
|---|---|---|---|---|---|
| 1 | ![structure] | ND | ND | ND | ND |
| 2 | ![structure] | ND | ND | ND | ND |
| 1 | ![structure] | ND | ND | ND | ND |

TABLE A-continued

| Compound Number | Structure | SULT1A1[1,2] | | SULT1A3[1,2] | |
|---|---|---|---|---|---|
| | | Enzyme $K_i$/μM | Inhibition at Saturation/% | $K_i$/μM | Enzyme Inhibition at Saturation/% |
| 2 | 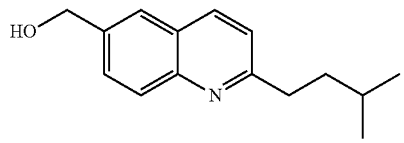 [SMILES: CC(C)CCc1ccc2cc(CO)ccc2n1] | ND | ND | ND | ND |
| 3 | 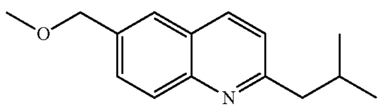 [SMILES: COCc1ccc2nc(CC(C)C)ccc2c1] | 5.7 | 10 | 6.1 (0.6) | 10 (1) |
| 4 | 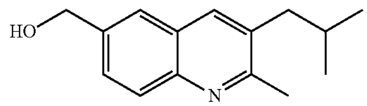 [SMILES: Cc1nc2ccc(CO)cc2cc1CC(C)C] | 7.7 (0.3) | 20 | 7.5 (0.5) | 17 (1) |
| 5 | 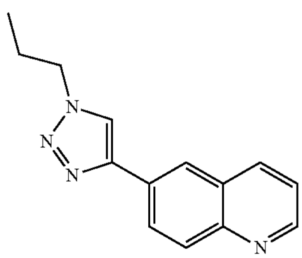 [SMILES: CCCn1cc(-c2ccc3ncccc3c2)nn1] | 4.7 (0.5) | 53 | 3.1 (0.4) | 33 (2) |
| 6 | 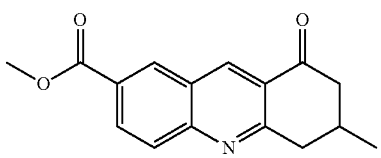 | ND | ND | 0.66 (0.05) | 35 (4) |
| 7 | 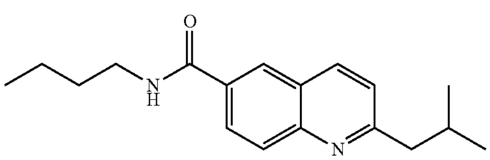 [SMILES: CCCCNC(=O)c1ccc2nc(CC(C)C)ccc2c1] | 5.1 (0.7) | 67 | 1.3 (0.2) | 51 (2) |
| 8 ("105") | 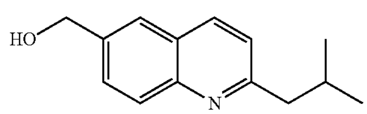 [SMILES: CC(C)Cc1ccc2cc(CO)ccc2n1] | ND | ND | 0.034 (0.003) | 54 (3) |
| 9 | 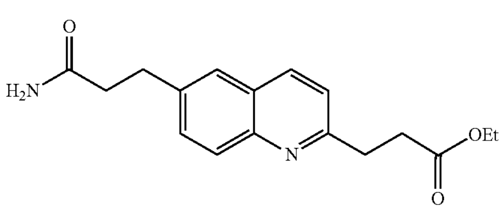 [SMILES: CCOC(=O)CCc1ccc2cc(CCC(N)=O)ccc2n1] | ND | ND | 0.33 (0.03) | 63 (3) |
| 1 | 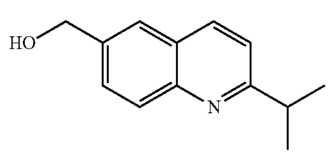 | ND | ND | ND | ND |

TABLE A-continued

| Compound Number | Structure | SULT1A1[1,2] | | SULT1A3[1,2] | |
|---|---|---|---|---|---|
| | | Enzyme $K_i$/μM | Inhibition at Saturation/% | $K_i$/μM | Enzyme Inhibition at Saturation/% |
| 2 | HO-quinoline-CH2OH with 2-isopentyl substituent | ND | ND | ND | ND |
| 10 | HOOC-CH=CH-quinoline | 22 | 30 | 4.1 (0.3) | 72 (4) |
| 11 | H2N-C(=O)-quinoline with 2-isobutyl | ND | ND | 0.86 (0.07) | 78 (4) |
| 12 | H2N-C(=O)-CH2CH2-quinoline with 2-isobutyl | ND | ND | 0.069 (0.004) | 83 (4) |
| 13 | H2N-C(=O)-CH=CH-quinoline with 2-isobutyl | 6.2 (0.7) | 48 (2) | 0.19 (0.02) | 65 (4) |
| 14 | HO-CH2-quinoline | ND | ND | ND | ND |
| 15 | MeO-C(=O)-quinoline with 2-isobutyl | ND | ND | ND | ND |
| 16 | OHC-quinoline with 2-isobutyl | ND | ND | ND | ND |
| 17 | Br-quinoline with 2-isobutyl | ND | ND | ND | ND |
| 18 | HO-CH2-quinoline with 2-neopentyl | 2.5 (0.1) | 40 | ND | ND |

TABLE A-continued

| Compound Number | Structure | SULT1A1[1,2] | | SULT1A3[1,2] | |
|---|---|---|---|---|---|
| | | $K_i$/μM | Enzyme Inhibition at Saturation/% | $K_i$/μM | Enzyme Inhibition at Saturation/% |
| 19 | butyl amide of quinoline-6-carboxamide | ND | ND | ND | ND |
| 1 | 6-(hydroxymethyl)-2-isopropylquinoline | ND | ND | ND | ND |
| 2 | 6-(hydroxymethyl)-2-isopentylquinoline | ND | ND | ND | ND |
| 20 | 7-(1-propyl-1H-1,2,3-triazol-4-yl)naphthalen-2-ol | 12.1 | 17 | 2.6 | 16 |
| 21 | 7-bromo-3-methyl-2,3,4,9-tetrahydroacridin-1-one | ND | ND | ND | ND |
| 22 | methyl 3-hydroxy-2-methylquinoline-6-carboxylate | ND | ND | ND | ND |
| 23 | (E)-3-(7-isobutyl-1,8-naphthyridin-3-yl)acrylamide | 3.1 (0.2) | 61 (3) | 0.0092 (0.0008) | 96 (2) |
| 24 | (E)-3-(7-isobutyl-1,8-naphthyridin-3-yl)acrylic acid | ND | ND | 3.1 (0.2) | 29.4 (3) |

TABLE A-continued

| Compound Number | Structure | SULT1A1[1,2] | | SULT1A3[1,2] | |
| --- | --- | --- | --- | --- | --- |
| | | $K_i$/μM | Enzyme Inhibition at Saturation/% | $K_i$/μM | Enzyme Inhibition at Saturation/% |
| 25 | (structure) | ND | ND | 0.017 (0.004) | 90 (5) |
| 26 | (structure) | ND | ND | ND | ND |
| 27 | (structure) | ND | ND | 0.11 (0.03) | 75 (5) |
| 28 | (structure) | ND | ND | 0.085 (0.005) | 52 (4) |

[1]ND, inhibition was not detected at 30 μM compound.
[2]Parentheses indicate one standard error.
ND compounds are comparative.

2. Methods of Treatment

The present disclosure also relates to methods of inhibiting SULT1A3. In some embodiments, the present disclosure also relates to methods of inhibiting targeting an allosteric site on SULT1A3 with an inhibitor, suh as a compound disclosed herein. For example, the methods include a method inhibiting SULT1A3 in a subject in need thereof, comprising administering a compound of the present disclosure. Other embodiments include a method inhibiting SULT1A3 in a cell, comprising contacting a cell with a compound of the present disclosure. In some embodiments, the cell is a mammalian cell (e.g., a human). In some embodiments, the subject is a human (e.g., an adult human).

Other embodiments include therapeutic methods, such as: a method of prolonging therapeutic efficacy of a catecholic drug or lowering the effective concentration of a catecholic drug in a patent, comprising administering a compound of the present disclosure; or a method of preventing metabolization of dopamine in a patient comprising administering a compound of the present disclosure; or a method of retarding tumor progression of hepatocellular carcinoma in a patient comprising administering a compound of the present disclosure.

Other methods of the disclosure include method of inhibiting the activity of SULT1A3, comprising providing a SULT1A3 enzyme, and contacting the SULT1A3 enzyme with a compound of the disclosure. This method may be in vitro or in vivo.

3. Pharmaceutical Formulations

For oral administration, liquid or solid dose formulations may be used. Some examples of oral dosage formulations include tablets, gelatin capsules, pills, troches, elixirs, suspensions, syrups, wafers, chewing gum and the like. The compounds can be mixed with a suitable pharmaceutical carrier (vehicle) or excipient as understood by practitioners in the art. Examples of carriers and excipients include starch, milk, sugar, certain types of clay, gelatin, lactic acid, stearic acid or salts thereof, including magnesium or calcium stearate, talc, vegetable fats or oils, gums and glycols.

For systemic, intracerebroventricular, intrathecal, topical, intranasal, subcutaneous, or transdermal administration, formulations of the compounds useful in the methods of the present technology may utilize conventional diluents, carriers, or excipients etc., such as are known in the art can be employed to deliver the compounds. For example, the formulations may comprise one or more of the following: a stabilizer, a surfactant (such as a nonionic, ionic, anionic, or zwitterionic surfactant), and optionally a salt and/or a buffering agent. The compound may be delivered in the form of a solution or in a reconstituted lyophilized form.

In some embodiments, the stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. In some embodiments, the stabilizer or combination of stabilizers constitutes from about 0.1% to about 10% weight for weight of the compound.

In some embodiments, the surfactant is a nonionic surfactant, such as a polysorbate. Some examples of suitable surfactants include polysorbates (e.g., Tween20, Tween80); a polyethylene glycol or a polyoxyethylene polyoxypropylene glycol, such as Pluronic F-68 at from about 0.001% (w/v) to about 10% (w/v).

A salt or buffering agent may be any salt or buffering agent, such as for example, sodium chloride, or sodium/potassium phosphate, respectively. In certain embodiments, the buffering agent maintains the pH of the pharmaceutical composition in the range of about 5.5 to about 7.5. The salt and/or buffering agent is also useful to maintain the osmolality at a level suitable for administration to a human or an animal. In some embodiments, the salt or buffering agent is present at a roughly isotonic concentration of about 150 mM to about 300 mM.

The formulations of the compounds useful in the methods of the present technology may additionally comprise one or more conventional additives. Some examples of such additives include a solubilizer such as, for example, glycerol; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

The mammal can be any mammal, including, for example, farm animals, such as sheep, pigs, cows, and horses; pet animals, such as dogs and cats; laboratory animals, such as rats, mice and rabbits. In one embodiment, the mammal is a human.

4. Definitions

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Hence, isotopically labeled compounds are within the scope of the invention.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched alkyl groups having from 1 to about 20 carbon atoms, and typically from 1 to 12 carbons or, in some embodiments, from 1 to 8, 1 to 6, or 1 to 4 carbon atoms. Alkyl groups further include cycloalkyl groups as defined below. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include mono-, bicyclic and polycyclic ring systems, such as, for example bridged cycloalkyl groups as described below, and fused rings, such as, but not limited to, decalinyl, and the like. In some embodiments, polycyclic cycloalkyl groups have three rings. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The substituent —CO₂H, may be replaced with bioisosteric replacements such as:

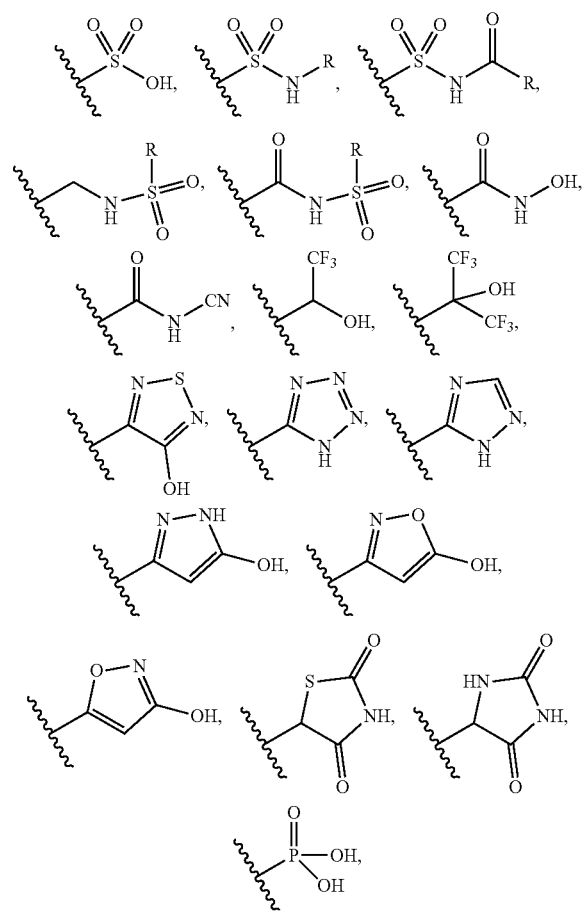

and the like, wherein R has the same definition as R' and R" as defined herein. See, e.g., THE PRACTICE OF MEDICINAL CHEMISTRY (Academic Press: New York, 1996), at page 203. The substituent —CONHR may be replaced with bioisosteric replacements such as: trifluoroethylamine,

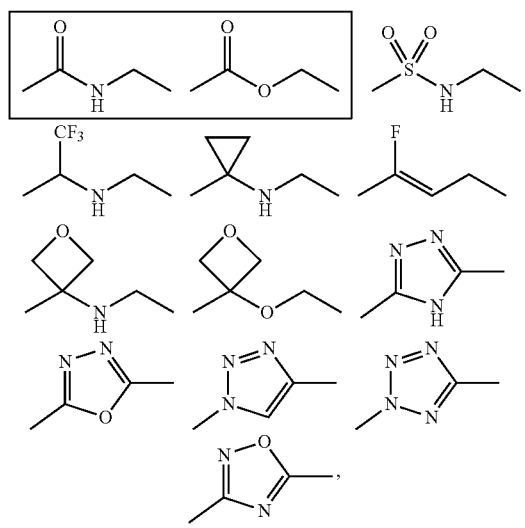

it would be understood that the ethyl moiety in the above figures may be changed to correspond to other R groups, as appropriate (e.g., H).

Those of skill in the art will appreciate that compounds of the invention may exhibit the phenomena of tautomerism, conformational isomerism, geometric isomerism and/or optical isomerism. As the formula drawings within the specification and claims can represent only one of the possible tautomeric, conformational isomeric, optical isomeric or geometric isomeric forms, it should be understood that the invention encompasses any tautomeric, conformational isomeric, optical isomeric and/or geometric isomeric forms of the compounds having one or more of the utilities described herein, as well as mixtures of these various different forms.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

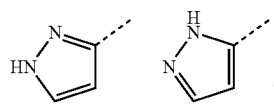

As readily understood by one skilled in the art, a wide variety of functional groups and other structures may exhibit tautomerism, and all tautomers of compounds as described herein are within the scope of the present invention.

Stereoisomers of compounds, also known as "optical isomers," include all chiral, diastereomeric, and racemic forms of a structure, unless the specific stereochemistry is expressly indicated. Thus, compounds used in the present invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these are all within the scope of the invention.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. and Drug administration.

By "patient" is meant any animal for which treatment is desirable. Patients may be mammals, and typically, as used herein, a patient is a human individual.

The term "pharmaceutically acceptable salt," as used herein, represents salts or zwitterionic forms of the compounds of the present invention which are water or oil-soluble or dispersible; which are suitable for treatment of diseases without undue toxicity, irritation, and allergic-response; which are commensurate with a reasonable benefit/risk ratio; and which are effective for their intended use. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form pharmaceutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

This disclosure is not limited to particular embodiments described, as such may, of course, vary. It is also to be understood that the terminology used herein is for the purpose of describing particular embodiments only, and is not intended to be limiting, since the scope of the present invention will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

5. Working Examples

The following examples are provided to illustrate the present invention. It should be understood, however, that the invention is not to be limited to the specific conditions or details described in these examples. Throughout the specification, any and all references to a publicly available document, including a U.S. patent, are specifically incorporated by reference.

Synthesis

All reactions were performed in flame dried glassware and stirred magnetically. All starting materials were used directly from commercial sources without further purification. All reactions were monitored by thin layer chromatography (TLC) unless otherwise indicated. $^1$H and $^{13}$C NMR were performed on Bruker Ultrashield 400 MHz or 500 MHz instruments. High Resolution Mass Spectrometry was performed by University of Pittsburgh facilities.

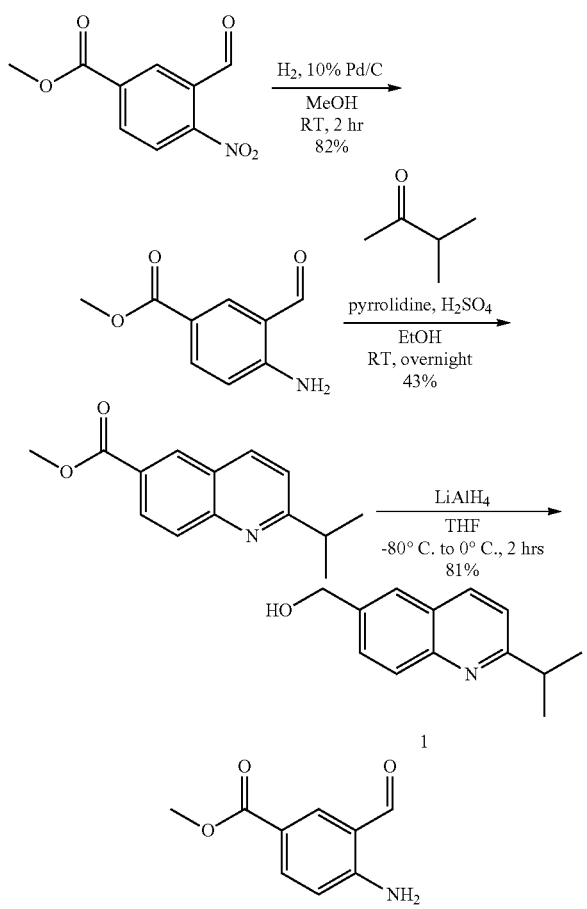

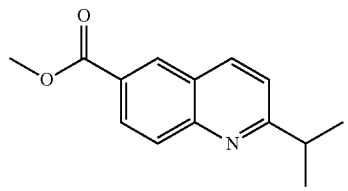 [SMILES: COC(=O)c1ccc2nc(C(C)C)ccc2c1]

Methyl 4-amino-3-formylbenzoate. Methyl 3-formyl-4-nitrobenzoate (200 mg, 0.956 mmol) was dissolved in methanol (8 mL) at room temperature. Palladium on carbon (20 mg, 10% w/w) was added to the reaction mixture while stirring. Hydrogen was bubbled through the reaction, while stirring at room temperature for 2 hours. The reaction mixture was diluted in methanol (8 mL) and vacuum filtered over celite. The filtrate was concentrated in vacuo, dried, and purified by flash chromatography in 20% EtOAc/Hexanes to yield a light yellow solid (140 mg, 82%). $^1$H NMR (400 MHz, CDCl$_3$) δ 9.90 (s, 1H), 8.25 (d, J=2 Hz, 1H), 7.95 (dd, J=2, 8.8 Hz, 1H), 6.65 (d, J=8.8 Hz, 1H), 3.89 (s, 3H). $^{13}$C NMR (400 MHz, CDCl$_3$) δ 193.8, 166.3, 153.11, 138.8, 136.0, 118.4, 118.0, 115.9, 52.0. HRMS calcd for [M+H]$^+$ 180.06, found 180.06537.

Methyl 2-isopropylquinoline-6-carboxylate. The synthetic protocol for this compound was adapted from a previously reported protocol (P. G. Dormer, K. K. E., et al., J. Org. Chem 2003, 68, 467-477). Methyl 4-amino-3-formylbenzoate (20 mg, 0.112 mmol) was diluted in EtOH (500 µL) at room temperature. Pyrrolidine (11 µL, 0.134 mmol) and then sulfuric acid (2 µL, 0.038 mmol) were added to the reaction mixture while stirring. 3-Methyl-2-butanone (15 µL, 0.134 mmol) was added dropwise. After overnight stirring, the reaction was concentrated and dried. The resulting dark orange oil was diluted with DCM and purified by flash chromatography in 10% EtOAc/Hexanes to yield a clear oil (11.1 mg, 43%). $^1$H NMR (400 MHz, CDCl$_3$) δ 8.53 (d, J=1.6 Hz, 1H), 8.25 (dd, J=2 Hz, 8.8 Hz, 1H), 8.16 (d, J=8.4 Hz, 1H), 8.06 (d, J=8.8 Hz, 1H), 7.39 (d, J=8.4 Hz, 1H), 3.98 (s, 3H), 3.27 (m, 1H), 1.40 (d, J=6.8 Hz, 6H). $^{13}$C NMR (400 MHz, CDCl$_3$) δ 170.2, 166.9, 138.2, 130.8, 129.3, 127.6, 126.2, 120.3, 52.5, 37.3, 29.8, 22.5. HRMS calcd for [M+H]$^+$230.11, found 230.11810.

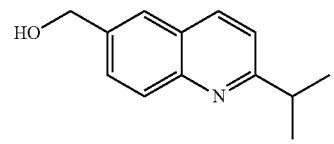

(2-Isopropylquinolin-6-yl)methanol (1). Methyl 2-isopropylquinoline-6-carboxylate (11.1 mg, 0.048 mmol) was diluted in THF (400 µL) at room temperature under N$_2$ and then cooled to −80° C. in a dry ice/isopropanol bath. LiAlH$_4$ (5.5 mg, 0.145 mmol) was added at −80° C. The reaction was stirred at −80° C. for 10 minutes, and was then warmed to 0° C. After 2 hours stirring at 0° C., the reaction was quenched with 10% THF in water (5 mL) at 0° C. The reaction stirred at 0° C. for 10 minutes, and then was diluted with EtOAc. The aqueous layer was extracted with EtOAc (3×, 5 mL). Organic layers were combined, washed with brine (15 mL), dried with Na$_2$SO$_4$, filtered over cotton, and concentrated in vacuo. The residue was purified by flash chromatography with 4% MeOH/DCM to yield 1 as an off-white solid (7.8 mg, 81%). $^1$H NMR (400 MHz, CDCl$_3$) δ 8.05 (d, J=8.4 Hz, 1H), 8.01 (d, J=8.4 Hz, 1H), 7.73 (s, 1H), 7.64 (dd, J=8.8 Hz, 2 Hz, 1H), 7.34 (d, J=8.4 Hz, 1H), 4.87 (s, 2H), 3.25 (m, 1H), 1.38 (d, J=6.8 Hz, 6H). $^{13}$C NMR (500 MHz, CDCl$_3$) δ 167.8, 147.4, 138.5, 136.5, 129.3, 128.6, 126.9, 125.0, 119.5, 65.1, 37.4, 22.7. HRMS calcd for [M+H]$^+$202.1234, found 202.1213.

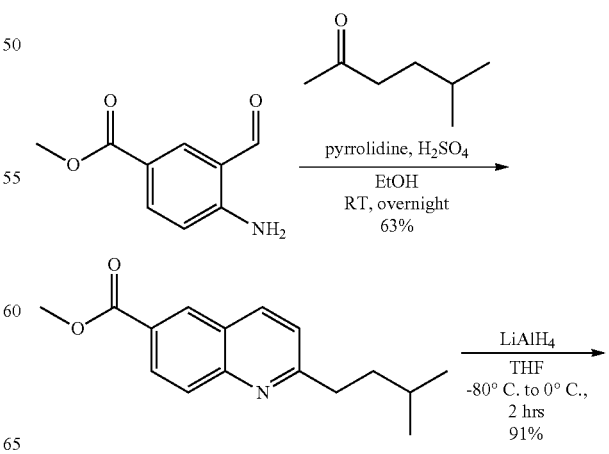

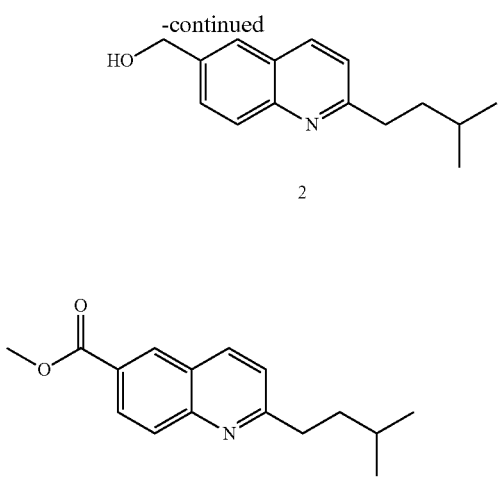

2

Methyl 2-isopentylquinoline-6-carboxylate. The synthetic protocol for this compound was adapted from a previously reported protocol (P. G. Dormer, K. K. E., et al., *J. Org. Chem* 2003, 68, 467-477). Methyl 4-amino-3-formylbenzoate (20 mg, 0.112 mmol) was diluted in EtOH (700 μL) at room temperature. Pyrrolidine (11 μL, 0.134 mmol) and then sulfuric acid (2 μL, 0.038 mmol) were added to the reaction mixture while stirring. 5-Methyl-2-hexanone (19 μL, 0.134 mmol) was added dropwise. After overnight stirring, the reaction was concentrated and dried. The resulting dark orange oil was diluted with DCM and purified by flash chromatography in 5% EtOAc/Hexanes to yield a clear oil (18.2 mg, 63%). $^1$H NMR (400 MHz, CDCl$_3$) δ 8.54 (d, J=1.6 Hz, 1H), 8.26 (dd, J=1.6 Hz, 8.8 Hz, 1H), 8.15 (d, J=8.4 Hz, 1H), 8.06 (d, J=8.8 Hz, 1H), 7.36 (d, J=8.4 Hz, 1H), 3.98 (s, 3H), 2.99 (m, 2H), 1.69 (m, 3H), 0.99 (d, J=6.4 Hz, 6H). $^{13}$C NMR (400 MHz, CDCl$_3$) δ 166.81, 165.9, 149.4, 137.9, 130.8, 129.3, 128.9, 127.5, 126.0, 122.3, 52.5, 39.0, 37.3, 28.3, 22.6. HRMS calcd for [M+H]$^+$ 258.14, found 258.14999.

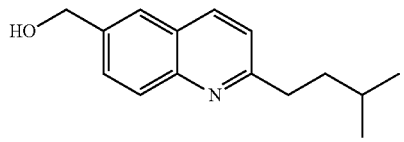

(3-Isobutyl-2-methylquinolin-6-yl)methanol (2). Methyl 2-isopentylquinoline-6-carboxylate (18 mg, 0.070 mmol) was diluted in THF (370 μL) at room temperature under N$_2$ and then cooled to −80° C. in a dry ice/isopropanol bath. LiAlH$_4$ (6.8 mg, 0.179 mmol) was added at −80° C. The reaction was stirred at −80° C. for 10 minutes, and was then warmed to 0° C. After 2 hours stirring at 0° C., the reaction was quenched with 10% THF in water (5 mL). The reaction was stirred at 0° C. for 10 minutes and diluted with EtOAc (5 mL). The aqueous layer was extracted with EtOAc (3×, 5 mL). Organic layers were combined, washed with brine (15 mL), dried with Na$_2$SO$_4$, filtered over cotton, and concentrated in vacuo. The residue was purified by flash chromatography with 4% MeOH/DCM to yield 2 as an off-white solid (15.3 mg, 91%). $^1$H NMR (400 MHz, CDCl$_3$) δ 7.72 (d, J=8.4 Hz, 1H), 7.77 (s, 1H), 7.71 (s, 1H), 7.59 (dd, J=2 Hz, 8.8 Hz, 1H), 4.86 (s, 2H), 2.71 (s, 3H), 2.63 (d, J=7.2 Hz, 2H), 1.96 (m, 1H), 0.97 (d, J=6.4 Hz, 6H). $^{13}$C NMR (500 MHz, CDCl$_3$) δ 158.9, 146.2, 138.4, 135.9, 133.8, 128.7, 127.9, 127.2, 124.6, 65.2, 42.4, 28.8, 23.4, 22.6. HRMS calcd for [M+H]$^+$ 230.1547, found 230.1529.

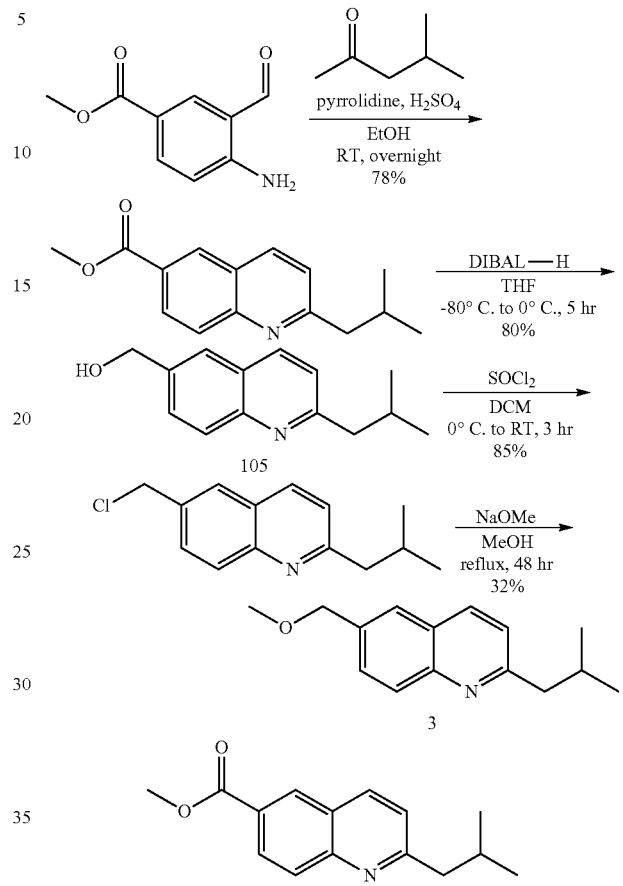

Methyl 2-isobutylquinoline-6-carboxylate. The synthetic protocol for this compound was adapted from a previously reported protocol (P. G. Dormer, K. K. E., et al., *J. Org. Chem* 2003, 68, 467-477). Methyl 4-amino-3-formylbenzoate (25 mg, 0.140 mmol) was diluted in EtOH (300 μL) at room temperature. Pyrrolidine (13 μL, 0.154 mmol) and then sulfuric acid (2 μL, 0.007 mmol) were added to the reaction mixture while stirring. 4-Methyl-2-pentanone (20 μL, 0.154 mmol) was added dropwise. After overnight stirring, the reaction was concentrated and dried. The resulting dark orange oil was diluted with DCM and purified by flash chromatography in 20% EtOAc/Hexanes to yield a yellow oil (26.5 mg, 78%). $^1$H NMR (400 MHz, CDCl$_3$) δ 8.54 (d, J=1.6 Hz, 1H), 8.26 (dd, J=7.2 Hz, 1.6 Hz, 1H), 8.14 (d, J=6.4 Hz, 1H), 8.06 (d, J=6.8 Hz, 1H), 7.32 (d, J=6.8 Hz, 1H), 3.98 (s, 3H), 2.86 (d, J=6 Hz, 2H), 2.23 (m, 1H), 0.98 (d, J=5.6 Hz, 6H). $^{13}$C NMR (500 MHz, CDCl$_3$) δ 167.0, 165.0, 150.0, 137.2, 130.8, 129.3, 129.0, 127.3, 126.0, 123.0, 52.5, 48.6, 29.5, 22.7. HRMS calcd for [M+H]$^+$ 244.13, found 244.13409.

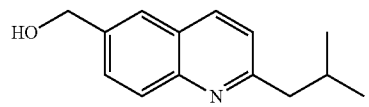 [SMILES: CC(C)Cc1ccc2cc(CO)ccc2n1]

(2-Isobutylquinolin-6-yl)methanol (Compound 8). Methyl 2-isobutylquinoline-6-carboxylate (22.8 mg, 0.094 mmol) was diluted in THF (500 µL) and cooled to −80° C. in an acetone/dry ice bath. DIBAL-H was added dropwise at −80° C. and stirring under nitrogen atmosphere. The reaction was stirred for 20 minutes at −80° C. and then warmed to 0° C. and stirred for 4 hours. The reaction was quenched and worked up following a previously reported literature procedure (K. Brak, et al., *J. Am. Chem. Soc.* 2008, 130, 6404-6410). The residue was purified by flash chromatography in 2% MeOH/DCM to yield 105 as an off-white solid (16.2 mg, 80%). $^1$H NMR (400 MHz, CDCl$_3$) δ 8.03 (dd, J=8.4 Hz, 0.8 Hz, 2H), 7.76 (s, 1H), 7.66 (dd, J=8.8 Hz, 1.6 Hz, 1H), 7.28 (d, J=1.6 Hz, 1H), 4.89 (s, 2H), 2.85 (d, 7.6 Hz, 2H), 2.21 (m, 1H), 0.98 (d, J=6.4 Hz, 3H). $^{13}$C NMR (500 MHz, CDCl$_3$) δ 162.2, 147.4, 138.7, 136.2, 128.9, 128.7, 126.7, 124.9, 122.3, 64.8, 48.2, 29.6, 22.6. HRMS calcd for [M+H]$^+$216.139, found 216.1392.

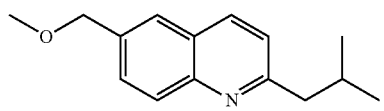 [SMILES: COCc1ccc2nc(CC(C)C)ccc2c1]

6-(Chloromethyl)-2-isobutylquinoline. Compound 105 (18 mg, 0.084 mmol) was diluted in DCM (500 µL) and cooled to 0° C. Thionyl chloride (9 µL, 0.125 mmol) was added dropwise at 0° C. The reaction mixture was gradually warmed to room temperature while stirring for 3 hours. The reaction was concentrated in vacuo and purified by flash chromatography in 15% EtOAc/Hexanes to yield a light yellow oil (14.8 mg, 75%). $^1$H NMR (400 MHz, CDCl$_3$) δ 8.06 (d, J=8.4 Hz, 1H), 8.04 (d, J=8.4 Hz, 1H), 7.77 (s, 1H), 7.70 (dd, J=1.6 Hz, 8.8 Hz, 1H), 7.29 (d, J=8.4 Hz, 1H), 4.75 (s, 2H), 2.85 (d, J=7.2 Hz, 2H), 2.21 (m, 1H), 0.97 (d, J=6.8 Hz, 6H). $^{13}$C NMR (400 MHz, CDCl$_3$) δ 163.1, 147.7, 136.2, 134.9, 129.9, 129.7, 127.2, 126.6, 122.7, 48.3, 46.2, 29.6, 22.7. HRMS calcd for [M+H]$^+$234.10, found 234.10524.

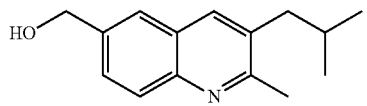 [SMILES: Cc1nc2ccc(CO)cc2cc1CC(C)C]

2-Isobutyl-6-(methoxymethyl)quinolone (3). 6-(Chloromethyl)-2-isobutylquinoline (28.6 mg, 0.122 mmol) was dissolved in MeOH (2 mL) at room temperature while stirring. Sodium methoxide (14 mg, 0.244 mmol) was added and the reaction was heated to 60° C. After 24 hours stirring at reflux, sodium methoxide (14 mg) was added. After refluxing an additional 24 hours, the reaction was diluted in water and extracted with EtOAc (3×, 5 mL). The organic layers were combined, washed with brine (15 mL), dried over Na$_2$SO$_4$, filtered over cotton, and concentrated in vacuo. The crude material was purified by flash chromatography with 15% EtOAc/Hexanes to yield 3 as a white solid (8.9 mg, 32%). $^1$H NMR (400 MHz, CDCl$_3$) δ 8.03 (d, J=2.4 Hz, 8.8 Hz, 2H), 7.73 (s, 1H), 7.64 (dd, J=2 Hz, 8.8 Hz, 1H), 7.26 (d, J=8.4 Hz, 1H), 4.62 (s, 2H), 3.44 (s, 3H), 2.84 (d, J=7.6 Hz, 2H), 2.21 (m, 1H), 0.97 (d, J=6.8 Hz, 6H). $^{13}$C NMR (400 MHz, CDCl$_3$) δ 162.4, 147.4, 136.0, 135.77, 129.2, 126.6, 126.0, 122.4, 74.5, 58.4, 48.4, 29.6, 22.7. HRMS calcd for [M+H]$^+$230.158, found 230.1543.

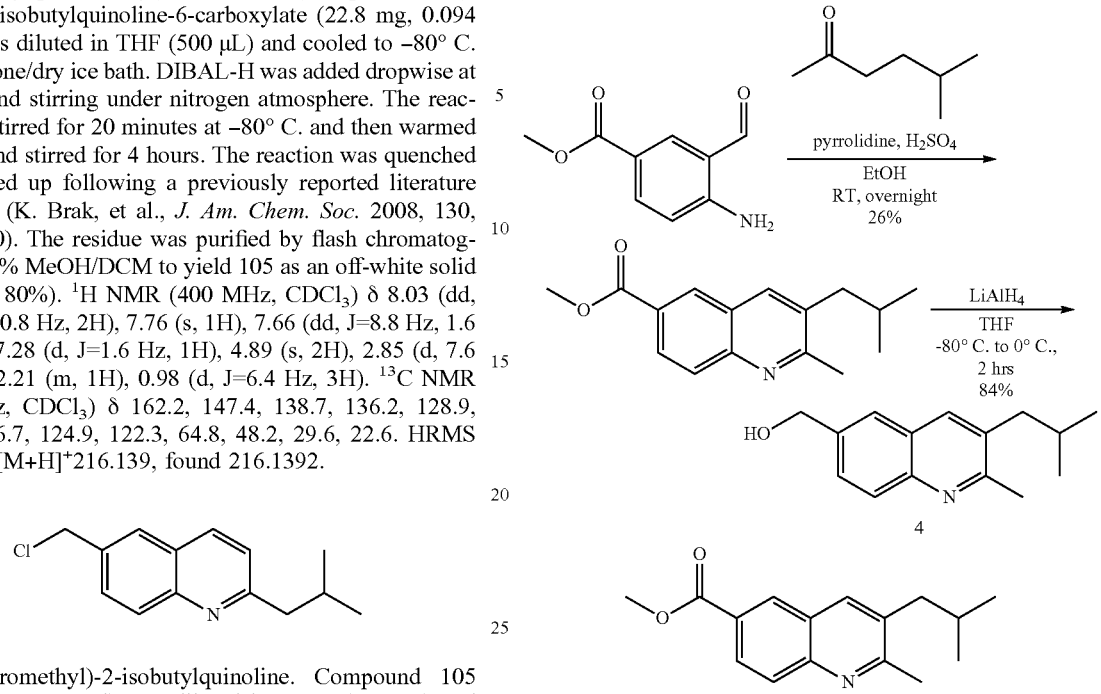

Methyl 3-isobutyl-2-methylquinoline-6-carboxylate. The synthetic protocol for this compound was adapted from a previously reported protocol (P. G. Dormer, K. K. E., et al., *J. Org. Chem* 2003, 68, 467-477). Methyl 4-amino-3-formylbenzoate (20 mg, 0.112 mmol) was diluted in EtOH (700 µL) at room temperature. Pyrrolidine (11 µL, 0.134 mmol) and then sulfuric acid (2 µL, 0.038 mmol) were added to the reaction mixture while stirring. 5-Methyl-2-hexanone (19 µL, 0.134 mmol) was added dropwise. After overnight stirring, the reaction was concentrated and dried. The resulting dark orange oil was diluted with DCM and purified by flash chromatography in 5% EtOAc/Hexanes to yield a clear oil (8.0 mg, 26%). $^1$H NMR (400 MHz, CDCl$_3$) δ 8.51 (d, J=2 Hz, 1H), 8.21 (dd, J=2 Hz, 8.8 Hz, 1H), 8.01 (d, J=8.4 Hz, 1H), 7.88 (s, 1H), 3.98 (s, 3H), 2.75 (s, 3H), 2.66 (d, J=7.2 Hz, 2H), 1.98 (m, 1H), 0.99 (d, J=6.8 Hz, 6H). $^{13}$C NMR (400 MHz, CDCl$_3$) δ 166.7, 161.2, 138.1, 134.8, 130.3, 129.1, 128.0, 127.6, 126.5, 52.6, 42.1, 28.8, 22.6. HRMS calcd for [M+H]$^+$258.14, found 258.15109.

(2-Isopentylquinolin-6-yl)methanol (4). Methyl 3-isobutyl-2-methylquinoline-6-carboxylate (7.2 mg, 0.028 mmol) was diluted in THF (400 µL) at room temperature under N$_2$ and then cooled to −80° C. in a dry ice/isopropanol bath. LiAlH$_4$ (3.2 mg, 0.084 mmol) was added at −80° C. The reaction was stirred at −80° C. for 10 minutes, and was then warmed to 0° C. After 2 hours stirring at 0° C., the reaction was quenched with 10% THF in water (3 mL). The reaction was stirred at 0° C. for 10 minutes and diluted with EtOAc (5 mL). The aqueous layer was extracted with EtOAc (3×, 5 mL). Organic layers were combined, washed with brine (15 mL), dried with Na$_2$SO$_4$, filtered over cotton, and concentrated in vacuo. The residue was purified by flash chromatography with 4% MeOH/DCM to yield 4 as an off-white solid (5.4 mg, 84%). $^1$H NMR (500 MHz, CDCl$_3$) δ 8.00 (d, J=8.5 Hz, 1H), 7.98 (d, J=8.5 Hz, 1H), 7.713 (s, 1H), 7.62 (dd, J=8.5 Hz, 1.5 Hz, 1H), 7.27 (d, J=8.0 Hz, 1H), 4.85 (s, 2H), 2.94 (t, J=7.5 Hz, 2H), 1.67 (m, 3H), 0.96 (d, J=6.5 Hz, 6H). $^{13}$C NMR (500 MHz, CDCl$_3$) δ 163.3, 147.4, 138.6, 136.3, 129.0, 128.7, 126.6, 124.93, 121.6, 64.9, 39.2, 37.3, 28.3, 22.6. HRMS calcd for [M+H]$^+$ 230.1547, found 230.1544.

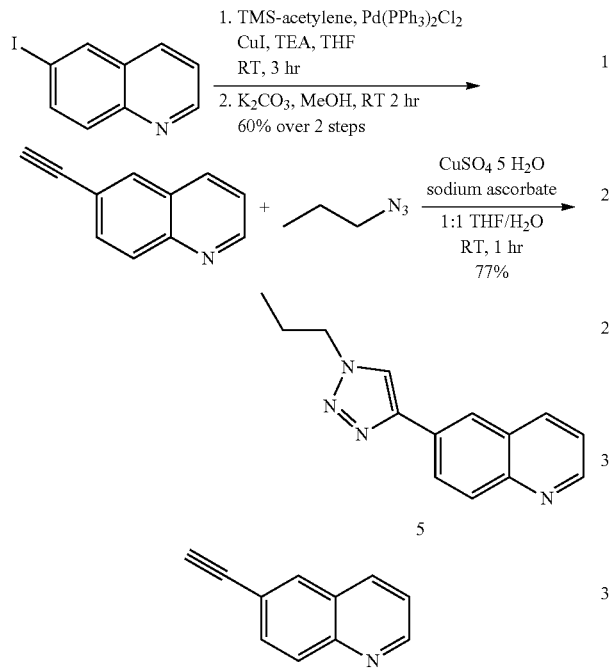

6-Ethynylquinoline. 6-Iodoquinoline (100 mg, 0.392 mmol) was dissolved in THF (1 mL) at room temperature while stirring. Bis(triphenylphosphine)palladium(II) dichloride (14 mg, 0.020 mmol) and copper(I) iodide (4 mg, 0.020 mmol), and triethylamine (82 μL, 0.588 mmol) were added sequentially while stirring at room temperature. Trimethylsilylacetylene (82 μL, 0.588 mmol) was added dropwise under nitrogen atmosphere. The reaction stirred at room temperature for 3 hours, and turned black. The reaction mixture was concentrated in vacuo and dried under high vacuum for several hours. The black residue was carried through crude to the next step. The crude reaction mixture was resuspended in MeOH (1 mL) at room temperature. Potassium carbonate (26 mg, 0.185 mmol) was added and the reaction was stirred at room temperature for 2 hours. After 2 hours, the reaction was diluted in water (5 mL) and DCM (10 mL). The aqueous layer was extracted with DCM (2×, 10 mL). The organic layers were combined, washed with brine (25 mL), dried over Na$_2$SO$_4$, filtered over cotton, and concentrated in vacuo. The residue was purified by flash chromatography in 20% EtOAc/Hexanes to yield a light brown solid (35.7 mg, 60% over two steps). $^1$H NMR (400 MHz, CDCl$_3$) δ 8.93 (dd, J=1.6 Hz, 4 Hz, 1H), 8.15 (d, J=8 Hz, 1H), 8.08 (d, J=8.8 Hz, 1H), 8.01 (d, J=1.2 Hz, 1H), 7.77 (dd, J=2 Hz, 8.8 Hz, 1H), 7.45 (dd, J=4 Hz, 8 Hz, 1H), 3.2 (s, 1H). $^{13}$C NMR (400 MHz, CDCl$_3$) δ 150.7, 147.3, 136.6, 132.8, 132.1, 129.3, 128.1, 121.9, 120.9, 83.1, 78.8. HRMS calcd for [M+H]$^+$154.06, found 154.06509.

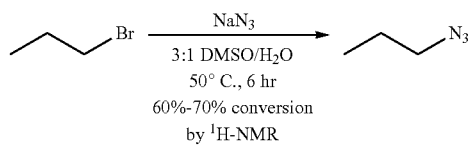

1-Azidopropane. Sodium azide (860 mg, 13.2 mmol) is dissolved in water (1 mL) at room temperature. Dimethylsulfoxide (3 mL) is added to the stirring solution. 1-Bromopropane (1 mL, 11 mmol) is added dropwise to the stirring solution, which is then heated to 50° C. The reaction is stirred at 50° C. for 2 hours, upon which two layers form. Aliquots of the top layer (containing a mixture of 1-bromopropane and 1-azidopropane) of the crude reaction mixture are taken and analyzed for reaction progression by $^1$H NMR. Once at about 50-60% conversion. The top layer is decanted and used crude in the subsequent click reaction.

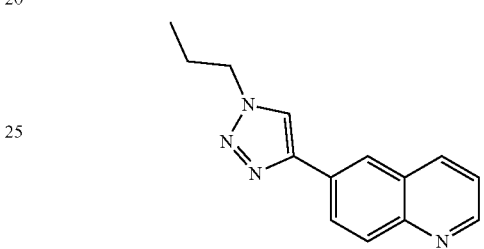

6-(1-Propyl-1H-1,2,3-triazol-4-yl)quinoline (5). 6-ethynylquinoline (20 mg, 0.131 mmol), copper sulfate pentahydrate (3.27 mg, 0.013 mmol), and sodium ascorbate (5.2 mg, 0.026 mmol) are dissolved in THF (440 μL) and water (440 μL) at room temperature. Crude 1-azidopropane (50 μL, excess) is added dropwise to the reaction mixture at room temperature while stirring. After stirring for 1 hour, the reaction mixture was diluted in EtOAc (10 mL) and water (10 mL). The aqueous layer is extracted with EtOAc (3×, 10 mL). The organic layers were combined, washed with brine (20 mL), dried over Na$_2$SO$_4$, filtered over cotton, and concentrated under reduced pressure. The crude material was purified by flash chromatography with 2% MeOH/DCM to yield 5 as a white solid (28.9 mg, 77%). $^1$H NMR (400 MHz, CDCl$_3$) δ 8.91 (s, 1H), 8.38 (d, J=1.2 Hz, 1H), 8.20 (dd, J=8.4 Hz, 1.2 Hz, 1H), 8.15 (d, J=8.8 Hz, 1H), 8.11 (dd, J=8.8 Hz, 1.6 Hz, 1H), 7.89 (s, 1H), 7.42 (dd, J=8.4 Hz, 4.4 Hz, 1H), 4.41 (t, J=7.2 Hz, 2H), 2.02 (m, 2H), 1.02 (t, J=7.2 Hz, 3H). $^{13}$C NMR (400 MHz, CDCl$_3$) δ 150.5, 148.0, 147.1, 136.4, 130.0, 128.9, 128.6, 127.5, 124.1, 121.7, 120.0, 52.2, 23.8, 11.1. HRMS calcd for [M+H]$^+$239.1298, found 239.1281

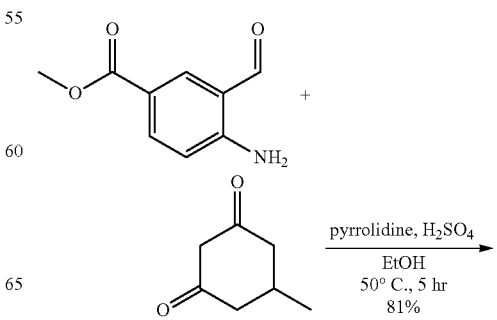

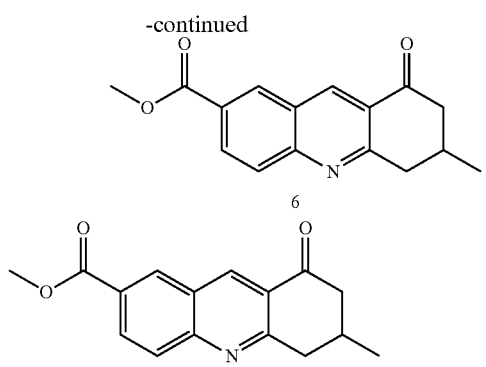

Methyl 6-methyl-8-oxo-5, 6, 7, 8-tetrahydroacridine-2-carboxylate (6). The synthetic protocol for compound 6 was adapted from a previously reported protocol (P. G. Dormer, K. K. E., et al., *J. Org. Chem* 2003, 68, 467-477). Methyl 4-amino-3-formylbenzoate (100 mg, 0.558 mmol) was diluted in EtOH (1 mL) at room temperature. Pyrrolidine (50 μL, 0.614 mmol) and sulfuric acid (9 μL, 0.167 mmol) were added sequentially at room temperature. The reaction was heated to 50° C. Once at temperature, 5-methylcyclohexane-1,3-dione (77 mg, 0.614 mmol) was added. The reaction was stirred at 50° C. for 5 hours before being concentrated in vacuo. The resulting light brown oil was resuspended in DCM and purified by flash chromatography in 20% EtOAc/Hexanes to yield 6 as a white solid (121.7 mg, 81%). $^1$H NMR (400 MHz, CDCl$_3$) δ 8.93 (s, 1H), 8.70 (d, J=1.6 Hz, 1H), 8.39 (d, J=1.6 Hz, 8.8 Hz, 1H), 8.10 (d, J=8.8 Hz, 1H), 4.01 (s, 1H), 3.43 (dd, J=3.6 Hz, 15.2 Hz, 1H), 3.03 (dd, J=10.8 Hz, 16.8 Hz, 1H), 2.91 (m, 1H), 2.51 (m, 2H), 1.25 (d, J=6.4 Hz, 3H). $^{13}$C NMR (400 MHz, CDCl$_3$) δ 166.2, 163.7, 138.1, 132.8, 131.7, 129.0, 128.4, 126.4, 126.0, 52.6, 47.0, 41.8, 28.9, 21.3. HRMS calcd for [M+H]$^+$ 270.11, found 270.11295.

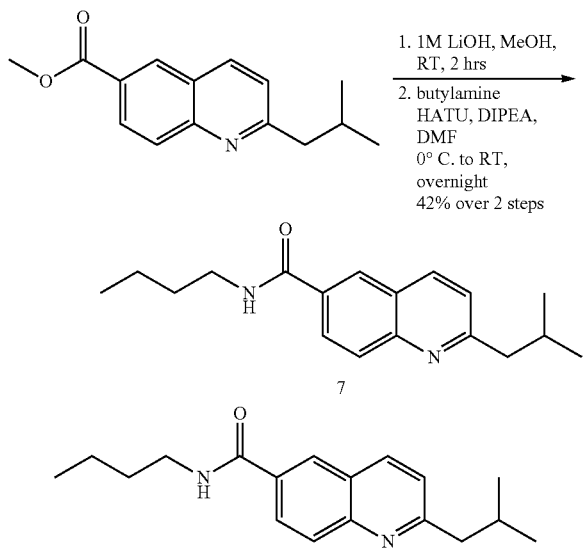

N-Butyl-2-isobutylquinoline-6-carboxamide (7). Methyl 2-isobutylquinoline-6-carboxylate (23.1 mg, 0.095 mmol) was diluted in MeOH (1 mL) at room temperature. A 1M solution of lithium hydroxide (300 μL, 0.3 mmol) was added to the solution stirring at room temperature. After stirring for 2 hours, the reaction was acidified to pH 4 with 5M HCl upon which a white precipitate formed. The reaction mixture was diluted in EtOAc (5 mL). The aqueous layer was extracted with EtOAc (3×5 mL). The organic extracts were combined, washed with brine (15 mL), dried over Na$_2$SO$_4$, filtered over cotton, and concentrated in vacuo. The crude white solid was carried forward without further purification. The white solid was dissolved in DMF (500 μL) and cooled to 0° C. Diisopropylethylamine (75 μL, 0.431 mmol), and butylamine (17 μL, 0.172 mmol) were added sequentially while stirring at 0° C. HATU (81 mg, 0.215 mmol) was added, and the reaction was stirred at 0° C. for 10 minutes, before warming to RT. After overnight stirring the reaction was diluted with EtOAc and worked up with water. The aqueous layer was extracted with EtOAc (3×, 10 mL). The organic layers were combined, washed with brine (20 mL), dried over Na$_2$SO$_4$, filtered over cotton, and concentrate in vacuo. The crude mixture was resuspended in DCM nd purified by flash chromatography with 40% EtOAc/Hexanes to yield 7 as a light brown solid (17.2 mg, 42% over two steps). $^1$H NMR (400 MHz, CDCl$_3$) δ 8.26 (d, J=2 Hz, 1H), 8.12 (d, J=8.4 Hz, 1H), 8.07 (d, J=8.8 Hz, 1H), 7.99 (dd, J=8.8 Hz, 2 Hz, 1H), 7.32 (d, J=8.4 Hz, 1H), 6.28 (br s, 1H), 3.51 (m, 2H), 2.86 (d, J=7.2 Hz, 2H), 2.23 (m, 1H), 1.65 (m, 2H), 1.45 (m, 2H), 0.98 (m, 9H). $^{13}$C NMR (400 MHz, CDCl$_3$) δ 166.9, 164.2, 131.8, 129.3, 127.3, 126.8, 126.1, 122.9, 48.4, 40.0, 31.8, 29.4, 22.6, 20.2, 13.8. HRMS calcd for [M+H]$^+$ 285.1889, found 285.1977.

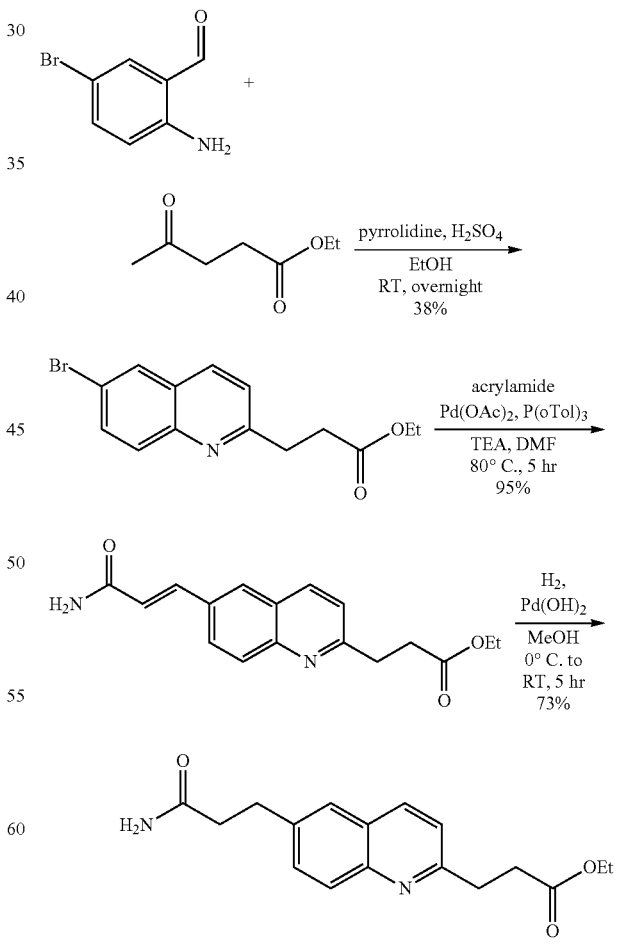

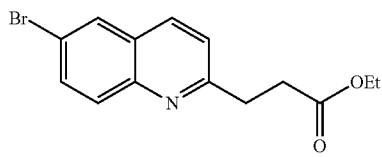 [SMILES: CCOC(=O)CCc1ccc2cc(Br)ccc2n1]

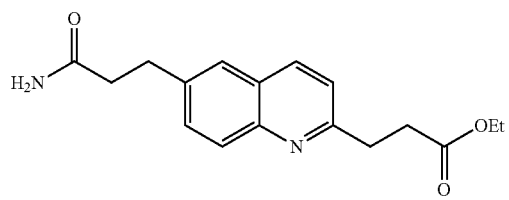

Ethyl 3-(6-bromoquinolin-2-yl)propanoate. The synthetic protocol for this compound was adapted from a previously reported protocol (P. G. Dormer, K. K. E., et al., *J. Org. Chem* 2003, 68, 467-477). 2-Amino-5-bromobenzaldehyde (350 mg, 1.74 mmol) was dissolved in EtOH (2.5 mL) at room temperature. Pyrrolidine (156 µL, 1.91 mmol) and sulfuric acid (15.2 µL, 0.5 mmol) were added sequentially at room temperature. Ethyl levulinate (271 µL, 1.91 mmol) was added dropwise at room temperature and the reaction stirred overnight. The reaction mixture was concentrated in vacuo and the resulting dark orange oil was dried on high vacuum. The crude reaction was resuspended in DCM and purified by flash chromatography with a 5-20% EtOAc/Hexanes gradient to yield a light yellow solid (203.7 mg, 38%). $^1$H NMR (500 MHz, CDCl$_3$) δ 7.96 (d, J=8 Hz, 1H), 7.93 (d, J=2 Hz, 1H), 7.87 (d, J=9 Hz, 1H), 7.73 (dd, J=2.5 Hz, 9 Hz, 1H), 7.33 (d, J=8.5 Hz, 1H), 4.14 (q, J=7.5 Hz, 2H), 3.28 (t, J=7 Hz, 2H), 2.91 (t, J=7 Hz, 2H), 1.23 (t, J=7 Hz). $^{13}$C NMR (400 MHz, CDCl$_3$) δ 173.2, 161.1, 146.6, 135.3, 132.9, 130.8, 129.7, 128.1, 122.5, 119.7, 60.6, 33.6, 33.0, 14.4. HRMS calcd for [M+H]$^+$308.02, found 308.03134.

Ethyl 3-(6-(3-amino-3-oxopropyl)quinolin-2-yl)propanoate (9). Ethyl (E)-3-(6-(3-amino-3-oxoprop-1-ene-1-yl)quinolin-2-yl)propanoate (46 mg, 0.153 mmol) was dissolved in methanol (3 mL) and cooled to 0° C. in an ice bath. Palladium(II) hydroxide (4.5 mg, 20% w/w) was added to the reaction mixture while stirring. Hydrogen was bubbled through the reaction, and the reaction was gradually warmed to room temperature. Hydrogen was bubbled through the reaction for 5 hours while stirring. The reaction mixture was diluted in methanol (8 mL) and vacuum filtered over a pad of celite. The filtrate was concentrated in vacuo, dried, and purified by flash chromatography in 4% MeOH/DCM to yield 9 as a white solid (33.4 mg, 73%). $^1$H NMR (400 MHz, CDCl$_3$) δ 8.10 (dd, J=3.2 Hz, 8.4 Hz, 2H), 7.63 (s, 1H), 7.58 (dd, J=2 Hz, 8.8 Hz, 1H), 7.37 (d, J=8.4 Hz, 1H), 5.85 (br s, 1H), 5.62 (br s, 1H), 4.10 (q, J=7.2 Hz, 2H), 3.35 (t, J=7.2 Hz, 2H), 3.12 (t, J=7.6 Hz, 2H), 2.93 (t, J=7.2 Hz, 2H), 2.61 (t, J=8 Hz, 2H), 1.21 (t, J=7.2 Hz, 3H). $^{13}$C NMR (400 MHz, CDCl$_3$) δ 174.2, 172.9, 159.7, 144.7, 139.7, 138.0, 131.8, 127.3, 127.1, 126.5, 122.0, 60.7, 37.1, 33.4, 32.5, 31.3, 14.3. HRMS calc for [M+H]$^+$ 301.159 found 301.15620.

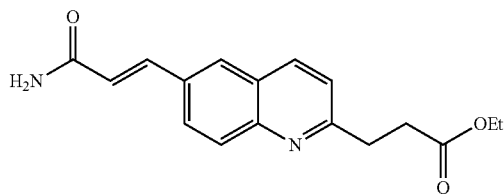 [SMILES: CCOC(=O)CCc1ccc2cc(/C=C/C(N)=O)ccc2n1]

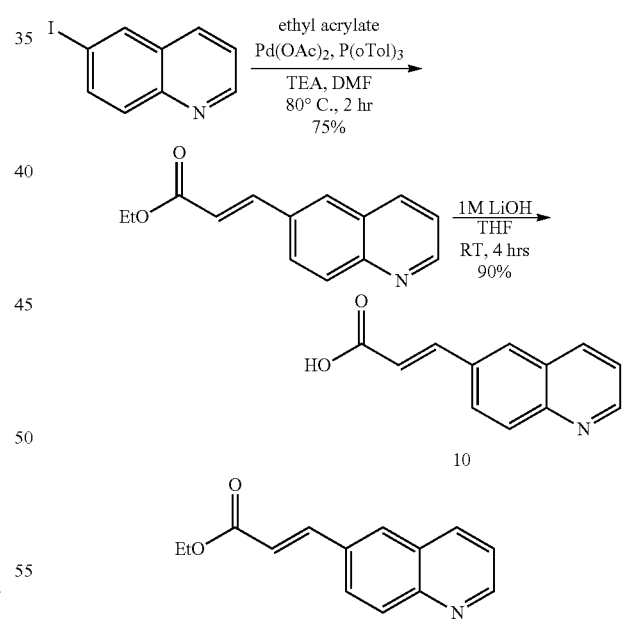

Ethyl (E)-3-(6-(3-amino-3-oxoprop-1-ene-1-yl)quinolin-2-yl)propanoate. Ethyl 3-(6-bromoquinolin-2-yl)propanoate (175 mg, 0.567 mmol) was dissolved in DMF (2.2 mL). Palladium(II) acetate (12.7 mg, 0.057 mmol), tri(o-tolyl)phosphine (69 mg, 0.227 mmol), and trimethylamine (800 µL, 5.67 mmol) were added sequentially at room temperature under nitrogen atmosphere. Acrylamide (121 mg, 1.70 mmol) was added last and the reaction was heated to 80° C. for 5 hours. The reaction was cooled to room temperature and diluted with EtOAc (10 mL) and water (25 mL). The aqueous layer was extracted with EtOAc (5×, 10 mL). The organic layers were combined, washed with water (25 mL) and then brine (25 mL), dried over Na$_2$SO$_4$, filtered over cotton, and concentrated in vacuo. The dark brown solid was redissolved in DCM and purified in 3% MeOH/DCM to yield a beige solid (162 mg, 95%). $^1$H NMR (400 MHz, CDCl$_3$) δ 8.02 (d, J=8.4 Hz, 1H), 7.96 (d, J=9.2 Hz, 1H), 7.81 (m, 2H), 7.78 (d, J=15.6 Hz, 1H), 7.32 (d, J=8.4 Hz, 1H), 6.57 (d, J=15.6 Hz, 1H), 5.91 (br s, 2H), 4.13 (q, J=7.2 Hz, 2H), 3.29 (t, J=7.2 Hz, 2H), 2.91 (t, J=7.2 Hz, 2H), 1.23 (t, J=7.2 Hz, 3H). $^{13}$C NMR (400 MHz, CDCl$_3$) δ 173.2, 167.8, 161.7, 148.7, 141.9, 136.7, 132.2, 129.8, 129.0, 127.2, 127.0, 122.4, 120.5, 60.6, 33.7, 33.1, 14.4. HRMS calcd for [M+H]$^+$299.13, found 299.14049.

Ethyl (E)-3-(quinolin-6-yl)acrylate. 6-Iodoquinoline (200 mg, 0.784 mmol) was diluted in DMF. Palladium acetate (35 mg, 0.157 mmol), tri(o-tolyl)phosphine (95 mg, 0.314 mmol), and trimethylamine (219 µL, 1.57 mmol) were added sequentially under nitrogen atmosphere. Ethyl acrylate (100 µL, 1.18 mmol) was added dropwise to the reaction mixture. The reaction mixture was heated to 80° C. and stirred for 2 hours. The reaction was cooled to room temperature and diluted with EtOAc (4 mL) worked up in H$_2$O (50 mL). The aqueous layer was extracted with EtOAc (3×, 10 mL). The organic layers were combined, washed brine (30 mL), dried over Na$_2$SO$_4$, filtered over cotton, and concentrated under reduced pressure. The crude solid was redissolved in DCM and purified by flash chromatography with 15% EtOAc/Hexanes to yield a light yellow solid (134 mg, 75%). $^1$H NMR (400 MHz, CDCl$_3$) δ 8.90 (d, J=2.8 Hz, 1H), 8.14 (d, J=8 Hz, 1H), 8.07 (d, J=9.2 Hz, 1H), 7.88 (m, 2H), 7.82 (d, J=16 Hz, 1H), 7.41 (dd, J=4 Hz, 8.4 Hz, 1H), 6.55 (d, J=16 Hz, 1H), 4.28 (q, J=7.2 Hz, 2H), 1.34 (t, J=7.2 Hz, 3H). $^{13}$C NMR (400 MHz, CDCl$_3$) δ 166.8, 151.3, 149.0, 143.6, 136.5, 132.7, 130.3, 129.2, 128.3, 127.3, 121.9, 119.7, 60.7, 14.3. HRMS calcd for [M+H]$^+$228.09, found 228.10211.

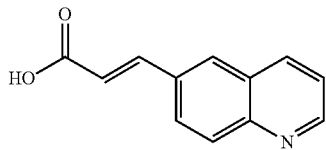 [SMILES: O=C(O)/C=C/c1ccc2ncccc2c1]

(E)-3-(quinolin-6-yl)acrylic acid (10). Ethyl (E)-3-(quinolin-6-yl)acrylate (343 mg, 1.51 mmol) was diluted in THF (2 mL) and stirred at room temperature. A 1M solution of lithium hydroxide (3.3 mL) was added dropwise and the reaction was stirred for 2 hours. After stirring at room temperature for two hours, the crude reaction mixture was pH adjusted to pH=1 with 5M HCl, upon which a white precipitate formed. The reaction mixture was vacuum filtered and the filtered solid was rinsed with water. The white solid (269 mg, 90%) was collected and used without further purification. $^1$H NMR (400 MHz, d6-DMSO) δ 12.54 (br s, 1H), 8.92 (d, J=2.4 Hz, 1H), 8.38 (d, J=8.4 Hz, 1H), 8.26 (s, 1H), 8.13 (d, J=8.8 Hz, 1H), 8.01 (d, J=8.8 Hz, 1H), 7.76 (d, J=16 Hz, 1H), 7.57 (dd, J=4 Hz, 8 Hz, 1H), 6.71 (d, J=16 Hz). $^{13}$C NMR (300 MHz, d6-DMSO) δ 167.4, 151.4, 148.3, 142.9, 136.5, 132.4, 129.5, 129.4, 127.9, 127.7, 122.10, 120.8. HRMS calcd for [M+H]$^+$200.21, found 200.07036.

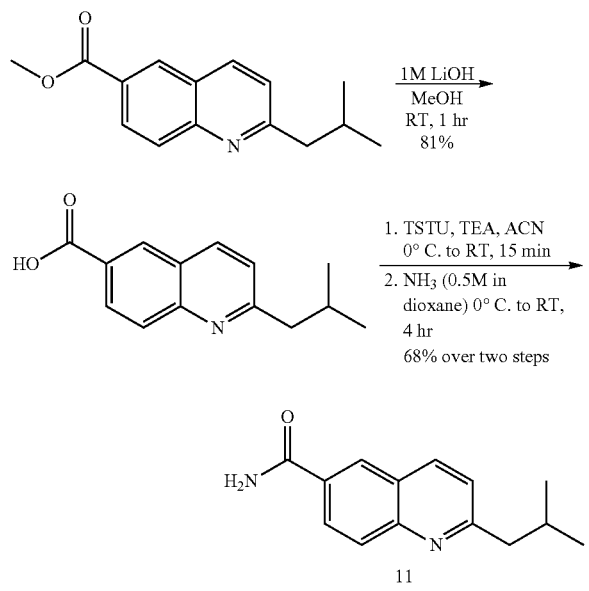

11

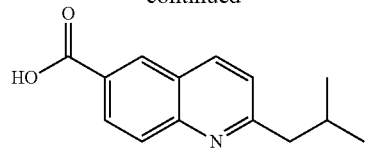

2-Isobutylquinoline-6-carboxylic acid. Methyl 2-isobutylquinoline-6-carboxylate (61 mg, 0.250 mmol) was dissolved in MeOH (1 mL) while stirring at room temperature. A 1M solution of lithium hydroxide (400 μL) was added dropwise at room temperature, and the reaction was stirred at room temperature. After 1 hour of stirring, the reaction mixture was pH adjusted to pH=2 with 5M HCl. The reaction was left to stir at room temperature for 15 minutes. The reaction mixture was diluted with EtOAc (5 mL), and worked up with water (5 mL). The aqueous layer was extracted with EtOAc (3×, 5 mL). The organic layers were combined, washed with brine (15 mL), dried over Na$_2$SO$_4$, filtered over cotton, and concentrated in vacuo. The crude material was purified by flash chromatography with 8% MeOH/DCM to yield a white powdery solid (46 mg, 81%). 1H NMR (400 MHz, CDCl$_3$) δ 13.14 (br s, 1H), 8.61 (d, J=1.6 Hz, 1H), 8.44 (d, J=8.4 Hz, 1H), 8.16 (dd, J=2 Hz, 8.8 Hz, 1H), 7.99 (d, J=8.8 Hz, 1H), 7.49 (d, J=8.4 Hz, 1H), 2.81 (d, J=7.2 Hz, 2H), 2.19 (m, 1H), 0.91 (d, J=6.8 Hz, 6H). 13C NMR (400 MHz, CDCl$_3$) δ 167.1, 164.2, 149.1, 137.4, 130.6, 128.8, 128.7, 127.8, 125.7, 122.9, 47.4, 28.5, 22.4. HRMS calcd for [M+H]$^+$230.11, found 230.11784.

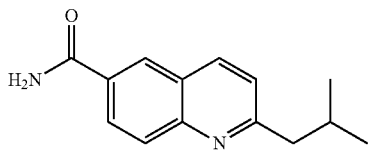 [SMILES: CC(C)Cc1ccc2cc(C(N)=O)ccc2n1]

2-Isobutylquinoline-6-carboxamide (11). 2-Isobutylquinoline-6-carboxylic acid (46 mg, 0.201 mmol) was dissolved in ACN (2 mL) and cooled to 0° C. while stirring. Triethylamine (71 μL, 0.508 mmol) was added dropwise at 0° C. TSTU (67 mg, 0.223 mmol) was added to the reaction at 0° C., and the reaction was left to stir at 0° C. for 10 min. The reaction warmed to room temperature over an hour. The reaction was concentrated in vacuo and the crude material was used without further purification. The crude material was dissolved in a 0.5M NH$_3$ solution in dioxane (6 mL, excess) added dropwise to the solution at 0° C. Upon complete addition of NH$_3$ in dioxane, the reaction was stirred at 0° C. for 2 minutes, and then removed from the ice bath and allowed to warm to room temperature. The reaction was stirred at room temperature for 4 hours and then concentrated in vacuo. The crude solid was dried under high vacuum and purified by flash chromatography with 3% MeOH/DCM to yield 11 as a white solid (31 mg, 68% over two steps). 1H NMR (400 MHz, CDCl$_3$) δ 8.37 (d, J=1.2 Hz, 1H), 8.18 (dd, J=2.8 Hz, 8.4 Hz, 2H), 8.10 (d, J=8.4 Hz, 1H), 7.36 (d, J=8.4 Hz, 1H), 6.50 (br s, 1H), 6.04 (br s, 1H), 2.91 (d, J=7.6 Hz, 2H), 2.24 (m, 1H), 0.98 (d, J=6.4 Hz, 6H). 13C NMR (400 MHz, CDCl$_3$) δ 168.7, 164.4, 138.2, 128.4, 126.2, 123.2, 47.8, 29.7, 22.7. HRMS calcd for [M+H]$^+$ 229.13, found 229.13394.

Compounds 12 and 13

Compounds 12 and 13 were synthesized from commercially available 2-amino-5-bromobenzaldehyde. A Friedlander reaction was used to generate the 6-bromo-2-isobutylquinoline intermediate, which was subsequently converted to the unsaturated amide through a palladium-catalyzed Heck coupling. Hydrogenation of the unsaturated amide afforded Compound 12 in 96% yield.

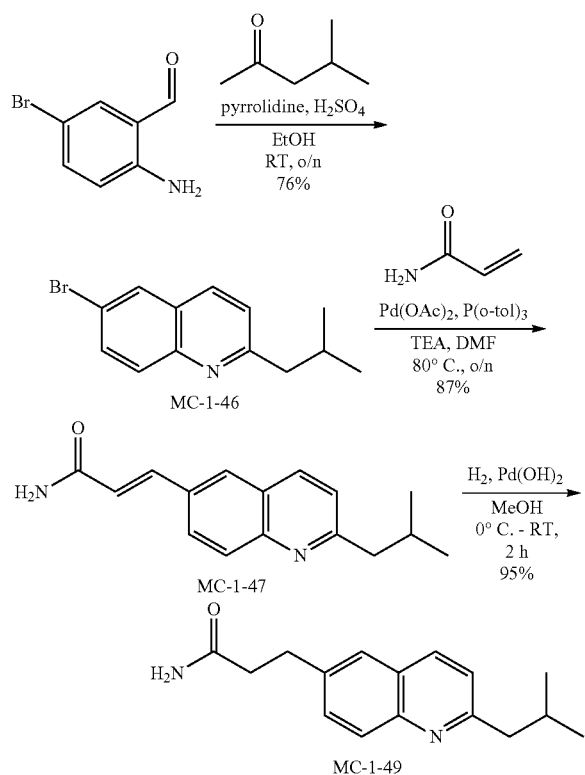

6-Bromo-2-isobutylquinoline. 2-Amino-5-bromobenzaldehyde (110 mg, 0.500 mmol) was dissolved in EtOH (800 µL) at room temperature. Pyrrolidine (45 µL, 0.550 mmol) and then concentrated sulfuric acid (8 µL, 0.150 mmol) were added to the reaction mixture while stirring. 4-Methyl-2-pentanone (69 µL, 0.550 mmol) was added dropwise. After overnight stirring, the reaction was concentrated in vacuo. The yellow-brown residue was diluted with EtOAc and purified by flash chromatography on silica gel using 12% EtOAc in hexanes to yield a yellow solid (117 mg, 76%). $^1$H-NMR (400 MHz, CDCl3) δ 7.96 (d, J=8.8 Hz, 1H), 7.93 (d, J=2.4 Hz, 1H), 7.91 (d, J=8.8 Hz, 1H), 7.74 (dd, J=8.8 Hz, 2 Hz, 1H), 7.28 (d, J=8.4 Hz, 1H), 2.83 (d, J=7.2 Hz, 2H), 2.20 (m, 1H), 0.97 (d, J=6.8 Hz, 6H). 13C-NMR (500 MHz, CDCl3) δ 162.9, 146.7, 135.0, 132.8, 130.9, 129.6, 128.0, 123.0, 119.5, 48.4, 29.5, 22.7. HRMS calcd for [M+H]$^+$264.039, found 264.0398.

(E)-3-(2-Isobutylquinolin-6-yl)acrylamide (Compound 13). 6-Bromo-2-isobutylquinoline (116 mg, 0.439 mmol) was dissolved in DMF (2 mL) at room temperature before palladium (II) acetate (9.8 mg, 0.044 mmol) and tri(o-tolyl) phosphine (54 mg, 0.176 mmol) were added sequentially. Triethylamine (620 µL, 4.39 mmol) and acrylamide (93 mg, 1.31 mmol) were added and the reaction stirred at 80° C. overnight. The reaction was cooled to room temperature and diluted with EtOAc (15 mL) and water (30 mL). The aqueous layer was extracted with EtOAc (3×15 mL). The organic layers were combined, washed with brine (30 mL), dried over anhydrous Na$_2$SO$_4$ (10 g), filtered, and concentrated in vacuo. The brown oil was re-dissolved in DCM and purified by flash chromatography on silica gel using 2.5% MeOH in DCM to yield an off-white solid (104 mg, 87%). $^1$H NMR (400 MHz, CDCl$_3$) δ 8.07 (d, J=8.4 Hz, 1H), 8.04 (d, J=9.2 Hz, 1H), 7.88 (m, 2H), 7.84 (d, J=15.6 Hz, 1H), 7.31 (d, J=5.2 Hz, 1H), 6.59 (d, J=15.6 Hz, 2H), 5.59 (br s, 2H), 2.86 (d, J=7.2 Hz, 2H), 2.22 (m, 1H), 0.98 (d, J=6.8 Hz, 6H). $^{13}$C-NMR (400 MHz, CDCl$_3$) δ 167.4, 163.5, 142.1, 136.3, 131.8, 129.7, 129.0, 127.0, 126.7, 122.8, 119.9, 48.3, 29.5, 22.6. HRMS calcd for [M+H]$^+$ 254.14, found 255.14889.

3-(2-Isobutylquinolin-6-yl)propenamide (Compound 12). (E)-(2-Isobutylquinolin-6-yl)acrylamide (50 mg, 0.197 mmol) was dissolved in MeOH (8 mL) and the reaction mixture was cooled to 0° C. Palladium hydroxide (6 mg, 0.039 mmol) was added to the reaction mixture while stirring. Hydrogen was bubbled through the reaction using a balloon as it stirred to room temperature over two hours. The reaction mixture was filtered over celite, concentrated in vacuo, and purified by flash chromatography on silica gel using 5% MeOH in DCM to afford a light-yellow solid (48 mg, 96%). $^1$H-NMR (400 MHz, CDCl$_3$) δ 8.00 (d, J=8.0 Hz, 1H), 7.99 (d, J=8.4 Hz, 1H), 7.60 (br s, 1H), 7.56 (dd, J=2.0 Hz, 1.6 Hz, 1H), 7.24 (s, 1H), 3.17 (t, J=7.6 Hz, 2H) 2.84 (d, J=7.2 Hz, 2H) 2.64 (t, J=7.6 Hz, 2H), 2.19 (m, 1H), 0.97 (d, J=6.4 Hz, 6H). $^{13}$C-NMR (400 MHz, CDCl$_3$) δ 173.9, 161.8, 146.8, 138.1, 135.6, 130.3, 129.0, 126.7, 126.2, 122.2, 48.2, 37.2, 31.2, 29.5, 22.5. HRMS calcd for [M+H]$^+$ 256.35, found 257.16512.

Compound 22

Compound 22 was synthesized in two steps from commercially available methyl-3-formyl-4-nitrobenzoate. The nitro group was reduced to an amine through a palladium-catalyzed hydrogenation, followed by a Friedlander reaction with 1-hydroxypropan-2-one to afford the final Compound 22 in 59% yield.

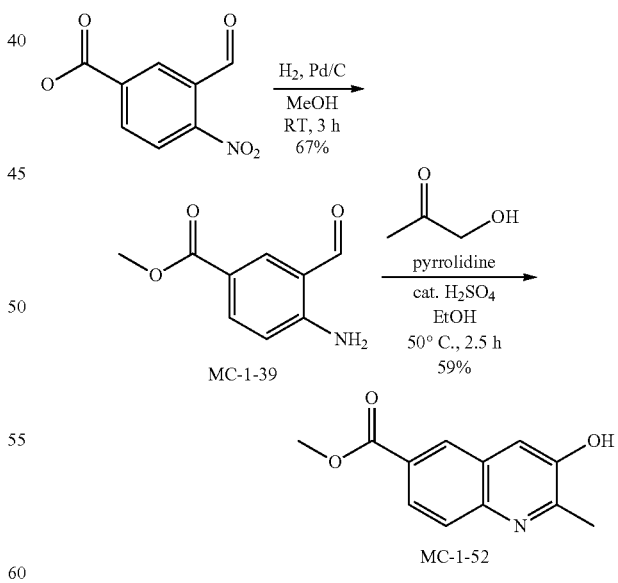

Methyl-4-amino-formylbenzoate. Methyl-3-formyl-4-nitrobenzoate (500 mg, 2.39 mmol) was dissolved in MeOH (10 mL) at room temperature. Palladium on carbon (25 mg, 0.239 mmol) was added, followed by a hydrogen balloon for bubbling the gas through the reaction while stirring at room temperature for three hours. The reaction was filtered over celite, concentrated in vacuo, dried and purified by flash chromatography on silica gel using 20% EtOAc in hexanes to afford a yellow solid (311 mg, 73%). $^1$H-NMR (400 MHz, CDCl$_3$) δ 9.90 (s, 1H), 8.25 (d, J=2 Hz, 1H), 7.95 (dd, J=2, 8.8 Hz, 1H), 6.65 (d, J=8.8 Hz, 1H), 3.89 (s, 3H). $^{13}$C-NMR (400 MHz, CDCl$_3$) δ 193.8, 166.3, 153.11, 138.8, 136.0, 118.4, 118.0, 115.9, 52.0. HRMS calcd for [M+H]$^+$ 180.06, found 180.06537.

Methyl 3-hydroxy-2-methylquinoline-6-carboxylate (Compound 22). Methyl-4-amino-formylbenzoate (89 mg, 0.494 mmol) was dissolved in EtOH (1 mL) at room temperature. Pyrrolidine (49 μL, 0.593 mmol) and concentrated sulfuric acid (8 μL, 0.148 mmol) were added sequentially. 1-Hydroxypropan-2-one (42 μL, 0.593 mmol) was added last and the reaction stirred at 50° C. for two and a half hours before it was concentrated in vacuo. The resulting solid was re-dissolved in EtOAc and purified by flash chromatography on silica gel using 30% EtOAc in hexanes to afford a beige solid (63 mg, 59%). $^1$H-NMR (400 MHz, DMSO) δ 8.46 (d, J=1.6 Hz, 1H), 7.94 (dd, J=2, 8.8 Hz, 1H), 7.89 (d, J=8.4 Hz, 1H), 7.58 (s, 1H), 3.89 (s, 3H) 2.55 (s, 3H). $^{13}$C-NMR (400 MHz, DMSO) δ 166.0, 154.8, 154.8, 150.4, 150.2, 128.9, 127.8, 127.4, 126.8, 125.1, 52.2, 20.0. HRMS calcd for [M+H]$^+$217.07, found 218.08098.

Compound 21

Compound 21 was synthesized through a Friedlander reaction with 2-amino-5-bromobenzaldehyde and 5-methyl-cyclohexane-1,3-dione to afford the final compound 21 in 73% yield.

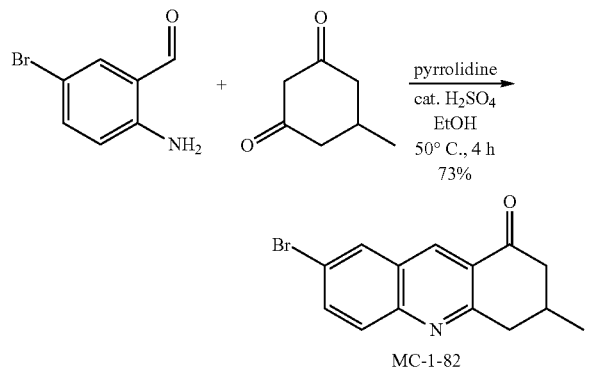

7-Bromo-3-methyl-3,4-dihydroacridin-1(2H)-one (Compound 21). 2-Amino-5-bromobenzaldehyde (150 mg, 0.755 mmol) was dissolved in EtOH (1.5 mL) at room temperature. Pyrrolidine (68 μL, 0.830 mmol) and concentrated sulfuric acid (12 μL, 0.226 mmol) were added sequentially. 5-methylcyclohexane-1,3-dione (105 mg, 0.830 mmol) was added last and the reaction stirred at 50° C. for four hours before it was concentrated in vacuo. The resulting yellow solid was dissolved in EtOAc and purified by flash chromatography on silica gel using 35% EtOAc in hexanes to afford a yellow solid (160 mg, 73%). $^1$H-NMR (400 MHz, CDCl$_3$) δ 8.78 (s, 1H), 8.11 (d, J=2 Hz, 1H), 8.04 (d, J=8.4 Hz, 1H), 7.90 (dd, J=2, 9.2 Hz, 1H), 3.48 (d, J=17.6 Hz, 1H), 3.04 (m, 1H), 2.91 (m, 1H), 2.50 (m, 2H), 1.24 (d, J=6 Hz, 3H). $^{13}$C-NMR (400 MHz CDCl$_3$) δ 204.8, 197.5, 161.7, 135.7, 135.6, 131.4, 130.3, 127.9, 236.3, 120.5, 47.0, 41.5, 28.9, 21.2. HRMS calcd for [M+H]$^+$289.01, found 290.01729.

Compounds 24, 23 and 25

Compounds 24, 23 and 25 were synthesized from commercially available 2-amino-5-iodopyridine-3-carbaldehyde. First, a Friedlander reaction was used to generate the 6-iodo-2-isobutylnaphthalene intermediate. The unsaturated ester compound was obtained through a Heck coupling and subsequent ester hydrolysis generated the acrylic acid compound 124. The unsaturated amide intermediate 23 was synthesized through the N-hydroxysuccinimide ester intermediate, which was subsequently hydrogenated to afford the final compound 25 in 45% yield.

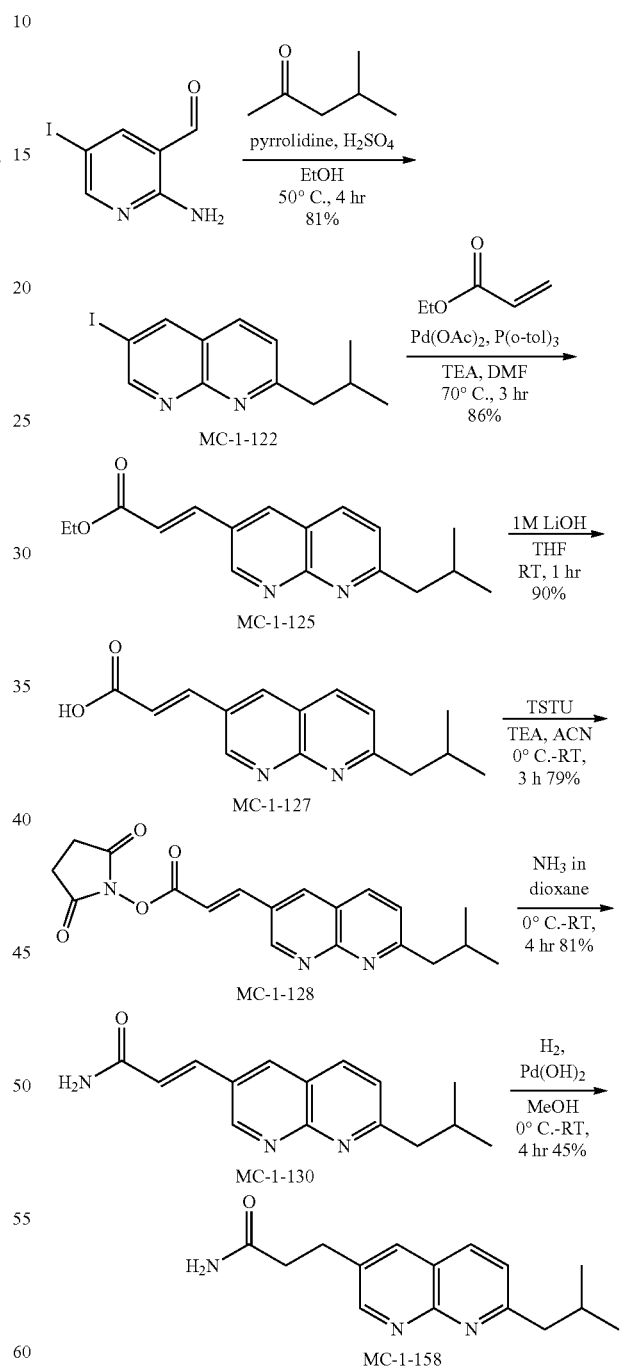

6-Iodo-2-isobutylnaphthyridine. 2-Amino-5-iodopyridine-3-carbaldehyde (80 mg, 0.323 mmol) was dissolved in EtOH (1.5 mL) at room temperature. Pyrrolidine (30 μL, 0.355 mmol) and concentrated sulfuric acid (5.2 μL, 0.097 mmol) were added sequentially. 4-Methyl-2-pentanone (44

μL, 0.355 mmol) was added last and the reaction stirred at 50° C. for five hours before it was concentrated in vacuo. The resulting brown solid was purified by flash chromatography on silica gel using 20% EtOAc in hexanes to yield a pale yellow solid (82 mg, 81%). $^1$H-NMR (400 MHz, CDCl$_3$) δ 9.22 (d, J=2 Hz, 1H), 8.54 (d, J=2 Hz, 1H), 8.04 (d, J=6.8 Hz, 1H), 7.41 (d, J=6.8 Hz, 1H), 2.97 (d, J=6 Hz, 2H), 2.32 (m, 1H), 0.99 (d, J=5.6 Hz, 1H). $^{13}$C-NMR (400 MHz, CDCl$_3$) δ 166.9, 158.6, 154.4, 150.9, 144.2, 135.5, 123.7, 122.8, 89.5, 48.2, 29.1, 22.5. HRMS calcd for [M+H]$^+$312.01, found 313.01927.

(E)-3-(7-Isobutylnaphthyridin-3-yl)acrylate. 6-Iodo-2-isobutylnaphthyridine (60 mg, 0.192 mmol) was diluted in DMF (1 mL) at room temperature before palladium (II) acetate (4 mg, 0.119 mmol) and tri(o-tolyl)phosphine (23 mg, 0.077 mmol) were added sequentially. Triethylamine (270 μL, 1.92 mmol) and ethyl acrylate (42 μL, 0.384 mmol) were added before the reaction stirred at 70° C. for three hours. The crude reaction mixture was diluted with EtOAc (10 mL) and water (25 mL). The aqueous layer was extracted with EtOAc (3×10 mL). The organic layers were combined, washed with brine (25 mL), dried over anhydrous Na$_2$SO$_4$(8 g), filtered over cotton, and concentrated in vacuo. The crude oil was re-dissolved in EtOAc and purified by flash chromatography on silica gel using 30% EtOAc in hexanes to yield a beige solid (43 mg, 86%). $^1$H-NMR (400 MHz, CDCl$_3$) δ 9.20 (d, J=2.4 Hz, 1H), 8.16 (d, J=2.4 Hz, 1H), 8.06 (d, J=8.4 Hz, 1H), 7.79 (d, J=16 Hz, 1H), 6.63 (d, J=16 Hz, 1H), 4.27 (q, J=7.2 Hz, 2H), 2.88 (d, J=7.2 Hz, 2H), 2.29 (m, 1H), 1.32 (t, J=7.2 Hz, 3H), 0.94 (d, J=6.8 Hz). $^{13}$C-NMR S (500 MHz, CDCl3) 167.4, 166.3, 156.3, 152.2, 140.4, 136.9, 135.7, 127.8, 123.9, 120.8, 120.4, 60.8, 48.4, 29.2, 22.5, 14.3. HRMS calcd for [M+H]$^+$ 284.15, found 285.15990.

(E)-3-(7-Isobutylnaphthyridin-3-yl)acrylic acid (Compound 24). (E)-3-(7-Isobutylnaphthyridin-3-yl)acrylate (42 mg, 0.148 mmol) was dissolved in THF (1.2 mL) at room temperature before 1 M LiOH (1.2 mL) was added dropwise with a syringe. The reaction stirred vigorously for one hour and was the brought to pH of 5 with 1 M HCl before being diluted with EtOAc (10 mL) and water (30 mL) The aqueous layer was extracted with EtOAc (3×10 mL). The organic layers were combined, washed with brine, dried over anhydrous Na$_2$SO$_4$(10 g), filtered over cotton and concentrated in vacuo to yield a white solid (34 mg, 77%). $^1$H-NMR (500 MHz, MeOD) δ 9.35 (d, J=1.5 Hz, 1H), 8.61 (d, J=2 Hz, 1H), 8.38 (d, J=8.5 Hz, 1H), 7.89 (d, J=16 Hz, 1H), 7.58 (d, J=8.5 Hz, 1H), 6.82 (d, J=16.5 Hz, 1H), 2.92 (d, J=7.5 Hz, 2H), 2.28 (m, 1H), 1.00 (d, J=6.5 Hz). $^{13}$C-NMR S (500 MHz, MeOD) 168.6, 156.6, 153.6, 141.6, 139.4, 137.7, 129.9, 125.3, 122.7, 122.3, 47.9, 30.5, 22.8. HRMS calcd for [M+H]$^+$ 256.12, found 257.12857.

2,5-Dioxopyrrolidin-1-yl (E)-3-(7-isobutylnaphthyridin-3-yl)acrylate. Compound 24 (24 mg, 0.093 mmol) was used crude and diluted in acetonitrile (1 mL). Triethylamine (39 μL, 0.279 mmol) was added to the suspension, dissolved the acid, and the reaction mixture was brought to 0° C. Once at temperature, N,N,N',N'-tetramethyl-O-(N-succinimidyl)uranium tetrafluoroborate (31 mg, 0.102 mmol) was added and the reaction stirred from 0° C. to room temperature over two hours. The crude reaction mixture was concentrated in vacuo, re-dissolved in DCM, and purified by flash chromatography on silica gel using 1% MeOH in DCM to afford a white solid (26 mg, 79%). $^1$H-NMR (400 MHz, CDCl$_3$) δ 9.23 (d, J=2 Hz, 1H), 8.25 (d, J=2.4 Hz, 1H), 8.10 (d, J=8.4 Hz, 1H), 8.04 (d, J=16 Hz, 1H), 7.38 (d, J=8.4 Hz, 1H), 6.80 (d, J=16 Hz, 1H), 2.90 (d, J=7.2 Hz, 2H), 2.84 (s, 4H), 2.28 (m, 1H), 0.95 (d, J=6.8 Hz. 6H). $^{13}$C-NMR (500 MHz, CDCl$_3$) δ 169.2, 168.4, 161.6, 156.9, 152.2, 145.8, 137.3, 137.0, 126.9, 124.3, 120.5, 114.2, 48.6, 38.7, 29.3, 22.7. HRMS calcd for [M+H]$^+$353.14, found 354.14688.

(E)-3-(7-Isobutylnaphthyridin-3-yl)acrylamide (Compound 23). 2,5-Dioxopyrrolidin-1-yl (E)-3-(7-isobutylnaphthyridin-3-yl)acrylate (25 mg, 0.071 mmol) was added to reaction vessel and brought to 0° C. before ammonia solution (0.5 M in dioxane, 1.5 mL) was added dropwise while stirring. The reaction mixture stirred to room temperature over four hours before it was concentrated in vacuo, and purified by flash chromatography on silica gel using 5% MeOH in DCM to yield an off-white solid (15 mg, 81%). $^1$H-NMR (400 MHz, DMSO) δ 9.22 (d, J=2.4 Hz, 1H), 8.56 (d, J=2.4 Hz), 8.38 (d, J=8.4 Hz, 1H), 7.66 (br s, 1H), 7.63 (d, J=16 Hz, 1H), 7.56 (d, J=8.4 Hz, 1H), 7.24 (br s, 1H), 6.91 (d, J=16 Hz), 2.85 (d, J=7.6 Hz, 2H) 2.24 (m, 1H), 0.94 (d, J=6.8 Hz, 6H). $^{13}$C-NMR (500 MHz, MeOD) δ 169.9, 168.4, 156.5, 153.1, 139.3, 138.2, 137.6, 130.2, 125.3, 124.5, 122.3, 30.5, 26.2, 22.8. HRMS calcd for [M+H]$^+$ 255.14, found 256.14444.

3-(7-Isobutylnaphthyridin-3-yl)propenamide (Compound 25). Compound 23 was dissolved in MeOH (7 mL) and the reaction mixture was brought to 0° C. Palladium hydroxide (2 mg, 0.017 mmol) was added to the reaction mixture while stirring. Hydrogen was bubbled through the reaction using a balloon as it stirred to room temperature over four hours. The reaction mixture was filtered over celite, concentrated in vacuo, and purified by flash chromatography on silica gel using 15% MeOH in DCM to afford a white solid (10 mg, 45%). $^1$H-NMR (500 MHz, MeOD) δ 8.93 (d, J 1.5 Hz, 1H), 8.27 (d, J=8 Hz, 1H), 8.20 (d, J=1 Hz, 1H), 7.51 (d, 8.5 Hz, 1H), 3.16 (t, J=7.5 Hz, 2H), 2.89 (d, 7.5 Hz, 2H), 2.65 (t, J=7.5 Hz, 2H), 2.24 (m, 1H), 0.98 (d, J=6.5 Hz, 6H). $^{13}$C-NMR (500 MHz, MeOD) δ 166.9, 155.5, 155.3, 138.6, 137.2, 136.2, 124.7, 122.3, 47.9, 37.3, 30.5, 29.4, 22.8. HRMS calcd for [M+H]$^+$ 257.15, found 258.15970.

Compounds 26, 27, and 28

Compounds 26, 27, and 28 were synthesized from commercially available methyl-3-formyl-4-nitrobenzoate. The nitro group of the starting material was reduced to generate the amine, and a subsequent Friedlander reaction with 5-methylcyclohexane-1,3-dione was performed. Base-mediated deprotection yielded the carboxylic acid intermediate Compound 26. Installation of an N-hydroxysuccinimide onto the ester enabled conversion to the amide Compound 27. The final Compound 28 was isolated following a reduction with lithium aluminum hydride in 70% yield.

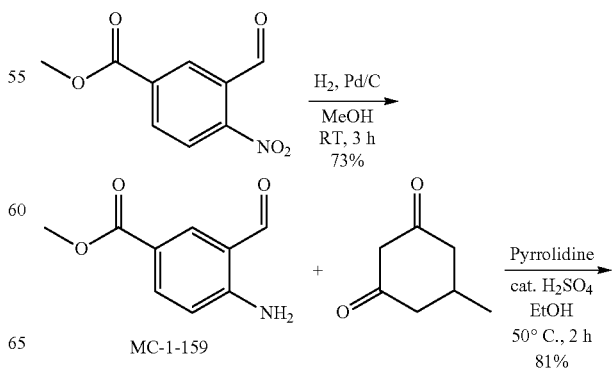

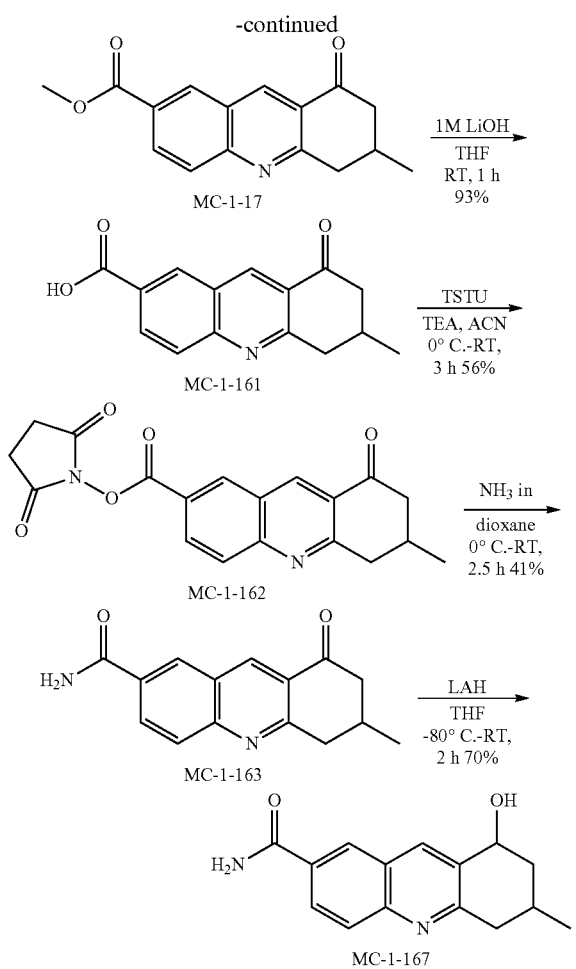

Methyl 6-methyl-8-oxo-5, 6, 7, 8-tetrahydroacridine-2-carboxylate. Methyl-4-amino-formylbenzoate (99 mg, 0.558 mmol) was dissolved in EtOH (1 mL). While stirring at 50° C., pyrrolidine (50 µL, 0.614 mmol) and concentrated sulfuric acid (9 µL, 0.167 mmol) were added to the reaction, followed by 5-methylcyclohexane-1,3-dione (77 mg, 0.614 mmol). At five hours, the reaction was concentrated in vacuo and the resulting light brown oil was re-dissolved in DCM and purified by flash chromatography on silica gel using 20% EtOAc in hexanes to yield as a white solid (120 mg, 81%). $^1$H-NMR (400 MHz, CDCl$_3$) δ 8.93 (s, 1H), 8.70 (d, J=1.6 Hz, 1H), 8.39 (d, J=1.6 Hz, 8.8 Hz, 1H), 8.10 (d, J=8.8 Hz, 1H), 4.01 (s, 1H), 3.43 (dd, J=3.6 Hz, 15.2 Hz, 1H), 3.03 (dd, J=10.8 Hz, 16.8 Hz, 1H), 2.91 (m, 1H), 2.51 (m, 2H), 1.25 (d, J=6.4 Hz, 3H). $^{13}$C-NMR (400 MHz, CDCl$_3$) δ 166.2, 163.7, 138.1, 132.8, 131.7, 129.0, 128.4, 126.4, 126.0, 52.6, 47.0, 41.8, 28.9, 21.3. HRMS calcd for [M+H]$^+$ 270.11, found 270.11295.

6-Methyl-8-oxo-5,6,7,8-tetrahydroacridine-2-carboxylic acid (Compound 26). Methyl 6-methyl-8-oxo-5, 6, 7, 8-tetrahydroacridine-2-carboxylate (55 mg, 0.204 mmol) was dissolved in THF (1.5 mL) at room temperature before 1 M LiOH (1.5 mL) was added dropwise with a syringe. The reaction stirred vigorously for one hour and was the brought to pH of 5 with 1 M HCl before being diluted with EtOAc (20 mL) and water (45 mL) The aqueous layer was extracted with EtOAc (3×20 mL). The organic layers were combined, washed with brine, dried over anhydrous Na$_2$SO$_4$(15 mg), filtered over cotton and concentrated in vacuo to yield a reddish solid (51 mg, 93%). $^1$H-NMR (400 MHz, DMSO) δ 9.04 (s, 1H), 8.84 (d, J=2 Hz, 1H), 8.29 (dd, J=2, 8.8 Hz, 1H), 8.06 (d, J=9.2 Hz), 3.27 (t, J=2.4 Hz, 1H), 3.27 (t, J=2.4 Hz, 1H), 3.06 (dd, J=16.8, 10.4 Hz, 1H), 2.81 (m, 1H), 2.61 (dd, J=16.4, 11.2 Hz, 1H), 2.45 (m, 1H), 1.14 (d, J=6.8 Hz, 3H). $^{13}$C-NMR (400 MHz, DMSO) δ 197.1, 166.7, 163.8, 150.5, 137.4, 132.8, 131.3, 128.6, 128.4, 126.1, 125.7, 46.2, 40.8, 28.1, 20.8. HRMS calcd for [M+H]$^+$ 255.09, found 256.09639.

2,5-Dioxopyrrolidin-1-yl-6-methyl-8-oxo-5,6,7,8-tetrahydroacridine-2-carboxylate. Compound 26 was used crude and diluted in acetonitrile (1 ML). Triethylamine (66 µL, 0.470 mmol) was added to the suspension, dissolved the acid, and the reaction mixture was brought to 0° C. Once at temperature, N,N,N',N'-tetramethyl-O-(N-succinimidyl)uranium tetrafluoroborate (52 mg, 0.172 mmol) was added and the reaction stirred from 0° C. to room temperature over three hours. The crude orange reaction was concentrated in vacuo, re-dissolved in DCM, and purified by flash chromatography on silica gel using 1% MeOH in DCM to afford a white solid (31 mg, 56%). $^1$H-NMR (500 MHz, CDCl$_3$) δ 8.96 (s, 1H), 8.85 (d, J=1.5 Hz, 1H), 8.42 (dd, J=1.5, 8.5 Hz, 1H), 8.21 (d, J=8.5 Hz, 1H), 3.50 (d, J=14 Hz, 1H), 3.09 (dd, J=10, 17 Hz, 1H), 2.95 (S, 4H), 2.91 (s, 1H), 2.52 (m, 2H), 1.26 (d, J=6 Hz, 3H). $^{13}$C-NMR (500 MHz, CDCl$_3$) δ 169.4, 165.0, 161.2, 151.8, 138.5, 134.6, 131.5, 129.4, 126.9, 126.0, 46.8, 41.5, 29.7, 28.7, 25.7, 21.2. HRMS calcd for [M+H]$^+$ 352.11, found 353.11266.

6-Methyl-8-oxo-5,6,7,8-tetrahydroacridine-2-carboxamide (Compound 27). 2,5-Dioxopyrrolidin-1-yl-6-methyl-8-oxo-5,6,7,8-tetrahydroacridine-2-carboxylate (29 mg, 0.083 mmol) was added to reaction vessel and brought to 0° C. before ammonia solution (0.5 M in dioxane, 1.2 mL) was added dropwise while stirring. The reaction mixture stirred to room temperature over two hours before it was concentrated in vacuo, and purified by flash chromatography on silica gel using 1% MeOH in DCM to yield an off-white solid (9 mg, 41%). $^1$H-NMR (500 MHz, DMSO) δ 8.90 (s, 1H), 8.68 (s, 1H), 8.28 (d, J=8.8 Hz, 1H), 8.20 (br s, 1H), 8.05 (d, J=8.8 Hz, 1H), 7.62 (br s, 1H), 3.05 (dd, J=10.5, 16 Hz, 1H), 2.80 (d, J=16.5 Hz, 1H), 2.58 (m, 2H), 2.36 (br s, 1H), 1.14 (d, J=6 Hz, 3H). $^{13}$C-NMR (400 MHz, DMSO) δ 197.7, 172.7, 167.1, 163.0, 137.1, 132.3, 130.7, 130.0, 127.8, 126.0, 125.5, 46.1, 28.1, 25.2, 20.8. HRMS calcd for [M+H]$^+$ 254.11, found 255.11254.

8-Hydroxy-6-methyl-5,6,7,8-tetrahydroacridine-2-carboxamide (Compound 28). Compound 27 (11 mg, 0.043 mmol) was dissolved in THF (500 µL) and the reaction was cooled to −80° C. in a dry ice/isopropanol bath. LiAlH$_4$ (2 mg, 0.052 mmol) was added at −80° C. The reaction was stirred at −80° C. for 10 minutes, was transferred to an ice bath, and then warmed to room temperature over three hours. Once complete, it was filtered over celite, concentrated in vacuo, and purified by flash chromatography on silica gel using 10% MeOH in DCM to yield an off-white solid (8 mg, 70%). $^1$H-NMR (400 MHz, DMSO) δ 8.46 (d, J=1.6 Hz, 1H), 8.40 (s, 1H), 8.14 (br s, 1H), 8.10 (dd, J=2, 8.8 Hz, 1H), 7.91 (d, J=8.8 Hz, 1H), 7.51 (s, 1H), 4.80 (m, 1H) 3.17 (m, 1H), 2.65 (dd, J=11.6, 18 Hz, 1H), 2.15 (m, 2H) 1.44 (q, J=11.6 Hz, 1H), 1.11 (d, J=6.8 Hz, 1H). $^{13}$C-NMR (400 MHz, DMSO) δ 167.5, 159.9, 147.4, 135.9, 134.1, 131.1, 127.7, 127.4, 125.9, 67.3, 41.5, 41.1, 26.7, 22.1. HRMS calcd for [M+H]$^+$ 256.12, found 257.12850.

Methods

SULT1A3 DNA constructs. Wild-type and mutant SULT1A3 coding regions were inserted into a pGEX-6P expression vector that fuses a triple-tag (N-His/GST/MBP)

PreScission protease cleavable protein to the SULT1A3 N-terminus (17). Mutated coding regions were constructed using PCR mutagenesis and confirmed by DNA sequencing.

SULT1A3 Expression and Purification. *E. coli* (BL21 (DE3)) containing the SULT1A3 expression plasmid were grown at 37° C. in LB medium (17). At OD600~0.6, the culture was temperature shifted to 17° C. in an ice/water bath. Upon reaching 17° C., IPTG was added (0.30 mM) and the culture was incubated at 17° C. for 18 hours. Cells were then pelleted and resuspended in lysis buffer (PMSF (290 μM), pepstain A (1.5 μM), lysozyme (0.10 mg/ml), EDTA (2.0 mM), KCl (400 mM), $K_2PO_4$ (50 mM), pH 7.5). The suspension was sonicated and then centrifuged (10,000 g, 1.0 hr, 4° C.). $MgCl_2$ (5.0 mM) was added to chelate EDTA before passing the solution through a Chelating Sepharose Fast Flow column charged with Ni2+. The column was washed (imidazole (10 mM), KCl (400 mM), and $KPO_4$ (50 mM), pH 7.5), enzyme was eluted (imidazole (250 mM), KCl (400 mM), and $KPO_4$ (50 mM), pH 7.5) and loaded directly onto a Glutathione Sepharose column. The GST column was washed (DTT (2.0 mM), KCl (400 mM), and $KPO_4$ (50 mM), pH 7.5) before eluting the tagged enzyme (reduced glutathione (10 mM), DTT (2.0 mM), KCl (400 mM), and Tris (100 mM), pH 8.0). The fusion protein was digested overnight at 4° C. using PreScission Protease, and passed through a GST column to remove the tag. The protein was ≥95% pure as judged by SDS-PAGE, and its concentration was determined by UV absorbance (£280=53.9 mM-1 cm$^{-1}$). The protein was then concentrated, flash frozen and stored at −80° C.

Covalent Tagging of SULT1A3 Cys Constructs. Labeling of the SULT1A3 Cys constructs was performed as described previously (17,18,21). Briefly, 3-maleimido-PROXYL (spin label) or N-cyclohexylmaleimide (diamagnetic control) was added to an enzyme containing solution at 20-fold excess over reactive Cys. Unreacted Cys was monitored using DNTB (17,18,21); reactions were considered complete when >98% of the Cys was labeled. Reaction conditions: SULT1A3 (50 μM, monomer), 3-maleimido-PROXYL or N-cyclohexylmaleimide (1.0 mM), PAP (0.50 mM), $KPO_4$ (50 mM), pH 7.5, 4±2° C. To prepare samples for NMR, reaction mixtures were dialyzed three times against 40 volumes of PAP (0.50 mM), $KPO_4$ (50 mM), pD 7.4, $D_2O$ (>95%), 4±2° C. Following dialysis, labeled enzyme was assayed to ensure that the initial-rate parameters ($k_{cat}$, $K_m$ and $K_i$) were not substantially altered by Cys insertion and labelling (see, Table B).

TABLE B

Initial-Rate Parameters for WT and Spin-Labeled SULT1A3 Mutants

| Enzyme | $k_{cat}$ (min$^{-1}$)$^b$ | $K_m$ $_{1-HP}$ (nM)$^b$ | $K_i$ $_{CMP8}$ (nM) |
|---|---|---|---|
| WT | 120 (17)$^c$ | 82 (3) | 34 (3) |
| 116$^a$ | 110 (18) | 87 (3) | 37 (3) |
| 198 | 108 (11) | 88 (2) | 46 (5) |
| 234 | 109 (15) | 84 (3) | 31 (2) |

$^a$Cys residue at which spin label is attached.
$^b$$k_{cat}$ and $K_m$ were determined at saturating PAPS (500 μM, 17 × $K_m$).
$^c$Values in parentheses indicate one standard deviation.

NMR Studies. NMR experiments were performed using a Bruker 600 MHz spectrometer equipped with a TCI H/F-cryogenic probe at 298° K. Compound 8 (CMP8) peak assignments were determined from 1D-proton and -carbon spectra using $^1H$-$^{13}C$ Heteronuclear Single Quantum Coherence (HSQC) (22) and Heteronuclear Multiple Bond Correlation (HMBC) (22) sample composition: CMP8 (1.9 mM), TMS (0.5 mM), DMSO (0.5 mM), D20≥99%, and temperature 25±1° C. The sample composition in the line-broadening studies: labelled SULT1A3 (20 μM active sites), CMP8 (100, 200, 400, or 1000 μM), PAP (500 μM, 17×$K_d$), $KPO_4$ (50 mM), pD 7.4, 25±1° C. Proton line-widths were fit to a Lorentzian distribution using NMRdraw (23).

NMR-Distance Constrained Molecular Dynamics Modeling. A ligand-free homology model of SULT1A3 was constructed from the SULT1A3•PAP•dopamine structure (PDB 2A3R (8)) using SWISS-MODEL. The model was protonated at pH 7.4 and energy minimized using GROMACS.

AMBER energy-parameter files were constructed using Antechamber (24) for CMP8, PAPS, and a spin-labeled cysteine analogue in which the nitroxyl-moiety was replaced by a hydroxyl group. The cysteine analogue parameter file was added to the AMBER energy file as a non-canonical amino acid and inserted into SULT1A3 by replacing residues Q116, E198, and K234. PAPS was positioned in the active site of the ligand-less enzyme using GOLD. The system was equilibrated (298° K, NaCl (50 mM), pH 7.4) in 100 psec increments using GROMACS. Once equilibrated, CMP8 was positioned randomly in a simulated box of water (52×52×52 Å) containing the spin-labelled SULT1A3•PAPS construct, and docked using GROMACS. Docking was constrained using NMR determined, spin-label/CMP8-proton distances as described in the main text (see, NMR-distance constrained MD docking). The docking simulations were repeated 100 times, 92 of the docking experiments yielded the structure described in the main text, 8 showed a reversed orientation.

Molecular Dynamics Docking. Docking of CMP8 and its analogues was performed using a previously described equilibrated model of the SULT1A3•PAPS•dopamine complex without spin label (17). Briefly, compounds were positioned in the NMR-determined allosteric-binding site using GOLD, minimized with GROMACS (AMBER energy field) and equilibrated in 100 psec increments at 298° K, NaCl (50 mM), pH 7.4. Once the RMSD of the system had stabilized, indicating equilibrium had been reached, equilibrium was confirmed by ensuring that the RMSD remained stable over an additional 1.0 nsec.

Initial-Rate Studies. Initial-rate parameters for the labeled or mutant SULT1A3 constructs were determined using a previously described 1-HP assay (25). Briefly, reactions were initiated by addition of PAPS (0.50 mM, 17×Km) to a solution containing enzyme (20 nM, active sites), 1-HP (2.0 μM, ~24×Km), and $KPO_4$ (50 mM), pH 7.5, 25±2° C. Reactions were monitored via fluorescence change associated with the conversion of 1-HP to 1-HP-S ($\lambda_{ex}$=325 nm, $\lambda_{em}$=370 nm). $K_{eq}$ for the 1-HP sulfonation reaction is ~250. Given the reaction conditions outlined above, ≥99% of 1-HP is converted to 1-HP-S, and ~0.4% of PAPS is converted to PAP at equilibrium. The affinities of PAPS and PAP for SULT1A3 are comparable, and the affinity of 1-HP-S is quite low ($K_d$=240±30 μM); consequently, the conditions result in quantitative conversion of 1-HP to 1-HP-S with negligible product inhibition. Reaction progress curves were analyzed to obtain initial-rate parameters as described previously (26,27).

Inhibition studies. Inhibition parameters were determined under conditions identical to those described above (see, Initial-Rate Studies) except that [1-HP] was increased to 5.0 μM (~61×Km) and inhibitor concentration was varied between 0.20-20×$K_i$. $K_i$ was obtained using a least-squares fit to the following partial inhibition equation (25,28):

$v=k_{cat} \cdot (K_i+(1/kcat\ inh)\cdot[I])/(K_i+[I])$, where $k_{cat\ inh}$ is enzyme turnover at saturating substrates and allosteric inhibitor.

Equilibrium Binding Studies. In all cases, ligand binding to SULT1A3 was monitored via changes in the intrinsic fluorescence of the enzyme ($\lambda_{ex}$=290 nm, $\lambda_{em}$=340 nm). Conditions: SULT (50 nM, active sites), KPO4 (50 mM), pH 7.5, 25±2° C. Titrations were performed in triplicate. Data were averaged and least-squares fit using a model that assumes a single binding site per monomer (29-31). Ligand concentration was varied from 0.10-40×$K_d$.

Pre-Steady State Binding Studies. The pre-steady state binding of PAP to SULT1A3 was monitored via ligand-induced enzyme fluorescence changes in SULT1A3 using an Applied Photophysics SX20 stopped-flow spectrofluorimeter (32). Fluorescence was measured at $\lambda_{ex}$ 290 nm and $\lambda_{em}$≥330 nm (using a cutoff filter). $k_{on}$ and $k_{off}$ of PAP binding to SULT1A3 were obtained by rapidly mixing (1:1, v:v) a solution containing SULT1A3 (25 nM, dimer), CMP8 (0 or 1.7 µM, 50×$K_d$), $KPO_4$ (50 mM), pH 7.5 with a solution that was identical except that it contained PAP (0.5, 1.0, 1.5, or 2.0 µM) and did not contain enzyme. All reactions were pseudo first order in [PAP]. The observed rate constant ($k_{obs}$) at a given [PAP] was taken as the average of three independent progress curves each obtained from a single-exponential fit of 6-9 averaged, binding progress curves. The rate constants, $k_{on}$ and $k_{off}$, were obtained from the slopes and intercepts predicted by linear least-squares analysis of four-points $k_{obs}$ vs [PAP] plots.

Results and Discussion

Discovering the Site. SULTs harbor two physically distinct, non-interacting allosteric binding sites the so-called catechin- and NSAID-binding sites (18, 21). The residues that line these sites differ in each SULT isoform, which begs the hypotheses that the sites evolved to enable isoforms to communicate with metabolites within their metabolic domains. This hypothesis was born out using the SULT1A3 isoform (18).

Figure 1:
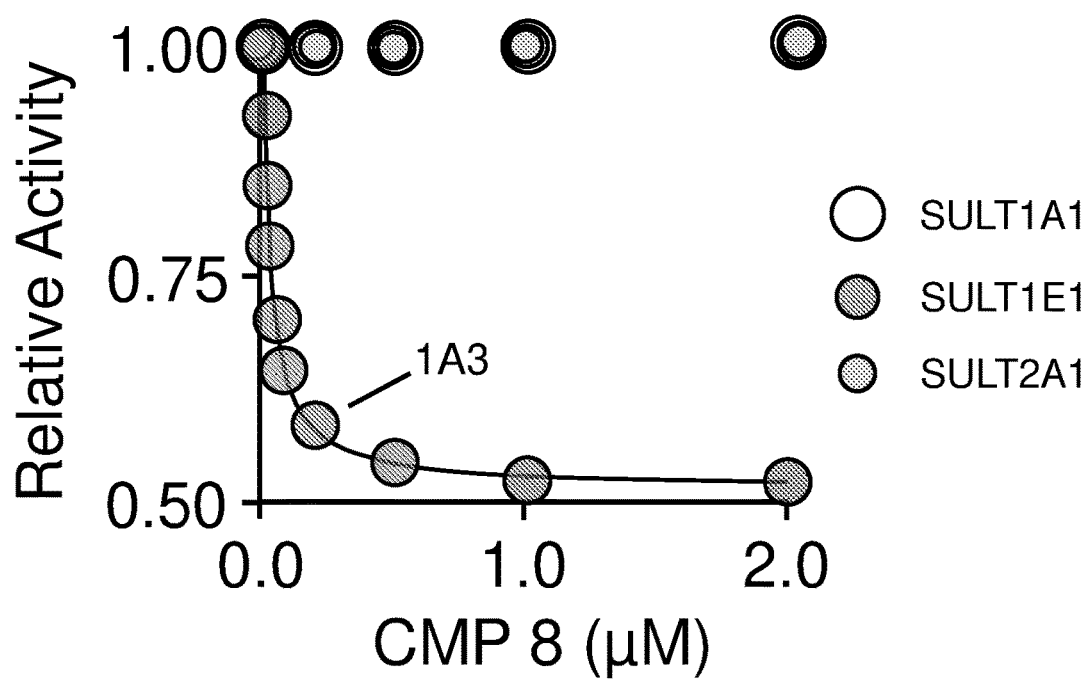
FIG. 1 shows inhibition of SULT isoforms by Compound 8 ("CMP8"). The initial rates of SULT catalyzed 1-HP sulfonation are plotted as a function of inhibitor concentration, and are normalized relative to [inhibitor]=0. Enzyme activity was monitored by the sulfonation dependent change in 1-HP fluorescence ($\lambda_{ex}$=325 nm, $\lambda_{em}$=370 nm). Less than 5% of the concentration-limiting substrate converted at the reaction endpoint was consumed during initial-rate measurements. Each point is the average of three independent determinations. Conditions: SULT (20 nM, active sites), PAPS (0.50 mM, 17×$K_m$), 1-HP (5.0 μM, 61×$K_m$), KPO$_4$ (50 mM), pH 7.5, 25±2° C.

While testing the initial-rate inhibition characteristics of compounds designed to inhibit SULT1A3 by binding at its catechin site, a high-affinity, high-specificity inhibitor that did not appear to bind either of the known sites was discovered—Compound 8 (CMP8). The potency and specificity of CMP8 are demonstrated in FIG. 1. The $K_i$ of CMP8 for SULT1A3 is 34 nM, and CMP8 does not detectably inhibit the other major SULT isoforms found in liver and brain at concentrations as high as 2 mM. CMP8 proved to be a partial inhibitor—at saturation, its binding reduces SULT1A3 turnover to 46% of that in the absence of inhibitor. Such inhibitors alleviate inhibition when used competitively against total inhibitors that bind at the same site. CMP8 did not alleviate inhibition by epigallochatechin gallate or mefenamic acid—near-total inhibitors that bind the catechin and NSAID sites, respectively (19,20). Given these favorable characteristics, it was reasoned that the CMP8-binding site offered a new target that could be used to control 1A3 activity. Consequently, the solution structure of the CMP8-binding site was determined using spin-label-triangulation NMR. As used herein, the "CMP8-binding site" refers to the SULT1A3 allosteric site defined herein, which is different from the catechin- and NSAID-binding sites.

Structure Determination. A method (Spin-Label-Triangulation NMR, SLT NMR) was developed that allows the solution structure of a SULT ligand-binding pocket to be determined without the use of high-resolution NMR or crystallography, and regardless of the molecular mass of the protein (18-20). The method relies on the distance-dependent line broadening of peaks in the ligand's solution 1D-NMR spectrum, which occurs when a ligand docks within ~25 Å of a spin label covalently attached to the protein. Using three spatially well separated spin labels, it is possible to triangulate the position of each ligand proton with respect to the protein surface. Spin label insertion sites are identified by first screening for line-broadening effects using a previously define set of six sites that when spin labelled coat the entire surface of the SULT dimer in a paramagnetic field of sufficient strength to broaden the NMR linewidth of the ligand regardless of where it binds (18). Based on the findings of the screen, the spin-label insertions sites can then be optimized as needed (20). It is critical that the initial-rate and inhibition parameters of the spin-labelled protein closely match those of the native protein (see, Table B). Having positioned ligand protons on the protein surface, the structure is then refined using NMR-distance constrained molecular dynamics docking.

Distance Measurements. The distance dependence of the magnetic interactions between an unpaired electron and a nuclear spin are well understood (21-23). Given the effect of an unpaired electron spin on the linewidth of a ligand nucleus ($R_2$), inter spin distances can be calculated using the Solomon-Bloembergen equation (21). The $^1$H-NMR linewidths of protein-bound ligands are typically too broad to measure directly; however, the line-broadening effect of the electron can be obtained from a ligand's solution spectrum if the frequency of ligand exchange between bulk solution and the protein is comparable to, or greater than the difference in the resonant frequencies of the free and bound ligand (21-23). In such cases, solution linewidths provide observed transverse relaxation rates, $R_{2obs}$, that depend linearly on the fraction of bound ligand, $F_B$, according to equation 1, where $R_{2B}$ and $R_{2F}$ are the transverse relaxation rates for bound and free protons, and $R_{2ex}$ is the chemical exchange contribution to the relaxation (21).

$$R_{2\ obs}=(R_{2B}-R_{2F})F_B+R_{2F}+R_{2ex} \qquad (1)$$

$R_{2\ obs}$ contains contributions from both protein-nuclei and the unpaired-electron spins (18-20,23). To isolate the contribution of the electron, a diamagnetic control is created for each spin-labeled construct in which the paramagnetic (PROXYL) moiety of the spin label is replaced with a diamagnetic homologue (i.e., a cyclohexyl moiety). The contribution of the unpaired electron is obtained by subtracting the slopes of the paramagnetic and diamagnetic $R_{2\ obs}$ vs $F_B$ plots.

Figure 2:
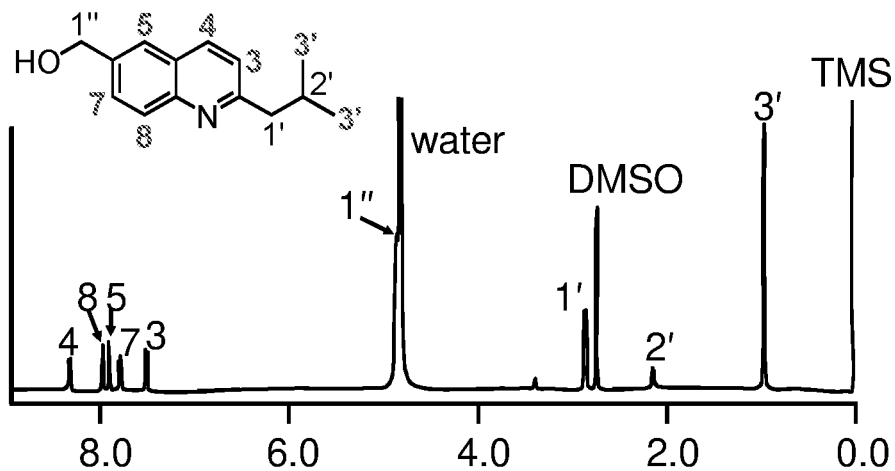
FIG. 2 shows NMR measurements.
Figure 2:
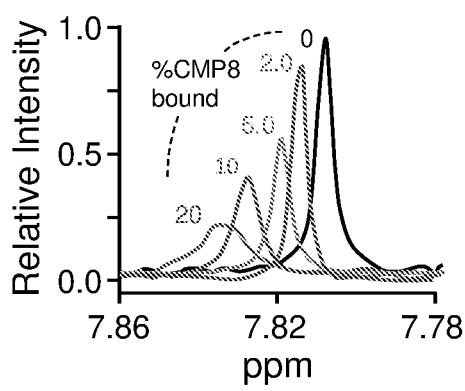
Figure 2:
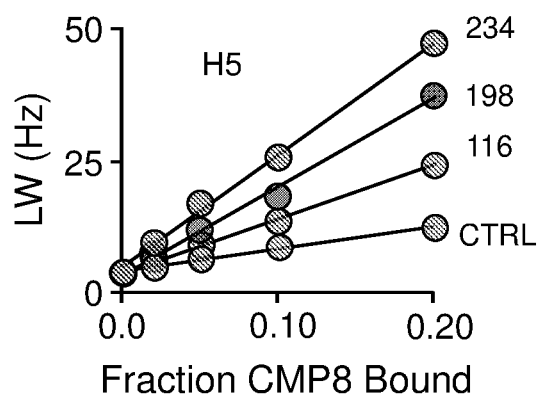

A representative study characterizing the interaction of the C5-proton of CMP8 with the three spin-labelled constructs and diamagnetic control is presented in FIG. 2. The study was performed at saturating concentrations of CMP8 and PAP (see, FIG. 2). The structure of CMP8 and its associated $^1$H-NMR spectrum and peak assignments are shown in Panel A. The line broadening of the C5-peak as a function of the percent of bound CMP8 is shown in Panel B. The construct used in the Panel B study was spin-labelled at position 234. The line widths obtained from the Panel-B spectra are plotted vs fraction-CMP8-bound in Panel C (red dots). Similar studies were performed for the remaining two spin-labelled constructs (positions 198 and 116) and diamagnetic control (CTRL). As discussed above, the slope associated with the diamagnetic control was subtracted from those of the spin-labelled constructs to obtain the contribution of the spin-label unpaired electron to the line broadening of the C5 proton, which was then used to calculate distances. Similar studies were performed on the C3, C3', C4, C7 and C8 protons (see, FIG. 6). The inter-spin distances from each proton to each of the three spin labels are compiled, along with the measurement errors, in Table B.

NMR-distance constrained MD docking. Each NMR determined distance represents a vector between the time-averaged position of the spin-label oxygen (calculated using GROMACS) and the given proton. Three such vectors are associated with each proton, each originates at the oxygen of a different spin-label, and all three intersect at the proton. The errors associated with these three measurements constitute an error ellipsoid that centers on the proton and whose principal axis magnitudes are given by the standard errors (±1 s) of the NMR measurements. Docking is constrained by applying a 50 kJ mole$^{-1}$ Å$^{-1}$ restoring force (using distance_restraints, GROMACS (24,25)) that drives the proton toward the ellipsoid center if any part of its van der Waals surface lies outside the ellipsoid; the restoring force inside the ellipsoid is zero. As is appropriate for NMR spin-spin interaction measurements (21,26,27), distance_restraints was parameterized to utilize time-averaged (1/r$^6$)-weighted restraints. The motions of all six CMP8 protons (H3, H3', H4, H5, H7 and H8) were constrained simultaneously during docking. Docking was repeated 100 times; identical structures were achieved 92 times, and the structures did not change once the distance constraints were removed.

The Refined Structure. The energy minimized, NMR-distance-constrained structure of the CMP8•E• PAPS• dopamine complex is presented in FIGS. 3A and 3B, and is available at www.modelarchive.org, archive number ma-qtj80. Panel A provides an at-a-distance view of the complex and reveals that CMP8 binds in a crux of the protein where the cap helix connects to the base. While the majority of residues that are in direct contact with CMP8 reside in the base, CMP8 directly contacts the cap at residue 235. The residues linearly aligned along the left-facing edge of the cap helix (FIG. 3A) either directly contact CMP8 or layer immediately over direct-contact residues—these interactions likely contribute to the CMP8-induced cap stabilization. Panel B offers a more detailed view of the CMP8 interactions. The quinonoid base of CMP8 is engaged in p-stacking interactions with planar residues (F222 and H226) on both of its faces. A hydrophobic interaction with L67 anchors the CMP8 isobutyl-moiety and is geometrically positioned such that CMP8 can hydrogen bond with Q225.

Confirming the Structure. The structure was validated by testing its ability to predict the consequences of mutations on the initial-rate parameters of the enzyme. The effects of binding-site mutations on the initial rate parameters of SULT1A3 are compiled in Table B. Consistent with the structure, replacing the isobutyl moiety of L67 with a proton (L67G) results in a significant (5.3-fold) increases in $K_{i\ CMP8}$, and replacing the planar moieties at positions 226 and 222 with methyl groups (F222A, H226A) causes a significantly greater (60-fold) increase in $K_{i\ CMP8}$. With one exception (N71H), the SULT1A3 residues that directly contact CMP8 are identical to those of its evolutionary precursor, SULT1A1 (9). Reconstructing the SULT1A1 pocket in the SULT1A3 scaffold, by replacing Asn71 with His, caused $K_{i\ CMP8}$ to increase beyond the detectible limit (i.e., no inhibition detected at 100 mM CMP8); thus, this single residue swap appears to determine the CMP8-specificity of the isoform. In conclusion, the mutagenesis data fully support the structure.

It is notable that while the allosteric-site mutations affect $K_{i\ CMP8}$, they do not alter other initial-rate parameters, including turnover at saturating inhibitor ($k_{cat\ inh}$). Thus, the mutations weaken the CMP8's affinity, but do not affect the linkages that couple CMP8 binding to turnover—these linkages must lay elsewhere in the cavity.

The Mechanism of Inhibition. SULTs harbor an approximately 30-residue active-site cap that must isomerize between open and closed states during the catalytic cycle (28-32). The cap isomerization equilibrium constant ($K_{iso}$) is defined as the ratio of the closed-to-open forms of the cap, and is a function of bound ligand (29-33). Nucleotide binding causes the cap to move from a largely open ($K_{iso} \leq 0.1$) to largely closed ($K_{iso} \sim 20$) configuration. Cap stabilization by PAP or PAPS is virtually identical, and neither acceptors nor their sulfates detectably influence cap closure regardless of whether nucleotide is bound. Cap closure encapsulates the nucleotide, which can release only from a cap-open form (28,29). For all isoforms studied thus far (18,31-33), nucleotide release is rate determining (34,35) and the release rate depends on $K_{iso}$, which determines the fraction of enzyme-bound PAP poised for escape.

Given that CMP8 interacts with the SULT1A3 cap, it was reasoned it might inhibit by stabilizing the cap-closed form(s) of the enzyme. To test this hypothesis, the microscopic rate constants for nucleotide binding and release were determined in the presence and absence of saturating CMP8. The binding reactions were monitored via intrinsic fluorescence changes associated with ligand binding (30-32) (see, Methods). The resulting $k_{obs}$ vs [PAP] plots are presented in FIG. 4. $k_{on}$ and $k_{off}$ are obtained, respectively, from the slopes and intercepts of the plots (30,31), see Table C. As can be seen, saturation with CMP8 does not detectibly alter the slopes, but decreases the intercepts by a factor of 0.41 (±0.05). Thus, CMP8 does indeed slow nucleotide release by increasing $K_{iso}$ and thus stabilizing the closed form of the cap. Notably, the effect of CMP8 on the ratio of the nucleotide off-rate constants ($k_{off\ (+CMP8)}/k_{off\ (-CMP8)} = 0.41$ (±0.05)) is comparable to its effect on the $k_{cat}$ ratio ($k_{cat\ (+CMP8)}/k_{cat\ (-CMP8)} = 0.46 \pm 0.08$)—a coincidence that strongly supports that nucleotide release is rate determining and that turnover is controlled by $K_{iso}$.

TABLE C

Rate Constants Governing Nucleotide Binding to SULT1A3

| | (−) CMP8 | | (+) CMP8 | |
|---|---|---|---|---|
| Nucleotide | $k_{on}$ (μM$^{-1}$s$^{-1}$) | $k_{off}$ (s$^{-1}$) | $k_{on}$ (μM$^{-1}$s$^{-1}$) | $k_{off}$ (s$^{-1}$) |
| PAP | 6.6 (0.2)$^a$ | 2.7 (0.1) | 6.3 (0.3) | 1.1 (0.1) |

$^a$Values in parentheses indicate standard error.

Building Inhibitors. Given that 1A3 turnover is determined by the fraction of enzyme in the cap-open form, it was reasoned that further inhibition could be achieved if CMP8 were modified in ways that enhance cap closure. Toward this end, CMP8 derivatives were designed via visual inspection of GROMACS-docked structures and computational assessments of cap-stabilization. The compounds selected for synthesis and further studies are presented in Table A along with their experimentally determined $K_i$ and %-Inhibition-at-Saturation values.

All of the compounds were tested for activity with SULT1A1 and SULT1A3, as indicated in the table.). Compounds 12, 23 and 25 were also tested for inhibition of two other liver sulfotransferase, SULT1E1 and SULT2A1. At 50 uM, no inhibition was detected with any of the three compounds for SULT1E1 and SULT2A1.

Small Molecule Inhibition of Sulfotransferase 1A3

The potential for certain compounds' oral activity was assessed based on Lipinski's Rules, which include the following requirements: (1) molecular weight must be less than 500; (2) compound must have no more than five hydrogen bond donors; (3) compound must have no more than five hydrogen bond acceptors; and (4) LogP must be less than 5. Table D shows a non-limiting list of compounds following Lipinski's Rules.

TABLE D

| Structure | Molecular Weight | LogP | BBB Score |
|---|---|---|---|
| 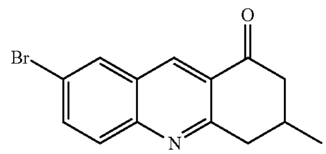 [SMILES: CC1CC(=O)c2cc3cc(Br)ccc3nc2C1] | 290.16 | 3.52 | 0.130 |
| 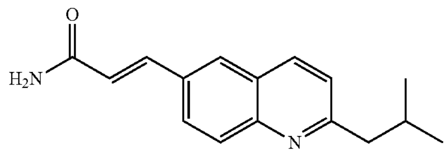 [SMILES: CC(C)Cc1ccc2cc(/C=C/C(N)=O)ccc2n1] | 254.33 | 3.30 | 0.133 |
| 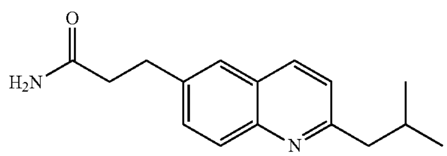 [SMILES: CC(C)Cc1ccc2cc(CCC(N)=O)ccc2n1] | 256.35 | 3.32 | 0.128 |
| 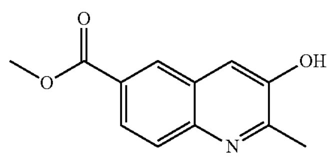 | 217.22 | 2.25 | 0.055 |
| 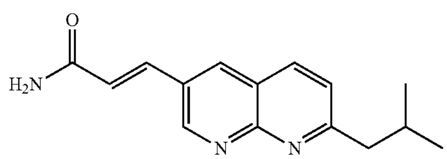 [SMILES: CC(C)Cc1ccc2cc(/C=C/C(N)=O)cnc2n1] | 255.32 | 3.17 | 0.142 |
| 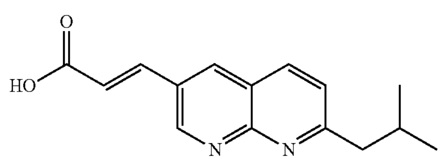 [SMILES: CC(C)Cc1ccc2cc(/C=C/C(=O)O)cnc2n1] | 256.31 | 3.82 | 0.084 |
| 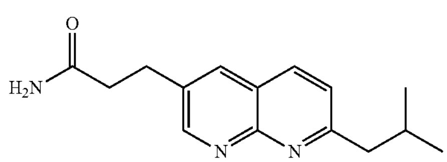 [SMILES: CC(C)Cc1ccc2cc(CCC(N)=O)cnc2n1] | 257.34 | 3.19 | 0.132 |
| 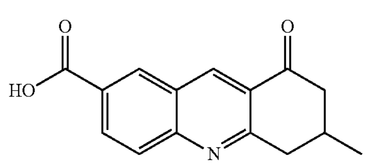 [SMILES: CC1CC(=O)c2cc3cc(C(=O)O)ccc3nc2C1] | 255.27 | 2.25 | 0.076 |
| 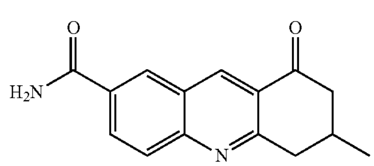 [SMILES: CC1CC(=O)c2cc3cc(C(N)=O)ccc3nc2C1] | 254.29 | 1.59 | 0.148 |

TABLE D-continued

| Structure | Molecular Weight | LogP | BBB Score |
|---|---|---|---|
| [structure: H₂N-C(=O)- attached to acridine-like ring with OH and methyl substituents] | 256.31 | 1.86 | 0.092 |

Other factors, such as whether the structure is characterized as PAINs-like (pan assay interference) compound and whether or not it is predicted to penetrate the blood brain barrier (BBB). An ideal drug will only interact with its intended target, whereas PAIN compounds are likely to interact with multiple targets, negatively impacting drug development by giving false positives in assays. An online PAINs predictor, "PAINs-Remover" (Baell, J. et al. *J. Med. Chem*, 53, 2719 (2010)) was used to determine that all of the structures presented in table D above were characterized as not PAINs-like structures via the PAINS-remover tool, thereby displaying low potential for off-target effects.

The potential for certain compounds to penetrate the blood brain barrier (BBB) was calculated. Machine learning has been utilized throughout all stages of drug discovery, including predicting the "drugability" of structures. A "BBB Predictor," which applies the support vector machine (SVM) algorithm to four fingerprints, including MACCSFP. Because the SVM and MACCSFP combination has been shown to be ideal for BBB permeability predictions, it was used to generate the BBB scores shown in table D. See Liu, H. et. al. *J. Chem. Inf. Model.* 54, 1050 (2014); Wang, Z. et. al. *ChemMedChem.* 13, 2189 (2018). Based on these scores, the structures are anticipated to have the ability to cross the blood brain barrier.

Compounds 12, 23 and 25 were also tested for Inhibition of SULT1A3 in different species. The results are in the following table.

Inhibition of SULT1A3 Homologues in Different Species. SULT1A3 is only expressed in humans and higher primates. SULT1D1 is the isoform expressed in dogs and rodents that sulfonates neurotransmitters and is most similar to SULT1A3. Three synthesized allosteres (12, 23, and 25) were tested against both 1A3 and 1D1 from different species in order to explore testing in animal models. Based on this data, the mouse is the most suitable model for animal studies. Mice have been engineered such that their SULT1A1/2 enzymes have been knocked out and replaced with the human versions of those isoforms.

Compound 12 displays low micromolar affinity for SULT1A3 and achieves 83% inhibition at saturation. Compound 23 exhibits low nanomolar affinity and almost complete inhibition at saturation. The capability of these inhibitors to potently and selectively inhibit SULT1A3 was tested and validated in cells where in the presence of the inhibitor led to reduced dopamine sulfonation, as shown in Table E.

TABLE E

Inhibition of SULT1A3 Homologues in Different Species
Species (Isoform)

| Compound | Human (1A3) $K_i$ | % inh | Green Monkey (1A3) $K_i$ | % inh | Rhesus Macaque (1A3) $K_i$ | % inh | Dog (1D1) $K_i$ | % inh | Mouse (1D1) $K_i$ | % inh | Rat (1D1) $K_i$ | % inh |
|---|---|---|---|---|---|---|---|---|---|---|---|---|
| 12 | 50 (4) | 83 (4) | 170 (21) | 71 (3) | 38 (2) | 97 (2) | 77 (4) | 83 (6) | 79 (4) | 82 (2) | 2500 (250) | 33 (4) |
| 23 | 9.6 (0.8) | 97 (2) | 72 (4) | 91 (4) | 12 (2) | 97 (2) | 117 (7) | 81 (4) | 65 (3) | 92 (3) | 270 (15) | 37 (4) |
| 25 | 17 (4) | 90 (3) | 87 (5) | 72 (5) | 25 (3) | 95 (2) | 52 (3) | 73 (4) | 32 (3) | 91 (2) | 1100 (300) | 21 (3) |

[1] Parentheses enclose one Standard Errors.

To computationally assess the cap-stabilizing effects of the inhibitors, the free energies of the closed caps were calculated with and without inhibitor bound to the E•PAPS•dopamine complex. The cap free energy was calculated, using g_energy (25,36,37), by summing the Gibbs free energy of all atoms in the system (including those of water) and subtracting from it the free energy of all non-cap atom interactions. The free energies are time-averaged values calculated using equilibrated models (see, Materials and Methods) and are a measure of the free energy of interaction of the closed cap with its milieu. To ensure that the time intervals over which the free energies were calculated are sufficiently long to average the fluctuations that occur around equilibrium, the free energy was calculated for each complex over 1, 2, 4, 6, 8 and 10 ns intervals (5 ps/frame) and the values were compared. The values agreed to within ±1% in all cases.

Inhibitor-induced changes in the free energy of the closed cap were both calculated and determined experimentally, and the values were correlated to assess the fitness of the cap-stabilization model for predicting the effects of inhibitors on turnover and further improving inhibitor design. The factor by which any two allosteric inhibitors differ in their extent of inhibition at saturation is given by the ratio of their $K_{iso}$ values, which can be calculated from the Gibbs equation:

$$\Delta\Delta G_{cap}^{O} = \Delta G_{cap(2)}^{O} - \Delta G_{cap(1)}^{O} = -RT \ln(K_{iso(2)}/K_{iso(1)}) \quad (2)$$

Subscripts 1 and 2 refer to different enzyme forms (i.e., different inhibitors bound). The $K_{iso}$ ratio can be obtained from $\Delta G_{cap}^{O}$ values calculated as described above, or from $k_{cat}$ at saturating inhibitor, as follows:

$$k_{cat} = \frac{E_O}{E_{tot}} \times k_{rel} = \frac{E_O}{E_O + E_C} \times k_{rel}, \quad (3)$$

where $E_{tot}$ represents total enzyme concentration, $E_O$ and $E_C$ represent concentrations of the cap-open cap-closed forms of the enzyme, respectively, and $k_{rel}$ is the rate constant governing release of nucleotide from the cap-open enzyme. Substituting Equation 4 into Equation 3 and rearranging yields Equation 5, $$K_{iso} = \frac{E_C}{E_O} \quad (4)$$

$$k_{cat}(1 + K_{iso}) = k_{rel} \quad (5)$$

which can be written for any two cap-closed enzyme forms. Assuming inhibitors do not affect $k_{rel}$, any two such equations can be set equal to one another and rearranged to yield:

$$\frac{k_{cat(2)}}{k_{cat(1)}} = \frac{1 + K_{iso(1)}}{1 + K_{iso(2)}} \approx \frac{K_{iso(1)}}{K_{iso(2)}}, \quad (6)$$

The $k_{cat}$ values associated with inhibitor complexes were calculated from the data compiled in Table B.

As is seen in Eq. 6, $K_{iso}$ and $k_{cat}$ ratios approach equivalence as $K_{iso}$ becomes >>1. To assess the extent to which this equivalence holds for SULT1A3, $K_{iso}$ values were determined as described previously (29-33). In short—As nucleotide binds and the cap closes, a pore forms at the acceptor-binding site. The affinity of an acceptor that is too large to pass through the pore is diminished by the presence of nucleotide, which fosters cap closure. At saturating nucleotide, the apparent affinity, $K_{app}$, of such acceptors for the fully cap-closed enzyme is given by Equation 7 (29-33), where $K_d$ is the affinity for the cap-open (nucleotide-free) form of the enzyme.

$$K_{app} = K_d \times (1 + K_{iso}) \quad (7)$$

$K_{app}$ and $K_d$ were obtained by fitting titrations that monitor changes in SULT1A3 intrinsic fluorescence as a function of the concentration of 4-hydroxytamoxifen, a large acceptor (29) (see, FIG. 2). Titrations were performed at 0 and saturating PAP (0.50 mM, 17×$K_d$). $K_{app}$ and $K_d$ are 0.41±0.03 mM and 5.4±0.3 mM, respectively, and predict that $K_{iso}$ =13±1.7. Notably, adding inhibitors will increase $K_{iso}$; consequently, the Eq. 6 approximation should hold well for studies that use inhibitors.

Plotting the calculated and experimentally determined free energies against one another (FIG. 5) reveals that the datasets are highly linearly correlated (slope=1.2±0.1). Thus, the ab initio calculations are capable of reliably predicting small changes in the free energy of a dynamic, 30-residue loop of the enzyme that is intimately involved in SULT substrate selection and turnover. Given the method's reliability, GROMACS-docked structures of inhibitor-bound complexes should provide plausible molecular explanations for the structure/activity relationships seen in the data. For example, the length of the aliphatic spacer that connects the propyl-moiety to the quinoline ring system markedly effects the inhibition, as is seen when comparing compounds 1, 2, and CMP8, which are otherwise identical. While $K_i$s for 1 and 2 could not be determined, since they do not inhibit, their $K_d$ s, determined by fluorescence titration, are 160 (±10) nM and 87 (±6) nM, respectively. Thus, while all three compounds bind tightly, only one inhibits. Structures suggest that the key to the inhibition is optimizing hydrogen bonding to Q225, which is situated in a loop whose conformation seems to be coupled to that of the cap. Further, compound 11 is identical to CMP8 except for the substitution of the amido-group for the hydroxyl at C1", which appears to engage in essentially perfect hydrogen bonding with Q255. Finally, relative to CMP8, compound 11 shifts toward Q255 and thus allows N235 and N71 to form optimal hydrogen bonding interactions. These and related insights will be incorporated into future ligand designs.

Conclusions. An allosteric pocket has been discovered in SULT1A3. Given the pocket's potential to be used to regulate catecholamine neurotransmitter activity, the solution structure of the pocket and the mechanism of allosteric inhibition were determined. Allosteres inhibit by stabilizing the closed form of the SULT1A3 active-site cap, which must open to release nucleotide. The effects of inhibitors on the closed-cap free energy were calculated using a GROMACS-based method. The calculations were used to design a series of synthetically-tractable inhibitors intended to both bind the pocket and stabilize the cap. The inhibitors were synthesized and their SULT1A3-binding and -inhibition characteristics were determined. All of the inhibitors bound well (34 nM-7.4 mM) and the predictions regarding cap stabilization and percent inhibition at saturating allosteres (0-80%) proved remarkably accurate. These findings demonstrate that it is possible to accurately calculate small changes in the free energy of a small, dynamic stretch of residues that is critically engaged in SULT substrate-selection and turnover. Efforts underway will use these methods to develop even more effective allosteric inhibitors that will be used to test the effects of preventing catecholamine sulfonation in living systems.

Materials

The materials and sources used in this study are as follows: 5,5'-dithiobis-2-nitrobenzoic acid (DTNB), dithiothreitol (DTT), ethylenediaminetetraacetic acid (EDTA), L-glutathione (reduced), 1-hydroxypyrene (1-HP), imidazole, isopropyl-thio-β-D-galacto-pyranoside (IPTG), lysozyme, 4-hydroxyl-tamoxifen (4-Tam), lysozyme, 3-maleimido-PROXYL, pepstatin A and potassium phosphate were the highest grade available from Sigma. Ampicillin, KOH, LB media, $MgCl_2$, NaCl, phenylmethylsulfonyl fluoride (PMSF), and tetramethylsilane (TMS) were purchased from Fisher Scientific. Glutathione- and nickel-chelating resins were obtained from GE Healthcare. Competent E. coli (BL21(DE3)) was purchased from Novagen. The syntheses and purification of PAPS and PAP are previously described (38) and the purity of the nucleotides was determined by anion-exchange HPLC to be ≥99%.

Computer and Software. Molecular dynamics simulations were performed using a Parallel Quantum Solutions QS32-2670C-XS8 computer. PQS Molecular Builder was purchased from Parallel Quantum Solutions (39). The source code for GROningen MAchine for Chemical Simulation (GROMACS) 4.5 was downloaded from http://www.GROMACS.org under the GROMCAS General Public License (GPL). Antechamber was acquired as part of AmberTools, under the GPL. A Genetically Optimized Ligand Docking (GOLD) license was obtained from the Cambridge Crystallographic Data Center.

Methods

SULT1A3 DNA constructs. Wild-type and mutant SULT1A3 coding regions were inserted into a pGEX-6P expression vector that fuses a triple-tag (N-His/GST/MBP)

PreScission protease cleavable protein to the SULT1A3 N-terminus (18). Mutated coding regions were constructed using PCR mutagenesis and confirmed by DNA sequencing.

SULT1A3 Expression and Purification. E. coli (BL21 (DE3)) containing the human SULT1A3 expression plasmid were grown at 37° C. in LB medium (18). At $OD_{600}$~0.6, the culture was temperature shifted to 17° C. in an ice/water bath. Upon reaching 17° C., IPTG was added (0.30 mM) and the culture was incubated at 17° C. for 18 hours. Cells were then pelleted and resuspended in lysis buffer (PMSF (290 µM), pepstain A (1.5 µM), lysozyme (0.10 mg/ml), EDTA (2.0 mM), KCl (400 mM), $K_2PO_4$ (50 mM), pH 7.5). The suspension was sonicated and then centrifuged (10,000 g, 1.0 hr, 4° C.). $MgCl_2$ (5.0 mM) was added to chelate EDTA before passing the solution through a Chelating Sepharose Fast Flow column charged with $Ni^{2+}$. The column was washed (imidazole (10 mM), KCl (400 mM), and $KPO_4$ (50 mM), pH 7.5), enzyme was eluted (imidazole (250 mM), KCl (400 mM), and $KPO_4$ (50 mM), pH 7.5) and loaded directly onto a Glutathione Sepharose column. The GST column was washed (DTT (2.0 mM), KCl (400 mM), and $KPO_4$ (50 mM), pH 7.5) before eluting the tagged enzyme (reduced glutathione (10 mM), DTT (2.0 mM), KCl (400 mM) and Tris (100 mM), pH 8.0). The fusion protein was digested overnight at 4° C. using PreScission Protease, and passed through a GST column to remove the tag. The protein was ≥95% pure as judged by SDS-PAGE, and its concentration was determined by UV absorbance ($\varepsilon_{280}$=53.9 $mM^{-1}$ $cm^{-1}$). The extinction coefficient was calculated using the ExPASy, ProtParam Tool (40). SULT1A3 concentrations determined by absorbance at 280 nm agreed with those obtained by the Bradford method (41). The pure protein was concentrated, flash frozen and stored at −80° C.

Covalent Tagging of SULT1A3 Cys Constructs. Labeling of the SULT1A3 Cys constructs was performed as described previously (18-20). Briefly, 3-maleimido-PROXYL (spin label) or N-cyclohexylmaleimide (diamagnetic label) was added to an enzyme containing solution at 20-fold excess over reactive Cys. At 3 hrs, and every hour thereafter until the reaction was complete, 50 µL aliquots from each reaction were tested for unreacted Cys using DNTB (18-20). The reactions were considered complete when >98% of the Cys was labeled. Reaction conditions: SULT1A3 (50 mM, monomer), 3-maleimido-PROXYL or N-cyclohexylmaleimide (1.0 mM), PAP (0.50 mM), $KPO_4$ (50 mM), pH 7.5, 4±2° C. To prepare samples for NMR, reaction mixtures were dialyzed three times against 40 volumes of PAP (0.50 mM), $KPO_4$ (50 mM), pD 7.4, $D_2O$ (>95%), 4±2° C. Following dialysis, labeled enzyme was assayed to ensure that the initial-rate parameters ($k_{cat}$, $K_m$ and $K_i$) were not substantially altered by Cys insertion and labelling (see, Table B).

NMR Studies. NMR experiments were performed using a Bruker 600 MHz spectrometer equipped with a TCI H/F-cryogenic probe at 298° K. Compound 8 (CMP8) peak assignments were determined from 1D-proton and -carbon spectra using $^1H$-$^{13}C$ Heteronuclear Single Quantum Coherence (HSQC) (42) and Heteronuclear Multiple Bond Correlation (HMBC) (42)—sample composition: CMP8 (1.9 mM), TMS (0.5 mM), DMSO (0.5 mM), $D_2O$≥99%, and temperature 25±1° C. Sample composition in the line-broadening studies: labelled SULT1A3 (20 µM active sites), CMP8 (100, 200, 400, or 1000 mM), PAP (500 µM, 17×$K_d$), $KPO_4$ (50 mM), pD 7.4, 25±1° C. Proton line-widths were fit to a Lorentzian distribution using NMRdraw (43).

NMR-Distance Constrained Molecular Dynamics Modeling. A ligand-free homology model of SULT1A3 was constructed from the SULT1A3•PAP•dopamine structure (PDB 2A3R (8)) using SWISS-MODEL. The model was protonated at pH 7.4 and energy minimized using GROMACS. Generalized AMBER Force Field (GAFF) energy-parameter files were constructed using Antechamber (44-46) for CMP8, PAPS, and a spin-labeled cysteine analogue in which the nitroxyl-moiety was replaced by a hydroxyl group, as described previously (18).

The cysteine analogue parameter file was added to the AMBER energy file as a non-canonical amino acid and inserted into SULT1A3 by replacing residues Q116, E198, and K234. PAPS was positioned in the active site of the ligand-less enzyme using GOLD. The system was equilibrated (298° K, NaCl (50 mM), pH 7.4) in 100 psec increments using GROMACS. Once equilibrated, CMP8 was positioned randomly in a simulated box of water (52×52×52 Å) containing the spin-labelled SULT1A3•PAPS construct, and docked using GROMACS. Docking was constrained using NMR determined, spin-label/CMP8-proton distances as described in the main text (see, NMR-distance constrained MD docking). The docking simulations were repeated 100 times, 92 of the docking experiments yielded the structure described in the main text, the remaining 8 structures showed a reversed orientation.

Molecular Dynamics Docking. Docking of CMP8 and its analogues was performed using a previously described equilibrated model of the SULT1A3•PAPS•dopamine complex without spin label (18). Briefly, compounds were positioned in the NMR-determined allosteric-binding site using GOLD, minimized with GROMACS (AMBER energy field) and equilibrated in 100 psec increments at 298° K, NaCl (50 mM), pH 7.4. Once the RMSD of the system had stabilized, indicating equilibrium had been reached, equilibrium was confirmed by ensuring that the RMSD remained stable over an additional 10 nsec.

Initial-Rate Studies. Initial-rate parameters for the labeled or mutant SULT1A3 constructs were determined using a previously described 1-HP assay (47). Briefly, reactions were initiated by addition of PAPS (0.50 mM, 17×$K_m$) to a solution containing enzyme (20 nM, active sites), 1-HP (2.0 µM, ~24×$K_m$), and $KPO_4$ (50 mM), pH 7.5, 25±2° C. Reactions were monitored via fluorescence change associated with the conversion of 1-HP to 1-HP-S ($\lambda_{ex}$=325 nm, $\lambda_{em}$=370 nm). $K_{eq}$ for the 1-HP sulfonation reaction is ~250. Given the reaction conditions outlined above, ≥99% of 1-HP is converted to 1-HP-S, and ~0.4% of PAPS is converted to PAP at equilibrium. The affinities of PAPS and PAP for SULT1A3 are comparable, and the affinity of 1-HP-S is quite low ($K_d$=240±30 µM); consequently, the conditions result in quantitative conversion of 1-HP to 1-HP-S with negligible product inhibition. Reaction progress curves were analyzed to obtain initial-rate parameters as described previously (48,49).

Inhibition studies. Inhibition parameters were determined under conditions identical to those described above (see, Initial-Rate Studies) except that [1-HP] was increased to 5.0 µM (~61×$K_m$) and inhibitor concentration was varied between 0.20-20×$K_i$. $K_i$ was obtained using a least-squares fit to the following partial inhibition equation (47,50): $V/V_{ax}=(K_i+\alpha\cdot[I])/(K_i+[I])$, where α is percentage of enzyme turnover remaining at saturating substrates and allosteric inhibitor.

Pre-Steady State Binding Studies. The pre-steady state binding of PAP to SULT1A3 was monitored via ligand-induced enzyme fluorescence changes in SULT1A3 using an Applied Photophysics SX20 stopped-flow spectrofluorimeter (29). Fluorescence was measured at $\lambda_{ex}$ 290 nm and m≥330 nm (using a cutoff filter). $k_{on}$ and $k_{off}$ of PAP binding to SULT1A3 were obtained by rapidly mixing (1:1, v:v) a solution containing SULT1A3 (25 nM, dimer), CMP8 (0 or 1.7 μM, 50×$K_d$), $KPO_4$ (50 mM), pH 7.5 with a solution that was identical except that it contained PAP (0.5, 1.0, 1.5, or 2.0 PM) and did not contain enzyme. All reactions were pseudo first order in [PAP]. The observed rate constant ($k_{obs}$) at a given [PAP] was taken as the average of three independent progress curves each obtained from a single-exponential fit of 6-9 averaged, binding progress curves. The rate constants, $k_{on}$ and $k_{off}$, were obtained from the slopes and intercepts predicted by linear least-squares analysis of four-points $k_{obs}$ vs [PAP] plots.

BIBLIOGRAPHY

1. Merikangas, K. R., He, J. P., Burstein, M., Swanson, S. A., Avenevoli, S., Cui, L., Benjet, C., Georgiades, K., and Swendsen, J. (2010) Lifetime prevalence of mental disorders in U.S. adolescents: results from the National Comorbidity Survey Replication—Adolescent Supplement (NCS-A). *J Am Acad Child Adolesc Psychiatry* 49, 980-989
2. Chesney, E., Goodwin, G. M., and Fazel, S. (2014) Risks of all-cause and suicide mortality in mental disorders: a meta-review. *World Psychiatry* 13, 153-160
3. Berton, O., and Nestler, E. J. (2006) New approaches to antidepressant drug discovery: beyond monoamines. *Nat Rev Neurosci* 7, 137-151
4. Souery, D., Amsterdam, J., de Montigny, C., Lecrubier, Y., Montgomery, S., Lipp, O., Racagni, G., Zohar, J., and Mendlewicz, J. (1999) Treatment resistant depression: methodological overview and operational criteria. *Eur Neuropsychopharmacol* 9, 83-91
5. Olgiati, P., Serretti, A., Souery, D., Dold, M., Kasper, S., Montgomery, S., Zohar, J., and Mendlewicz, J. (2018) Early improvement and response to antidepressant medications in adults with major depressive disorder. Meta-analysis and study of a sample with treatment-resistant depression. *J Affect Disord* 227, 777-786
6. Thomas, S. J., Shin, M., McInnis, M. G., and Bostwick, J. R. (2015) Combination therapy with monoamine oxidase inhibitors and other antidepressants or stimulants: strategies for the management of treatment-resistant depression. *Pharmacotherapy* 35, 433-449
7. Suominen, T., Uutela, P., Ketola, R. A., Bergquist, J., Hillered, L., Finel, M., Zhang, H., Laakso, A., and Kostiainen, R. (2013) Determination of Serotonin and Dopamine Metabolites in Human Brain Microdialysis and Cerebrospinal Fluid Samples by UPLC-MS/MS: Discovery of Intact Glucuronide and Sulfate Conjugates. *PLoS One* 8, e68007
8. Lu, J. H., Li, H. T., Liu, M. C., Zhang, J. P., Li, M., An, X. M., and Chang, W. R. (2005) Crystal structure of human sulfotransferase SULT1A3 in complex with dopamine and 3'-phosphoadenosine 5'-phosphate. *Biochem Biophys Res Commun* 335, 417-423
9. Dajani, R., Hood, A. M., and Coughtrie, M. W. (1998) A single amino acid, glu146, governs the substrate specificity of a human dopamine sulfotransferase, SULT1A3. *Mol Pharmacol* 54, 942-948
10. Hildebrandt, M. A., Salavaggione, O. E., Martin, Y. N., Flynn, H. C., Jalal, S., Wieben, E. D., and Weinshilboum, R. M. (2004) Human SULT1A3 pharmacogenetics: gene duplication and functional genomic studies. *Biochemical and biophysical research communications* 321, 870-878
11. Riches, Z., Stanley, E. L., Bloomer, J. C., and Coughtrie, M. W. (2009) Quantitative evaluation of the expression and activity of five major sulfotransferases (SULTs) in human tissues: the SULT "pie". *Drug metabolism and disposition: the biological fate of chemicals* 37, 2255-2261
12. Salman, E. D., Kadlubar, S. A., and Falany, C. N. (2009) Expression and localization of cytosolic sulfotransferase (SULT) 1A1 and SULT1A3 in normal human brain. *Drug metabolism and disposition: the biological fate of chemicals* 37, 706-709
13. Heroux, J. A., and Roth, J. A. (1988) Physical characterization of a monoamine-sulfating form of phenol sulfotransferase from human platelets. *Molecular pharmacology* 34, 194-199
14. Goldstein, D. S., Swoboda, K. J., Miles, J. M., Coppack, S. W., Aneman, A., Holmes, C., Lamensdorf, I., and Eisenhofer, G. (1999) Sources and physiological significance of plasma dopamine sulfate. *J Clin Endocrinol Metab* 84, 2523-2531
15. Strott, C. A. (2002) Sulfonation and molecular action. *Endocr Rev* 23, 703-732
16. Yamamoto, T., Yamatodani, A., Nishimura, M., and Wada, H. (1985) Determination of dopamine-3- and 4-O-sulphate in human plasma and urine by anion-exchange high-performance liquid chromatography with fluorimetric detection. *J Chromatogr* 342, 261-267
17. Le Corre, P., Malledant, Y., Tanguy, M., and Le Verge, R. (1993) Steady-state pharmacokinetics of dopamine in adult patients. *Crit Care Med* 21, 1652-1657
18. Cook, I., Wang, T., and Leyh, T. S. (2017) Tetrahydrobiopterin regulates monoamine neurotransmitter sulfonation. *Proc Natl Acad Sci USA* 114, E5317-E5324
19. Wang, T., Cook, I., and Leyh, T. S. (2017) The NSAID allosteric site of human cytosolic sulfotransferases. *J Biol Chem* 292, 20305-20312
20. Cook, I., Wang, T., Girvin, M., and Leyh, T. S. (2016) The structure of the catechin-binding site of human sulfotransferase 1A1. *Proc Natl Acad Sci USA* 113, 14312-14317
21. Solomon, I. (1955) Relaxation Processes in a System of Two Spins. *Phys Rev.* 99, 559-566
22. Girvin, M. E., and Fillingame, R. H. (1995) Determination of local protein structure by spin label difference 2D NMR: the region neighboring Asp61 of subunit c of the F1F0 ATP synthase. *Biochemistry* 34, 1635-1645
23. Gochin, M., Zhou, G., and Phillips, A. H. (2011) Paramagnetic relaxation assisted docking of a small indole compound in the HIV-1 gp41 hydrophobic pocket. *ACS Chem Biol* 6, 267-274
24. Van Der Spoel, D., Lindahl, E., Hess, B., Groenhof, G., Mark, A. E., and Berendsen, H. J. (2005) GROMACS: fast, flexible, and free. *J Comput Chem* 26, 1701-1718
25. Berendsen, H. J. C., Vanderspoel, D., and Vandrunen, R. (1995) Gromacs—a Message-Passing Parallel Molecular-Dynamics Implementation. *Comput Phys Commun* 91, 43-56
26. Schmitz, U., Ulyanov, N. B., Kumar, A., and James, T. L. (1993) Molecular dynamics with weighted time-averaged restraints for a DNA octamer. Dynamic interpretation of nuclear magnetic resonance data. *J Mol Biol* 234, 373-389
27. Battiste, J. L., and Wagner, G. (2000) Utilization of site-directed spin labeling and high-resolution heteronuclear nuclear magnetic resonance for global fold determination of large proteins with limited nuclear overhauser effect data. *Biochemistry* 39, 5355-5365

28. Wang, T., Cook, I., and Leyh, T. S. (2016) Isozyme Specific Allosteric Regulation of Human Sulfotransferase 1A1. *Biochemistry* 55, 4036-4046
29. Wang, T., Cook, I., and Leyh, T. S. (2014) 3'-Phosphoadenosine 5'-phosphosulfate allosterically regulates sulfotransferase turnover. *Biochemistry* 53, 6893-6900
30. Cook, I., Wang, T., Almo, S. C., Kim, J., Falany, C. N., and Leyh, T. S. (2013) Testing the sulfotransferase molecular pore hypothesis. *J Biol Chem* 288, 8619-8626
31. Cook, I., Wang, T., Almo, S. C., Kim, J., Falany, C. N., and Leyh, T. S. (2013) The gate that governs sulfotransferase selectivity. *Biochemistry* 52, 415-424
32. Cook, I., Wang, T., Falany, C. N., and Leyh, T. S. (2012) A nucleotide-gated molecular pore selects sulfotransferase substrates. *Biochemistry* 51, 5674-5683
33. Cook, I., Wang, T., Wang, W., Kopp, F., Wu, P., and Leyh, T. S. (2016) Controlling Sulfuryl-Transfer Biology. *Cell Chem Biol* 23, 579-586
34. Wang, T., Cook, I., and Leyh, T. (2015) The Design and Interpretation of Human SULT1A1 Assays. *Drug Metab Dispos* 44, 481-484
35. Wang, T., Cook, I., Falany, C. N., and Leyh, T. S. (2014) Paradigms of sulfotransferase catalysis: the mechanism of SULT2A1. *J Biol Chem* 289, 26474-26480
36. Van Der Spoel, D., Lindahl, E., Hess, B., Groenhof, G., Mark, A. E., and Berendsen, H. J. (2005) GROMACS: fast, flexible, and free. *J Comput Chem* 26, 1701-1718
37. Sander Pronk, Szilird Pill, Roland Schulz, Per Larsson, Par Bjelkmar, Rossen Apostolov, Michael R. Shirts, Jeremy C. Smith, Peter M. Kasson, David van der Spoel, Berk Hess, and Lindahl, E. GROMACS 4.5: a high-throughput and highly parallel open source molecular simulation toolkit.
38. Sun, M., and Leyh, T. S. (2010) The human estrogen sulfotransferase: a half-site reactive enzyme. *Biochemistry* 49, 4779-4785
39. Baker, J., Wolinski, K., Malagoli, M., Kinghorn, D., Wolinski, P., Magyarfalvi, G., Saebo, S., Janowski, T., and Pulay, P. (2009) Quantum chemistry in parallel with PQS. *J Comput Chem* 30, 317-335
40. Artimo, P., Jonnalagedda, M., Arnold, K., Baratin, D., Csardi, G., de Castro, E., Duvaud, S., Flegel, V., Fortier, A., Gasteiger, E., Grosdidier, A., Hernandez, C., Ioannidis, V., Kuznetsov, D., Liechti, R., Moretti, S., Mostaguir, K., Redaschi, N., Rossier, G., Xenarios, I., and Stockinger, H. (2012) ExPASy: SIB bioinformatics resource portal. *Nucleic Acids Res* 40, W597-603
41. Bradford, M. M. (1976) A rapid and sensitive method for the quantitation of microgram quantities of protein utilizing the principle of protein-dye binding. *Anal Biochem* 72, 248-254
42. Castanar, L., and Parella, T. (2015) Chapter Four—Recent Advances in Small Molecule NMR: Improved HSQC and HSQMBC Experiments. *Annual Reports on NMR Spectroscopy* 84, 163-232
43. Delaglio, F., Grzesiek, S., Vuister, G. W., Zhu, G., Pfeifer, J., and Bax, A. (1995) NMRPipe: a multidimensional spectral processing system based on UNIX pipes. *J Biomol NMR* 6, 277-293
44. Case, D. A., Babin, V., Berryman, J. T., R. M. Betz, R. M., Cai, Q., Cerutti, D. S., Cheatham, T. E., T. A., D., Duke, R. E., Gohlke, H., Goetz, A. W., Gusarov, S., Homeyer, N., Janowski, P., Kaus, J., Kolossváry, I., Kovalenko, A., Lee, T. S., LeGrand, S., Luchko, T., Luo, R., Madej, B., Merz, K. M., Paesani, F., Roe, D. R., Roitberg, A., Sagui, C., Salomon-Ferrer, R., Seabra, G., Simmerling, C. L., Smith, W., Swails, J., Walker, R. C., Wang, J., Wolf, R. M., X., W., and P. A., K. (2014) AMBER 14. University of California, San Francisco.
45. Wang, J., Wolf, R. M., Caldwell, J. W., Kollman, P. A., and Case, D. A. (2004) Development and testing of a general amber force field. *J Comput Chem* 25, 1157-1174
46. Wang, B., and Merz, K. M. (2006) A Fast QM/MM (Quantum Mechanical/Molecular Mechanical) Approach to Calculate Nuclear Magnetic Resonance Chemical Shifts for Macromolecules. *J Chem Theory Comput* 2, 209-215
47. Cook, I., Wang, T., Falany, C. N., and Leyh, T. S. (2015) The allosteric binding sites of sulfotransferase 1A1. *Drug Metab Dispos* 43, 418-423
48. Cook, I., Wang, T., Falany, C. N., and Leyh, T. S. (2013) High accuracy in silico sulfotransferase models. *J Biol Chem* 288, 34494-34501
49. Tang, Q., and Leyh, T. S. (2010) Precise, facile initial rate measurements. *J Phys Chem B* 114, 16131-16136
50. Whiteley, C. G. (1999) Enzyme kinetics: partial and complete non-competitive inhibition. *Biochemical Education* 27, 15-18
51. Kurogi K, Alazizi A, Liu M Y, Sakakibara Y, Suiko M, Sugahara T, and Liu M C. "Concerted actions of the catechol O-methyltransferase and the cytosolic sulfotransferase SULT1A3 in the metabolism of catecholic drugs" *Biochem Pharmacol*, 2012, 84(9), 1186-1195
52. Mesier J, Weindl D, Hiller K. "Compexity of dopamine metabolism" *Cell Communication and Signaling*, 2013, 11:34, E1-18
53. Nobili A, Latagliata E C, Vicomi M T, Cavallucci V,acqua Cutuli D, Giacovazzo G, Krashia P, Rizzo F R, Marino R, federici M, Bartolo P D, Aversa D, Dell'Acqua M C, Cordella A, Sancandi M, Keller F, Petrosini L, Puglisi-Allegra S, Mercuri N B, Coccurello R, Berretta N, D'Amelio M. "Dopamine neuronal loss contributes to memory and reward dysfunction in a model of Alzheimer's disease" *Nature Communication*, 2017, 8, 14727
54. Sternbach H. "The serotonin syndrome." *Am J Psychiatry*, 1991, 148(6), 705-713
55. Blackwell B. "Monoamine oxidase inhibitor interactions with other drugs." *J Clin Psychopharmacol*, 1991, 11(1), 55-9
56. Yamada M, Yasuhara H. "Clinical pharmacology of MAO inhibitors: safety and future" *Neurotoxicology*, 2004, 25(1-2), 215-21
57. Zou J, Li H, Huang Q, Liu Z, Qi X, Wang Y, Lu L, and Liu Z. "Dopamine-induced SULT1A3/4 promotes EMT and cancer stemness in hepatocellular carcinoma" *Tumor Biology*, 2017, 1-10

The invention claimed is:
1. A compound having the structure of formula (I):

or a pharmaceutically acceptable salt thereof, wherein:

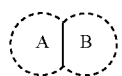

is a naphthalene or a quinoline;

X is selected from a bond and an optionally substituted alkyl or alkene;

Y is selected from —OR', —CONR'$_2$, —COOR' and optionally substituted heteroaryl;

R' is H or an optionally substituted alkyl;

Z is independently selected from H, optionally substituted alkyl, and —X-Y, or two Z together form an optionally substituted cycloalkyl, wherein when $Z_1$ and $Z_2$ are both H, then Y is heteroaryl, or wherein $Z_1$ and $Z_2$ are not both H;

a is 0 or an integer of 1-4; and wherein the compound of formula (I) is selected from:

[chemical structures]

2. A compound having the structure of formula (II):

$$Y-X-\text{[quinoline]}-Z_1, Z_2 \quad (II)$$

or a pharmaceutically acceptable salt thereof, wherein:

X is selected from a —$C_0$-$C_6$ alkyl or a —$C_2$-$C_6$ alkene;

Y is selected from —OR', —COOR', —CONR'$_2$, and heteroaryl;

R' is H or $C_1$-$C_6$ alkyl;

$Z_1$ is selected from H and —OR'; and $Z_2$ is selected from H, —$C_1$-$C_6$ alkyl, and —$C_0$-$C_6$-COOR', or $Z_1$ and $Z_2$ together form a substituted cycloalkyl, wherein when $Z_1$ and $Z_2$ are both H, then Y is heteroaryl and wherein the compound of formula (II) is selected from:

[chemical structures]

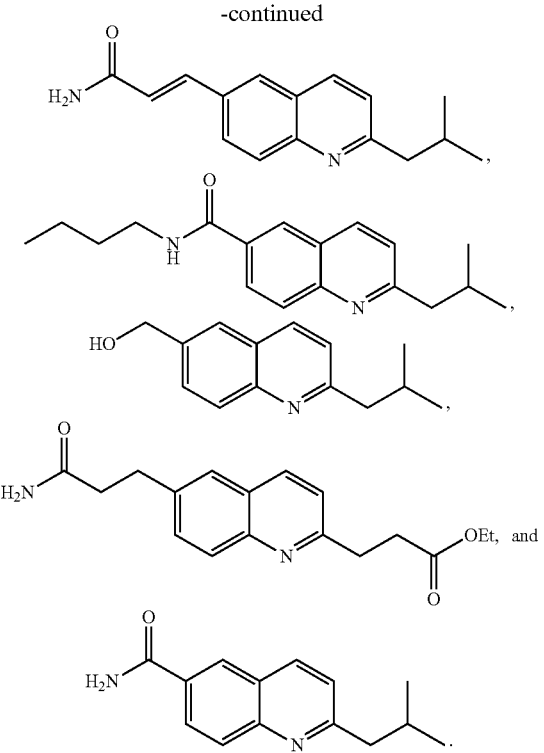

3. A pharmaceutical composition comprising a compound of claim 1, and a pharmaceutically acceptable carrier.

4. A method of inhibiting SULT1A3 in a subject in need thereof, comprising administering a compound of claim 1, or a composition comprising a compound of claim 1 in combination with a pharmaceutically acceptable carrier to the subject.

5. The method of claim 4, wherein the subject is a human.

6. A method inhibiting SULT1A3 in a cell, comprising contacting a cell with a compound of claim 1.

7. The method of claim 6, wherein the cell is a mammalian cell, and optionally wherein the mammalian cell is a human cell.

8. A method of inhibiting the activity of SULT1A3, comprising providing a SULT1A3 enzyme, and contacting the SULT1A3 enzyme with a compound of claim 1.

9. The method of claim 8, wherein:
  (a) the contacting of SULT1A3 is performed in vitro; or
  (b) the contacting of SULT1A3 is performed in vivo.

10. A method of prolonging therapeutic efficacy of a catecholic drug or lowering the effective concentration of a catecholic drug in a subject in need, comprising administering a compound of claim 1, or a composition comprising a compound of claim 1 in combination with a pharmaceutically acceptable carrier, to the subject.

11. A method of preventing metabolization of dopamine in a subject in need comprising administering a compound of claim 1, or a composition comprising a compound of claim 1 in combination with a pharmaceutically acceptable carrier, to the subject.

12. A method of retarding tumor progression of hepatocellular carcinoma in a subject in need comprising administering a compound of claim 1, or a composition comprising a compound of claim 1 in combination with a pharmaceutically acceptable carrier, to the subject.

* * * * *